US010016434B2

(12) United States Patent
Chen et al.

(10) Patent No.: US 10,016,434 B2
(45) Date of Patent: Jul. 10, 2018

(54) METHODS FOR THE TREATMENT OF HER2 AMPLIFIED CANCER

(71) Applicant: Pharmacyclics LLC, Sunnyvale, CA (US)

(72) Inventors: Jun Chen, San Jose, CA (US); Joseph J. Buggy, Mountain View, CA (US); Laurence Elias, Berkeley, CA (US)

(73) Assignee: Pharmacyclics LLC, Sunnyvale, CA (US)

( * ) Notice: Subject to any disclaimer, the term of this patent is extended or adjusted under 35 U.S.C. 154(b) by 0 days.

(21) Appl. No.: 15/652,470

(22) Filed: Jul. 18, 2017

(65) Prior Publication Data
US 2018/0071294 A1   Mar. 15, 2018

Related U.S. Application Data

(63) Continuation of application No. 15/198,694, filed on Jun. 30, 2016, now Pat. No. 9,724,349, which is a continuation of application No. 14/458,157, filed on Aug. 12, 2014, now Pat. No. 9,415,050.

(60) Provisional application No. 61/969,003, filed on Mar. 21, 2014, provisional application No. 61/865,059, filed on Aug. 12, 2013.

(51) Int. Cl.
*A61K 31/519* (2006.01)
*A61K 45/06* (2006.01)
*A61K 31/454* (2006.01)

(52) U.S. Cl.
CPC .......... *A61K 31/519* (2013.01); *A61K 31/454* (2013.01); *A61K 45/06* (2013.01)

(58) Field of Classification Search
CPC ... A61K 31/454; A61K 31/519; C07D 487/04
USPC ........................ 544/262, 350; 514/249, 262.1
See application file for complete search history.

(56) References Cited

U.S. PATENT DOCUMENTS

| 5,397,787 | A  | 3/1995  | Buzzetti et al. |
| 5,593,997 | A  | 1/1997  | Dow et al. |
| 6,160,010 | A  | 12/2000 | Uckun et al. |
| 6,221,900 | B1 | 4/2001  | Uckun et al. |
| 6,306,897 | B1 | 10/2001 | Uckun et al. |
| 6,326,469 | B1 | 12/2001 | Ullrich et al. |
| 6,506,769 | B2 | 1/2003  | Snow et al. |
| 6,660,744 | B1 | 12/2003 | Hirst et al. |
| 6,753,348 | B2 | 6/2004  | Uckun et al. |
| 6,770,639 | B2 | 8/2004  | Snow et al. |

(Continued)

FOREIGN PATENT DOCUMENTS

| CA | 2847852 A1 | 4/2008 |
| CN | 103923084 A | 7/2014 |

(Continued)

OTHER PUBLICATIONS

"Expert Scientific Group on Phase One Clinical Trials, Final Report," pp. C1, C35-C38, Nov. 30, 2006.

(Continued)

*Primary Examiner* — Craig D Ricci
*Assistant Examiner* — Janet L. Coppins
(74) *Attorney, Agent, or Firm* — Foley Hoag LLP; Hathaway P. Russell; Lucas P. Watkins

(57) ABSTRACT

Described herein are methods and compositions for treating HER2-amplified cancer. The methods include administering to an individual in need thereof ibrutinib.

14 Claims, 61 Drawing Sheets

(56) References Cited

U.S. PATENT DOCUMENTS

| | | |
|---|---|---|
| 6,921,763 B2 | 7/2005 | Hirst et al. |
| 7,138,420 B2 | 11/2006 | Bentzien et al. |
| 7,332,497 B2 | 2/2008 | Hirst et al. |
| 7,514,444 B2 | 4/2009 | Honigberg et al. |
| 7,718,662 B1 | 5/2010 | Chen et al. |
| 7,732,454 B2 | 6/2010 | Verner |
| 7,741,330 B1 | 6/2010 | Chen et al. |
| 7,825,118 B2 | 11/2010 | Honigberg et al. |
| 7,960,396 B2 | 6/2011 | Honigberg et al. |
| 8,008,309 B2 | 8/2011 | Honigberg et al. |
| 8,088,781 B2 | 1/2012 | Honigberg et al. |
| 8,158,786 B2 | 4/2012 | Honigberg et al. |
| 8,232,280 B2 | 7/2012 | Honigberg et al. |
| 8,236,812 B2 | 8/2012 | Honigberg et al. |
| 8,306,897 B2 | 11/2012 | Yolles |
| 8,399,470 B2 | 3/2013 | Honigberg et al. |
| 8,476,264 B2 | 7/2013 | Honigberg et al. |
| 8,497,277 B2 | 7/2013 | Honigberg et al. |
| 8,501,724 B1 | 8/2013 | Chen et al. |
| 8,501,751 B2 | 8/2013 | Honigberg et al. |
| 8,552,010 B2 | 10/2013 | Honigberg et al. |
| 8,563,563 B2 | 10/2013 | Honigberg et al. |
| 8,633,311 B2 | 1/2014 | Bommer et al. |
| 8,642,604 B2 | 2/2014 | Knight et al. |
| 8,658,653 B2 | 2/2014 | Honigberg et al. |
| 8,691,546 B2 | 4/2014 | Honigberg et al. |
| 8,697,711 B2 | 4/2014 | Honigberg et al. |
| 8,703,760 B2 | 4/2014 | Honigberg et al. |
| 8,735,403 B2 | 5/2014 | Honigberg et al. |
| 8,735,404 B2 | 5/2014 | Honigberg et al. |
| 8,741,908 B2 | 6/2014 | Honigberg et al. |
| 8,748,438 B2 | 6/2014 | Honigberg et al. |
| 8,748,439 B2 | 6/2014 | Honigberg et al. |
| 8,754,090 B2 | 6/2014 | Buggy et al. |
| 8,754,091 B2 | 6/2014 | Honigberg et al. |
| 8,759,516 B2 | 6/2014 | Honigberg et al. |
| 8,809,273 B2 | 8/2014 | Honigberg et al. |
| 8,883,435 B2 | 11/2014 | Honigberg et al. |
| 8,883,803 B2 * | 11/2014 | Honigberg ............ A61K 31/00 424/133.1 |
| 8,940,750 B2 | 1/2015 | Honigberg et al. |
| 8,952,015 B2 | 2/2015 | Honigberg et al. |
| 8,957,079 B2 | 2/2015 | Honigberg et al. |
| 8,975,266 B2 | 3/2015 | Honigberg et al. |
| 8,987,233 B2 | 3/2015 | Pan et al. |
| 8,999,999 B2 | 4/2015 | Buggy et al. |
| 9,012,463 B2 | 4/2015 | Chen et al. |
| 9,079,908 B2 | 7/2015 | Honigberg et al. |
| 9,107,924 B2 | 8/2015 | Buggy et al. |
| 9,117,924 B2 | 8/2015 | Kitagawa et al. |
| 9,125,889 B2 | 9/2015 | Buggy et al. |
| 9,127,012 B2 | 9/2015 | Honigberg et al. |
| 9,133,198 B2 | 9/2015 | Honigberg et al. |
| 9,133,201 B2 | 9/2015 | Honigberg et al. |
| 9,133,202 B2 | 9/2015 | Honigberg et al. |
| 9,139,591 B2 | 9/2015 | Honigberg et al. |
| 9,181,257 B2 | 11/2015 | Honigberg et al. |
| 9,181,263 B2 | 11/2015 | Honigberg et al. |
| 9,193,735 B2 | 11/2015 | Honigberg et al. |
| 9,206,189 B2 | 12/2015 | Honigberg et al. |
| 9,212,185 B2 | 12/2015 | Honigberg et al. |
| 9,266,893 B2 | 2/2016 | Honigberg et al. |
| 9,278,100 B2 | 3/2016 | Honigberg et al. |
| 9,296,753 B2 | 3/2016 | Smyth et al. |
| 9,409,911 B2 | 8/2016 | Honigberg et al. |
| 9,421,208 B2 | 8/2016 | Balasubramanian |
| 9,540,382 B2 | 1/2017 | Purro et al. |
| 9,556,182 B2 | 1/2017 | Honigberg et al. |
| 9,724,349 B2 | 8/2017 | Chen et al. |
| 9,795,605 B2 | 10/2017 | Buggy et al. |
| 2002/0016460 A1 | 2/2002 | Snow et al. |
| 2002/0155505 A1 | 10/2002 | Wells et al. |
| 2003/0013125 A1 | 1/2003 | Braisted et al. |
| 2003/0035833 A1 | 2/2003 | He |
| 2003/0040461 A1 | 2/2003 | McAtee |
| 2003/0125235 A1 | 7/2003 | Foxwell |
| 2004/0006083 A1 | 1/2004 | Hirst et al. |
| 2005/0008640 A1 | 1/2005 | Waegell et al. |
| 2005/0084905 A1 | 4/2005 | Prescott et al. |
| 2005/0090499 A1 | 4/2005 | Currie et al. |
| 2005/0101604 A1 | 5/2005 | Currie et al. |
| 2005/0196851 A1 | 9/2005 | Uckun |
| 2005/0209255 A1 | 9/2005 | Jimenez et al. |
| 2006/0079494 A1 | 4/2006 | Santi et al. |
| 2006/0167090 A1 | 7/2006 | Uckun et al. |
| 2006/0178367 A1 | 8/2006 | Currie et al. |
| 2007/0065449 A1 | 3/2007 | Verschraegen |
| 2007/0105136 A1 | 5/2007 | Staudt et al. |
| 2007/0281907 A1 | 12/2007 | Watkins |
| 2008/0108636 A1 | 5/2008 | Honigberg et al. |
| 2008/0214501 A1 | 9/2008 | Pan et al. |
| 2009/0098137 A1 | 4/2009 | Burke et al. |
| 2009/0105209 A1 | 4/2009 | Dewdney et al. |
| 2009/0186898 A1 | 7/2009 | Dewdney et al. |
| 2009/0317836 A1 | 12/2009 | Kuhn et al. |
| 2010/0016296 A1 | 1/2010 | Singh et al. |
| 2010/0022561 A1 | 1/2010 | Honigberg et al. |
| 2010/0041677 A1 | 2/2010 | Honigberg et al. |
| 2010/0087482 A1 | 4/2010 | Haber et al. |
| 2010/0222325 A1 | 9/2010 | Berthel et al. |
| 2010/0254905 A1 | 10/2010 | Honigberg et al. |
| 2010/0324050 A1 | 12/2010 | Honigberg et al. |
| 2011/0039868 A1 | 2/2011 | Honigberg et al. |
| 2011/0086866 A1 | 4/2011 | Chen et al. |
| 2011/0177011 A1 | 7/2011 | Currie et al. |
| 2011/0224235 A1 | 9/2011 | Honigberg et al. |
| 2011/0244465 A1 | 10/2011 | Harvey et al. |
| 2011/0281322 A1 | 11/2011 | Honigberg et al. |
| 2012/0065201 A1 | 3/2012 | Honigberg et al. |
| 2012/0071497 A1 | 3/2012 | Buggy et al. |
| 2012/0087915 A1 | 4/2012 | Buggy et al. |
| 2012/0088912 A1 | 4/2012 | Honigberg et al. |
| 2012/0095026 A1 | 4/2012 | Honigberg et al. |
| 2012/0100138 A1 | 4/2012 | Buggy et al. |
| 2012/0101113 A1 | 4/2012 | Honigberg et al. |
| 2012/0101114 A1 | 4/2012 | Honigberg et al. |
| 2012/0108547 A1 | 5/2012 | Jankowski et al. |
| 2012/0108612 A1 | 5/2012 | Honigberg et al. |
| 2012/0115889 A1 | 5/2012 | Honigberg et al. |
| 2012/0122894 A1 | 5/2012 | Honigberg et al. |
| 2012/0129821 A1 | 5/2012 | Honigberg et al. |
| 2012/0129873 A1 | 5/2012 | Honigberg et al. |
| 2012/0135944 A1 | 5/2012 | Honigberg et al. |
| 2012/0165328 A1 | 6/2012 | Honigberg et al. |
| 2012/0178753 A1 | 7/2012 | Honigberg et al. |
| 2012/0183535 A1 | 7/2012 | Buggy et al. |
| 2012/0184013 A1 | 7/2012 | Honigberg et al. |
| 2012/0184567 A1 | 7/2012 | Honigberg et al. |
| 2012/0202264 A1 | 8/2012 | Honigberg et al. |
| 2012/0202611 A1 | 8/2012 | Warren |
| 2012/0214826 A1 | 8/2012 | Honigberg et al. |
| 2012/0219522 A1 | 8/2012 | Xi |
| 2012/0252821 A1 | 10/2012 | Honigberg et al. |
| 2012/0252822 A1 | 10/2012 | Honigberg et al. |
| 2012/0277225 A1 | 11/2012 | Honigberg et al. |
| 2012/0277254 A1 | 11/2012 | Honigberg et al. |
| 2012/0277255 A1 | 11/2012 | Honigberg et al. |
| 2012/0283276 A1 | 11/2012 | Honigberg et al. |
| 2012/0283277 A1 | 11/2012 | Honigberg et al. |
| 2012/0296089 A1 | 11/2012 | Honigberg et al. |
| 2012/0329130 A1 | 12/2012 | Honigberg et al. |
| 2013/0005745 A1 | 1/2013 | Honigberg et al. |
| 2013/0005746 A1 | 1/2013 | Honigberg et al. |
| 2013/0012525 A1 | 1/2013 | Honigberg et al. |
| 2013/0016060 A1 | 1/2013 | Honigberg et al. |
| 2013/0035334 A1 | 2/2013 | Honigberg et al. |
| 2013/0041014 A1 | 2/2013 | Lavitrano et al. |
| 2013/0195852 A1 | 8/2013 | Buggy et al. |
| 2013/0202611 A1 | 8/2013 | Buggy et al. |
| 2013/0273030 A1 | 10/2013 | Buggy et al. |
| 2013/0310402 A1 | 11/2013 | Buggy et al. |
| 2013/0336172 A1 | 12/2013 | Smyth et al. |
| 2014/0057907 A1 | 2/2014 | Honigberg et al. |
| 2014/0079690 A1 | 3/2014 | Buggy et al. |

(56) References Cited

U.S. PATENT DOCUMENTS

| | | |
|---|---|---|
| 2014/0126414 A1 | 5/2014 | Honigberg et al. |
| 2014/0128413 A1 | 5/2014 | Honigberg et al. |
| 2014/0135347 A1 | 5/2014 | Honigberg et al. |
| 2014/0142123 A1 | 5/2014 | Honigberg et al. |
| 2014/0163027 A1 | 6/2014 | Verner et al. |
| 2014/0163046 A1 | 6/2014 | Honigberg et al. |
| 2014/0171453 A1 | 6/2014 | Honigberg et al. |
| 2014/0243355 A1 | 6/2014 | Honigberg et al. |
| 2014/0187564 A1 | 7/2014 | Honigberg et al. |
| 2014/0187565 A1 | 7/2014 | Honigberg et al. |
| 2014/0194446 A1 | 7/2014 | Buggy et al. |
| 2014/0212465 A1 | 7/2014 | Honigberg et al. |
| 2014/0275125 A1 | 9/2014 | Honigberg et al. |
| 2014/0303191 A1 | 10/2014 | Buggy et al. |
| 2014/0336206 A1 | 11/2014 | Honigberg et al. |
| 2014/0378446 A1 | 12/2014 | Chen et al. |
| 2015/0018336 A1 | 1/2015 | Chen et al. |
| 2015/0031710 A1 | 1/2015 | Buggy et al. |
| 2015/0031711 A1 | 1/2015 | Buggy et al. |
| 2015/0118222 A1 | 4/2015 | Levy et al. |
| 2015/0133661 A1 | 5/2015 | Honigberg et al. |
| 2015/0140036 A1 | 5/2015 | Mannick et al. |
| 2015/0152115 A1 | 6/2015 | Honigberg et al. |
| 2015/0158871 A1 | 6/2015 | Purro et al. |
| 2015/0238490 A1 | 8/2015 | Burger |
| 2015/0239897 A1 | 8/2015 | Chen et al. |
| 2015/0265618 A1 | 9/2015 | Honigberg et al. |
| 2015/0297590 A1 | 10/2015 | Fultz et al. |
| 2015/0306103 A1 | 10/2015 | Honigberg et al. |
| 2015/0307500 A1 | 10/2015 | Honigberg et al. |
| 2016/0243033 A1 | 8/2016 | Buggy et al. |

FOREIGN PATENT DOCUMENTS

| | | |
|---|---|---|
| EP | 1473039 A1 | 11/2004 |
| WO | WO-1997/028161 A1 | 8/1997 |
| WO | WO-1999/054286 A2 | 10/1999 |
| WO | WO-2000/000823 | 1/2000 |
| WO | WO-2000/056737 | 9/2000 |
| WO | WO-2001/019829 A2 | 3/2001 |
| WO | WO-2001/019829 A3 | 3/2001 |
| WO | WO-2001/025238 | 4/2001 |
| WO | WO-2001/041754 | 6/2001 |
| WO | WO-2001/044258 A1 | 6/2001 |
| WO | WO-2002/038797 | 5/2002 |
| WO | WO-2002/076986 A1 | 10/2002 |
| WO | WO-2002/080926 | 10/2002 |
| WO | WO-2003/000187 | 1/2003 |
| WO | WO-2003/013540 | 2/2003 |
| WO | WO-2003/046200 | 6/2003 |
| WO | WO-2003/097645 | 11/2003 |
| WO | WO-2004/074290 A1 | 9/2004 |
| WO | WO-2004/096253 A1 | 11/2004 |
| WO | WO-2004/100868 A2 | 11/2004 |
| WO | WO-2004/100868 A3 | 11/2004 |
| WO | WO-2005/000197 A2 | 1/2005 |
| WO | WO-2005/005429 A1 | 1/2005 |
| WO | WO-2005/014599 A1 | 2/2005 |
| WO | WO-2005/037843 A1 | 4/2005 |
| WO | WO-2005/060956 A1 | 7/2005 |
| WO | WO-2005/074603 A2 | 8/2005 |
| WO | WO-2006/036527 A1 | 4/2006 |
| WO | WO-2006/036788 A2 | 4/2006 |
| WO | WO-2006/036941 A2 | 4/2006 |
| WO | WO-2006/050946 A1 | 5/2006 |
| WO | WO-2006/053121 A2 | 5/2006 |
| WO | WO-2006/099075 A2 | 9/2006 |
| WO | WO-2006/124462 A2 | 11/2006 |
| WO | WO-2007/002325 A1 | 1/2007 |
| WO | WO-2007/058832 A2 | 5/2007 |
| WO | WO-2007/087068 A2 | 8/2007 |
| WO | WO-2007/136790 A2 | 11/2007 |
| WO | WO-2008/039218 A2 | 4/2008 |
| WO | WO-2008/054827 A2 | 5/2008 |
| WO | WO-2008/108636 A1 | 9/2008 |
| WO | WO-2008/121742 A2 | 10/2008 |
| WO | WO-2008/124138 A1 | 10/2008 |
| WO | WO-2009/051822 A1 | 4/2009 |
| WO | WO-2009/158571 A1 | 12/2009 |
| WO | WO-2010/009342 A2 | 1/2010 |
| WO | WO-2010/009342 A3 | 1/2010 |
| WO | WO-2010/065898 A2 | 6/2010 |
| WO | WO-2010/126960 A1 | 11/2010 |
| WO | WO-2011/034907 A2 | 3/2011 |
| WO | WO-2011/153514 A2 | 12/2011 |
| WO | WO-2011/162515 A2 | 12/2011 |
| WO | WO-2012/021444 A1 | 2/2012 |
| WO | WO-2012/158764 A1 | 11/2012 |
| WO | WO-2013/059738 A2 | 4/2013 |
| WO | WO-2014/004707 A1 | 1/2014 |
| WO | WO-2014/018567 A1 | 1/2014 |
| WO | WO-2014/135669 A1 | 9/2014 |
| WO | WO-2014/168975 A1 | 10/2014 |
| WO | WO-2015/127234 A1 | 8/2015 |

OTHER PUBLICATIONS

ACS 2015 (http://www.cancer.org/cancer/non-hodgkinlymphoma/detailedguide/non-hodgkin-lymphoma-types-of-non-hodgkinlymphoma).

Adimoolam et al. HDAC inhibitor PCI-24781 decreases RAD51 expression and inhibits homologous recombination. PNAS 104 (49):19482-19487 (2007).

Advani et al. Effect of Btk inhibitor PCI-32765 monotherapy on responses in patients with relapsed aggressive NHL: Evidence of antitumor activity from a phase I study. J. Clin. Oncol., 2010 ASCO Annual Meeting Proceedings (Post-Meeting Edition), 28(15 Supp):8012 (2010).

Advani et al., "The Btk inhibitor PCI-32765 is highly active and well tolerated in patients (PTS) with relapsed/refractory B cell malignancies: final results from a phase I study," Ann Oncol, 22(Supp 4):abstract 153 (2011).

Advani, R.H., et al., 2013, "Bruton tyrosine kinase inhibitor Ibrutinib (PCI-32765) ha significant activity in patients with relapsed/refractory B-cell malignancies", Journal of Clinical Oncology, vol. 31, No. 1 ,pp. 88-94.

Agathocleous et al. Preliminary Results of a Phase I/II Study of Weekly or Twice Weekly Bortezomib in Combination with Rituximab, in Patients with Follicular Lymphoma, Mantle Cell Lymphoma and Waldenstrom's Macroglobulinaemia. Blood (ASH Annual Meeting Abstracts) 110:Abstract 2559 (2007).

Ahn et al. Michael acceptors as a tool for anticancer drug design. Current Pharmaceutical Design 2(3):247-262 (1996).

American Cancer Society Melanoma Guidelines (2014).

Anderson. The process of structure-based drug design. Chem and Biol 10:787-797 (2003).

Apsel et al. Targeted Polypharmacology: Discovery of Dual Inhibitors of Tyrosine and Phosphoinositide Kinases. Nature Chem. Bio., 4(11):691-699 (2008).

Arkin et al. HER-2-directed, small-molecule antagonists. Curr Opin Investig Drugs. 2008;9(12):1264-1276. (saved on H drive and filesite).

Arnold et al. Pyrrolo[2,3-d]pyrimidines Containing an Extended 5-Substituent as Potent and Selective Inhibitors of Ick 1. Bioorg. Med. Chem. Ltrs. 10:2167-2170 (2000).

Asrani et al. The HER2- and heregulin 11 (HRG)-inducible TNFR superfamily member Fn14 promotes HRG-driven breast cancer cell migration, invasion, and MMP9 expression. Mol Cancer Res. Apr. 2013;11(4):393-404. doi: 10.1158/1541-7786.MCR-12-0542. Epub Feb. 1, 2013.

Banker et al. Modern Pharmaceutics, 3ed., Marcel Dekker, New York 1996, p. 596.

Baselga. Targeting tyrosine kinases in cancer: the second wave. Science 312(5777):1175-1178 (2006).

Bhalla et al. PCI-24781 induces caspase and reactive oxygen species-dependent apoptosis through NF-kappaB mechanisms and is synergistic with bortezomib in lymphoma cells. Clin Cancer Res 15:3354-3365 (2009).

(56) References Cited

OTHER PUBLICATIONS

Biospace, 20091208, pharmacyclics, Inc. (PCYC) announces presentation of interim results from phase I trial of its first-in-human btk inhibitor PCI-32765.
Brown et al. Phase Ib trial of AVL-292, a covalent inhibitor of Bruton's tyrosine kinase (Btk), in chronic lymphocytic leukemia (CLL) and B-non-Hodgkin lymphoma (B-NHL). J Clin. Oncol. 30(suppl):abstract 8032 (2012); [online][retrieved on Oct. 4, 2012] Retrieved from the Internet: < http://www.asco.org/ASCOv2/Meetings/Abstracts?&vmview=abst_detail_view&confID=114&abstractID=98841>.
Browning. B cells move to centre stage: novel opportunities for autoimmune disease treatment. Nature Reviews/Drug Discovery 5:564-576 (Jul. 2006).
Burchat et al. Pyrazolo[3,4-d]pyrimidines Containing an Extended 3-Substituent as Potent Inhibitors of Lck—a Selectivity Insight. Bioorg. Med. Chem. Ltrs. 12:1687-1690 (2002).
Burger et al. High-Level Expression of the T-Cell Chemokines CCL3 and CCL4 by Chronic Lymphocytic Leukemia B Cells in Nurselike Cell Cocultures and After BCR Stimulation. Blood 113(13):3050-3058 (2008).
Burger et al. The Btk Inhibitor Inbrutinib (PCI-32765) in Combination with Rituximab is Well Tollerated and Displays Profound Activity in High-Risk Chronic Lyphocytic Leukemia (CLL) Patients. Blood (ASH Annual Meeing Abstracts).120:Abstract 187 (2012).
Burger. Targeting the microenvironment in chronic lymphocytic leukemia is changing the therapeutic landscape. Curr. Opin. Oncol. 24(6):643-649 (Epub Sep. 6, 2012/Nov. 2012).
Byrd et al. Targeting BTK with Ibrutinib in relapsed chronic lymphocytic leukemia, NEJM 369(1):32-42 (Jul. 4, 2013).
Byrd J.C., et al., "Three-year follow-up of treatment-naïve and previously treated patients with CLL and SLL receiving single-agent ibrutinib", Blood, Apr. 16, 2015, vol. 125 (16), pp. 2497-2506.
Carmi et al. Clinical perspectives for irreversible tyrosine kinase inhibitors in cancer. Biochem. Pharmacol. (Epub Aug. 4, 2012) 84(11):1388-1399 (Dec. 2012).
Carrle et al. Current Strategies of Chemotherapy in Osteosarcoma. International Orthopaedics 30:445-451 (2006).
Chang et al. Egress of CD19+CD5+ cells into peripheral blood following treatment with the Bruton tyrosine kinase inhibitor inbrutinib in mantel cell lymphoma patients. Blood, 122:2412-2424 (2013).
Chang et al., "PCI-45292, a novel Btk inhibitor with optimized pharmaceutical properties, demonstrates potent activities in rodent models of arthritis," ACR/ARHP Scientific Meeting, Poster #286 (2010).
Chang et al., "The Bruton tyrosine kinase inhibitor PCI-32765 ameliorates autoimmune arthritis by inhibition of multiple effector cells," Arhtritis Res Ther, 13:R115 (2011).
Chen et al. SYK-dependent tonic B-cell receptor signaling is a rational treatment target in diffuse large B-cell lymphoma. Blood 111(4):2230-2237 (2008) [E-pub Nov. 15, 2007].
Cohen et al. Structural Bioinformatics-Based Design of Selective, Irreversible Kinase Inhibitors. Science 308:1318-1321 (May 27, 2005).
Combination treatment of the Bruton's tyrosine kinase inhibitor ibrutinib and carfilzomib in patients with relapsed or relapsed and refractory multiple myeloma: initial results from a multicenter phase 1/2b study. NCT01962792 (2015).
Czuczman et al. Rituximab in combination with fludarabine chemotherapy in low-grade or follicular lymphoma. J. Clin. Oncol. 23(4):694-704 (Feb. 1, 2005).
D'Cruz et al. Novel Bruton's tyrosine kinase inhibitors currently in development. OncoTargets and Therapy 6:161-176 (2013).
Dana-Farber Cancer Institute. A Phase II Study of Ibrutinib Plus FCR in Previously Untreated, Younger Patients With Chronic Lymphocytic Leukemia (iFCR). In: ClinicalTrials.gov [Internet]. Bethesda (MD): National Library of Medicine (US). Sep. 23, 2014 [cited Feb. 5, 2015] Available from: https://clinicaltrial.gov/ct2/show/NCT02251548?term=NCT02251548 NLM Identifier: NCT02251548.
Dana-Farber Cancer Institute. Ibrutinib (PCI-32765) in Waldenstrom's Macroglobulinemia. In: ClinicalTrials.gov [Internet]. Bethesda (MD): National Library of Medicine (US). May 17, 2012—[cited Nov. 22, 2013]. Available from: http://clinicaltrials.gov/ct2/show/NCT01614821 NLM Identifier: NCT01614821.
Davids et al. Targeting the B Cell Receptor Pathway in Chronic Lymphocytic Leukemia. Leuk. Lymphoma (Epub May 23, 2012), 53(12):2362-2370 (Dec. 2012).
Davis et al., "Chronic active B-cell receptor signalling in diffuse large B-cell lymphoma," Nature, 463(7277):88-92 (2010).
Desiderio. Role of Btk in B cell development and signaling. Curr. Op. in Immunology 1997, 9:534-540.
Devos et al., "The Bruton's tyrosine kinase (BTK) inhibitor, ibrutinib (PCI-32765), has preferential activity in the activated B cell-like (ABC) subtype of relapsed/refractory (RR) DLBCL: interim phase 2 results," Haematologica 98(s1):490 (2013).
Dorwald, F.Z., "Side Reactions in Organic Synthesis," Wiley:VCH, Weinheim p. IX of Preface, Wiley-VCH Verlag GmbH & C KGaA (2005).
Dy et al., "Understanding, recognizing, and managing toxicities of targeted anticancer therapies," CA: A Cancer Journal for Clinicians, 63(4): 249-279 (2013).
Edwards. BTK inhibition in myeloma: targeting the seed and the soil. Blood 120(9):1757-1759 (Aug. 2012).
Elias et al. BTK Inhibitor Ibrutinib Inhibits Breast Cancer Growth by Inhibiting ErbB Kinases. Mol Cancer Ther. 2013;12:C258. (not available on pubmed).
Eurasian Search Report for Eurasian Application No. EA201000599 dated Nov. 15, 2010.
European Examination Report for European Application No. EP 06744513.6 dated Jan. 16, 2013.
European Examination Report for European Application No. EP 12151943.3 dated Feb. 5, 2013.
European Examination Report for European Application No. EP 12166305.8 dated Dec. 3, 2013.
Extended European Search Report for European Applicatin No. EP 12166301.7 dated Nov. 6, 2012.
Extended European Search Report for European Application No. EP 06850039.6 dated Feb. 15, 2010.
Extended European Search Report for European Application No. EP 06850386.1 dated Sep. 10, 2010.
Extended European Search Report for European Application No. EP 08744513.6 dated Mar. 18, 2010.
Extended European Search Report for European Application No. EP 09798770.5 dated Oct. 28, 2011.
Extended European Search Report for European Application No. EP 10155834.4 dated May 27, 2010.
Extended European Search Report for European Application No. EP 10823966.6 dated Oct. 17, 2011.
Extended European Search Report for European Application No. EP 12151943.3 dated Mar. 13, 2012.
Extended European Search Report for European Application No. EP 12166295.1 dated Nov. 6, 2012.
Extended European Search Report for European Application No. EP 12166296.9 dated Nov. 8, 2012.
Extended European Search Report for European Application No. EP 12166298.5 dated Nov. 7, 2012.
Extended European Search Report for European Application No. EP 12166300.9 dated Oct. 31, 2012.
Extended European Search Report for European Application No. EP 12166302.5 dated Nov. 6, 2012.
Extended European Search Report for European Application No. EP 12166305.8 dated Nov. 6, 2012.
Extended European Search Report for European Application No. EP 12166306.6 dated Nov. 8, 2012.
Extended European Search Report for European Application No. EP 12172840.6 dated Dec. 12, 2012.
Extended European Search Report for European Application No. EP 12172841.4 dated Jan. 2, 2013.

(56) References Cited

OTHER PUBLICATIONS

Extended European Search Report for European Application No. EP 12172842.2 dated May 14, 2013.
Extended European Search Report for European Application No. EP 12172843.0 dated Jan. 18, 2013.
Ezell S.A., et al., "Synergistic Induction of Apoptosis by Combination of BTK and Dual mTORC1/2 Inhibitors in Diffuse Large B Cell Lymphoma," Oncotarget, 2014, vol. 5 (13), pp. 4990-5001.
Fabian et al. A small molecule-kinase interaction map for clinical kinase inhibitors. Nature Biotechnology, 23(3): 329-336 (2005).
Fisher et al. Prolonged disease-free survival in Hodgkin's disease with MOPP reinduction after first relapse. Ann. Intern. Med., 90(5):761-763 (1979).
Fowler et al. The Btk Inhibitor, PCI-32765, Induces Durable Responses with Minimal Toxicity in Patients with Relapsed/Refractory B-Cell Malignancies: Results From a Phase 1 Study. Blood (ASH Annual Meeting) 116 (21), p. 425:Abstract 964 (2010).
Fowler et al., "The Bruton's tyrosine kinase inhibitor ibrutinib (PCI-32765) is active and tolerated in relapsed follicular lymphoma," 54th American Society of Hematology Annual Meeting and Exposition, Abstract 156 (2012).
Friedberg et al. Inhibition of Syk with fostamatinib disodium has significant clinical activity in non-Hodgkin lymphoma and chronic lymphocytic leukemia. Blood 115(13):2578-2565 (2010) [E-pub Nov. 17, 2009].
Fruman. Xid-like Phenotypes: A B Cell Signalosome Takes Shape. Immunity 13:1-3 (Jul. 2000).
Gazitt et al. Differential mobilization of CD34+ Cells and lymphoma cells in non-Hodgkin's lymphoma patients mobilized with different growth factors, J of Hematotherapy & Stem Cell Research 10:167-176 (2001).
Ghia. Ibrutinib: better combined with other drugs? Lancet 15:1043-1044 (2014).
Giuliani. Multiple myeloma bone disease: pathophysiology of osteoblast inhibition. Blood (Epub Aug. 17, 2006) 108(13):3992-3996 (2006).
Glassman et al., "The value of fluorescence in situ hybridization in the diagnosis and prognosis of chronic lymphocytic leukemia," Cancer Genet Cytogen, 158:88-91 (2005).
Gold. To make antibodies or not:signaling by the B-cell antigen receptor. Trends in Pharmacological Sciences, 23(7):316-324 (Jul. 2002).
Gordon et al. Somatic hypermutation of the B cell receptor genes 829 (Igb, CD79b) and mb1 (Iga, CD79a). PNAS 100(7):4126-4131 (2003).
Grabinski et al., "Ibrutinib (ImbruvicaTM) Potently Inhibits ErbB Receptor Phosphorylation and Cell Viability of ErbB2-Positive Breast Cancer Cells," Invest New Drug, 32(6): 1096-1104 (Aug. 1, 2014).
Gura, "Systems for Identifying New Drugs are Often Faulty," Science, 278(5340): 1041-1042 (1997).
Hagemeister. Rituximab for the treatment of non-Hodgkin's lymphoma and chronic lymphocytic leukaemia. Drugs 70(3):261-272 (2010).
Hantschel et al. The Btk Tyrosine Kinase is a Major Target of the Bcr-Abl Inhibitor Dasatinib. PNAS 104(33):13283-13288 (2007).
Hata et al. Bruton's tyrosine kinase-mediated Interleukin-2 gene activation in mast cells. J. Biol. Chem. 273(18): 10979-10987 (1998).
Herman et al. Bruton tyrosine kinase represents a promising therapeutic target for treatment of chronic lymphocytic leukemia and is effectively targeted by PCI-32765. Blood (Epub Mar. 21, 2011), 117(23):6287-6296 (Jun. 2011).
Hiddeman et al. Rituximab Plus Chemotherapy in Follicular and Mantle Cell Lymphomas, Seminars in Oncology 30(1)Suppl.2:16-20 (Feb. 2003).
Hiddeman et al., "Frontline therapy with rituximab added to the combination of cyclophosphamide, doxorubicin, vincristine, and prednisone (CHOP) significantly improves the outcome for patients with advanced-stage follicular lymphoma compared with therapy with CHOP alone: results of a prospective randomized study of the German low-grade lymphoma study group," Blood, 106(12):3725-32 (2005).
Honigberg et al. Targeting Btk in lymphoma: PCI-32765 inhibits tumor growth in mouse lymphoma models and a fluorescent analog of PCI-32765 is an active-site probe that enables assessment of Btk inhibition in vivo. ASH Annual Meeting Abstracts 1592. 110(11): 475A (2007).
Honigberg et al. The Bruton tyrosine kinase inhibitor PCI-32765 blocks B-cell activation and is efficacious in models of autoimmune disease and B-cell malignancy. PNAS USA 107:13075-13080 (2010).
Horwood et al. Bruton's Tyrosine Kinase is Required for Lipopolysaccharide-induced Tumor Necrosis Factor α Production. J. Exp. Med. 197(12):1603-1611 (Jun. 2003).
http://www.uspto.gov/web/offices/pac/dapp/1pecba.htm#7, last accessed Feb. 16, 2011.
Huhn et al. Rituximab therapy of patients with B-cell chronic lymphocytic leukemia. Blood 98(5):1326-1331 (Sep. 1, 2001).
Hurrell et al. The in vitro influences of epidermal growth factor and heregulin-β1 on the efficacy of trastuzumab used in Her-2 positive breast adenocarcinoma. Cancer Cell Int. Oct. 11, 2013;13(1):97. doi: 10.1186/1475-2867-13-97.
Inhibitory effects of the BTK inhibitor, ibrutinib, on HER2-amplified breast cancer growth, cell cycle progression, and clonogenicity—Poster.
International Preliminary Report on Patentability for International Application No. PCT/US2006/49626 dated Mar. 24, 2009.
International Preliminary Report on Patentability for International Application No. PCT/US2009/050897 dated Jan. 27, 2011.
International Preliminary Reporton Patentability for International Application No. PCT/US2014/050783 dated Feb. 16, 2016.
International Search Report and Written Opinion for International Application No. PCT/US2008/058528 dated Sep. 30, 2008.
International Search Report and Written Opinion for International Application No. PCT/US2010/052377 dated Jun. 29, 2011.
International Search Report and Written Opinion for International Application No. PCT/US2014/050783 dated Nov. 18, 2014.
International Search Report for International Application No. PCT/US16/44916 dated Dec. 16, 2016.
International Search Report for International Application No. PCT/US2006/049626 dated Apr. 9, 2008.
International Search Report for International Application No. PCT/US2009/050897 dated Mar. 15, 2010.
International Search Report for International Application No. PCT/US2015/046401 dated Nov. 25, 2015.
Iqbal et al., on pp. 2-4 (Molecular Biology International, 2014, Article ID 852748, 9 pages.
Iwaki et al. Btk Plays a Crucial Role in the Amplification of FceRI-mediated Mast Cell Activation by Kit. J. Biol. Chem. 280(48):40261-40270 (Dec. 2, 2005).
Janssen Biotech, Inc. An open label treatment use protocol for ibrutinib in subjects with relapsed or refractory mantel cell lymphoma. In: ClinicalTrials.gov [Internet]. Bethesda (MD): National Library of Medicine (US). Apr. 6, 2013—[cited Nov. 22, 2013]. Available from: http://clinicaltrials.gov/ct2/show/NCT01833039 NLM Identifier: NCT01833039.
Janssen Pharmaceutical K.K. A study to evaluate the Bruton's tyrosine kinase (Btk) inhibitor PCI-32765 in patients with recurrent mature B-cell neoplasms. In: ClinicalTrials.gov [Internet]. Bethesda (MD): National Library of Medicine (US). Oct. 9, 2012—[cited Nov. 22, 2013]. Available from: http://clinicaltrials.gov/ct2/show/NCT01704963 NLM Identifier: NCT01704963.
Janssen Pharmaceutical K.K. Study of the Bruton's Tyrosine Kinase (BTK) Inhibitor Ibrutinib in Participants With Relapsed or Refractory Mantle Cell Lymphoma. In: ClinicalTrials.gov [Internet]. Bethesda (MD): National Library of Medicine (US). Jun. 19, 2014—[cited Feb. 5, 2015] Available from: https://clinicaltrial.gov/ct2/show/NCT02169180?term=NCT02169180 NLM Identifier: NCT02169180.
Janssen Research & Development, LLC. A Study to Evaluate the Effects of Ibrutinib on Cardiac Repolarization in Healthy Participants. In: ClinicalTrials.gov [Internet]. Bethesda (MD): National

(56) References Cited

OTHER PUBLICATIONS

Library of Medicine (US). Oct. 20, 2014 [cited Feb. 5, 2015] Available from: https://clinicaltrial.gov/ct2/show/NCT02271438?term=NCT02271438 NLM Identifier: NCT02271438.

Janssen Research & Development, LLC. Pharmacokinetic and Pharmacodynamic Study to Evaluate Safety and Efficacy of the Combination of Ibrutinib With Nivolumab in Participants With Hematologic Malignancies. In: ClinicalTrials.gov [Internet]. Bethesda (MD): National Library of Medicine (US). Dec. 30, 2014 [cited Feb. 5, 2015] Available from: https://clinicaltrial.gov/ct2/show/NCT02329847?term=NCT02329847 NLM Identifier: NCT02329847.

Janssen Research and Development, LLC. A long-term extension study of PCI-32765 (Ibrutinib). In: ClinicalTrials.gov [Internet]. Bethesda (MD): National Library of Medicine (US). Mar. 4, 2013—[cited Nov. 22, 2013]. Available from: http://clinicaltrials.gov/ct2/show/NCT01804686 NLM Identifier: NCT01804686.

Janssen Research and Development, LLC. A pharmacokinetic study in healthy participants to assess the pharmacokinetics and safety of a supratherapeutic dose of PCI-32765 (Ibrutinib) capsule and solution formulations administered with food. In: ClinicalTrials.gov [Internet]. Bethesda (MD): National Library of Medicine (US). Aug. 19, 2013—[cited Nov. 22, 2013]. Available from: http://clinicaltrials.gov/ct2/show/NCT01969266 NLM Identifier: NCT01969266.

Janssen Research and Development, LLC. A study combining Ibrutinib with rituximab, cyclophosphamide, doxorubicin, vincristine, and prednisone in patients with CD20-positive B-cell non Hodgkin lymphoma. In: ClinicalTrials.gov [Internet]. Bethesda (MD): National Library of Medicine (US). Mar. 30, 2012—[cited Nov. 22, 2013]. Available from: http://clinicaltrials.gov/ct2/show/NCT01569750 NLM Identifier: NCT01569750.

Janssen Research and Development, LLC. A study of ibrutinib in combination with bendamustine and rituximab in patients with relapsed or refractory chronic lymphocytic leukemia or small lymphocytic lymphoma. In: ClinicalTrials.gov [Internet]. Bethesda (MD): National Library of Medicine (US). May 15, 2012—[cited Nov. 22, 2013]. Available from: http://clinicaltrials.gov/ct2/show/NCT01611090 NLM Identifier: NCT01611090.

Janssen Research and Development, LLC. A study of PCI-32765 (Ibrutinib) in combination with either bendamustine and rituximab or rituximab, cyclophosphamide, doxorubicin, vincristine, and prednisone in patients with previously treated indolent non-Hodgkin lymphoma. In: ClinicalTrials.gov [Internet]. Bethesda (MD): National Library of Medicine (US). Oct. 28, 2013—[cited Nov. 22, 2013]. Available from: http://clinicaltrials.gov/ct2/show/NCT01974440 NLM Identifier: NCT01974440.

Janssen Research and Development, LLC. A study of PCI-32765 (Ibrutinib) in patients with refractory follicular lymphoma. In: ClinicalTrials.gov [Internet]. Bethesda (MD): National Library of Medicine (US). Jan. 25, 2013—[cited Nov. 22, 2013]. Available from: http://clinicaltrials.gov/ct2/show/NCT01779791 NLM Identifier: NCT01779791.

Janssen Research and Development, LLC. A study of the Bruton's tyrosine kinase inhibitor ibrutinib given in combination with bendamustine and rituximab in patients with newly diagnosed mantel cell lymphoma. In: ClinicalTrials.gov [Internet]. Bethesda (MD): National Library of Medicine (US). Jan. 24, 2013—[cited Nov. 22, 2013]. Available from: http://clinicaltrials.gov/ct2/show/NCT01776840 NLM Identifier: NCT01776840.

Janssen Research and Development, LLC. A study of the Bruton's tyrosine kinase inhibitor PCI-32765 (Ibrutinib) versus rituximab in patients with relapsed or refractory chronic lymphocytic leukemia/small lymphocytic lymphoma. In: ClinicalTrials.gov [Internet]. Bethesda (MD): National Library of Medicine (US). Oct. 25, 2013—[cited Nov. 22, 2013]. Available from: http://clinicaltrials.gov/ct2/show/NCT01973387 NLM Identifier: NCT01973387.

Janssen Research and Development, LLC. A study on the Bruton's tyrosine kinase inhibitor, PCI-32765 (Ibrutinib), in combination with rituximab, cyclophosphamide, doxorubicin, vincristine, and prednisone in patients with newly diagnosed non-germinal center B-cell subtype of diffuse large B-cell lymphoma. In: ClinicalTrials.gov [Internet]. Bethesda (MD): National Library of Medicine (US). May 14, 2013—[cited Nov. 22, 2013]. Available from: http://clinicaltrials.gov/ct2/show/NCT01855750 NLM Identifier: NCT01855750.

Janssen Research and Development, LLC. A study to assess the absolute bioavailability of Oral PCI-32765 and the effect of grapefruit juice on the bioavailability of PCI-32765 in healthy participants. In: ClinicalTrials.gov [Internet]. Bethesda (MD): National Library of Medicine (US). May 28, 2013—[cited Nov. 22, 2013]. Available from: http://clinicaltrials.gov/ct2/show/study/NCT01866033 NLM Identifier: NCT01866033.

Janssen Research and Development, LLC. A study to assess the effect of ketoconazole on the pharmacokinetics of ibrutinib in healthy participants. In: ClinicalTrials.gov [Internet]. Bethesda (MD): National Library of Medicine (US). Jun. 18, 2012—[cited Nov. 22, 2013]. Available from: http://clinicaltrials.gov/ct2/show/NCT01626651 NLM Identifier: NCT01626651.

Janssen Research and Development, LLC. A study to assess the effect of rifampin on the pharmacokinetics of PCI-32765 in healthy participants. In: ClinicalTrials.gov [Internet]. Bethesda (MD): National Library of Medicine (US). Jan. 4, 2013—[cited Nov. 22, 2013]. Available from: http://clinicaltrials.gov/ct2/show/NCT01763021 NLM Identifier: NCT01763021.

Janssen Research and Development, LLC. A study to determine the absorption, metabolism, and routes of excretion of (14C) radiolabeled ibrutinib in healthy male participants. In: ClinicalTrials.gov [Internet]. Bethesda (MD): National Library of Medicine (US). Aug. 9, 2012—[cited Nov. 22, 2013]. Available from: http://clinicaltrials.gov/ct2/show/NCT01674322 NLM Identifier: NCT01674322.

Janssen Research and Development, LLC. A study to determine the effect of food on the pharmacokinetics of PCI-32765. In: ClinicalTrials.gov [Internet]. Bethesda (MD): National Library of Medicine (US). Mar. 4, 2013—[cited Nov. 22, 2013]. Available from: http://clinicaltrials.gov/ct2/show/NCT01820936 NLM Identifier: NCT01820936.

Janssen Research and Development, LLC. A study to evaluate the efficacy and safety of ibrutinib, in patients with mantel cell lymphoma who progress after bortezomib therapy. In: ClinicalTrials.gov [Internet]. Bethesda (MD): National Library of Medicine (US). May 14, 2012—[cited Nov. 22, 2013]. Available from: http://clinicaltrials.gov/ct2/show/NCT01599949 NLM Identifier: NCT01599949.

Janssen Research and Development, LLC. A study to evaluate the pharmacokinetics of PCI-32765 in participants with varying degrees of hepatic impairment. In: ClinicalTrials.gov [Internet]. Bethesda (MD): National Library of Medicine (US). Jan. 9, 2013—[cited Nov. 22, 2013]. Available from: http://clinicaltrials.gov/ct2/show/NCT01767948 NLM Identifier: NCT01767948.

Janssen Research and Development, LLC. Study of ibrutinib (a Bruton's tyrosine kinase inhibitor), versus temsirolimus in patients with relapsed or refractory mantel cell lymphoma who have received at least one prior therapy. In: ClinicalTrials.gov [Internet]. Bethesda (MD): National Library of Medicine (US). Jul. 18, 2012 [cited Nov. 22, 2013]. Available from: http://clinicaltrials.gov/ct2/show/NCT01646021 NLM Identifier: NCT01646021.

Jefferies et al., "Bruton's tyrosine kinase is a toll/interleukin-1 receptor domain-binding protein that participates in nuclear factor kB activation by toll-like receptor 4," J Biol Chem, 278:26258-64 (2003).

Kamb, "What's wrong with our cancer models?" Nat Rev Drug Discov, 4: 161-165 (2005).

Kawakami et al. Terreic acid, a quinone epoxide inhibitor of Bruton's tyrosine kinase. PNAS USA 96:2227-2232 (1999).

Kim et al. HRG-β1-driven ErbB3 signaling induces epithelial-mesenchymal transition in breast cancer cells. BMC Cancer. Aug. 12, 2013;13:383. doi: 10.1186/1471-2407-13-383.

Kola et al., "Can the pharmaceutical industry reduce attrition rates?" Nat Rev Drug Discov, 3: 711-715 (2004).

(56) References Cited

OTHER PUBLICATIONS

Korade-Mirnics et al. Src kinase-mediated signaling in leukocytes. J. Leukoc. Bio., 68(5):603-613 (Nov. 2000).
Kozaki et al. Development of a Bruton's tyrosine kinase (Btk) inhibitor—ONO-WG-307, a potential treatment for B-cell malignancies. 53rd American Society of Hematology Annual Meeting and Exposition, San Diego, CA, Poster #857 (Dec. 10-13, 2011).
Kuglstatter et al. Insights into the conformational flexibility of Bruton's tyrosine kinase from multiple ligand complex structures. Protein Science 20(2):428-436 (2011) [E-pub Dec. 17, 2010].
Kuppers. Mechanisms of B-cell lymphoma pathogenesis. Nature Reviews/Cancer 5:251-262 (2005).
Kurosaki. Functional dissection of BCR signaling pathways. Curr. Op. Imm. 12:276-281 (2000).
Kushner et al. Pharmacological uses and perspective of heavy water and deuterated compounds. Canadian Journal of Physiology and Pharmacology 77(2):79-88 (1999).
Leaf, "Why are we losing the war on cancer (and how to win it)," Health Administrator, XVII(1): 172-183 (2005).
Li et al. Activation of Bruton's Tyrosine Kinase (BTK) by a Point Mutation in Its Pleckstrin Homology (PH) domain. Immunity 2:451-460 (1995).
Lichtman. Battling the hematological malignancies: The 200 years' war. The Oncologist 13:126-138 (2008).
Liu et al. Structural Basis for selective inhibition of Src family kinases by PPI. Chemistry and Biology 6:671-678, in particular table 1, p. 671 (1999).
Lopez et al. Combining PCI-24781, a Novel Histone Deacetylase Inhibitor, with Chemotherapy for the Treatment of Soft Tissue Sarcoma. Clin Cancer Res 15:1774-1775, 3472-3483 (2009).
Lossos. Molecular Pathogenesis of Diffuse Large B-Cell Lymphoma. J. Clin. Oncol. 23(26):6351-6357 (Sep. 10, 2005).
Lou et al. Bruton's tyrosine kinase inhibitors: approaches to potent and selective inhibition, preclinical and clinical evaluation for inflammatory diseases and B cell malignancies. J Med Chem. May 24, 2012;55(10):4539-50 Publication Date (Web): Mar. 6, 2012.
Luskova et al. Modulation of the Fce Receptor I Signaling by Tyrosine Kinase Inhibitors: Search for Therapeutic Targets of Inflammatory and Allergy Diseases. Curr. Pharmaceutical Design 10:1727-1737 (2004).
M.D. Anderson Cancer Center. A Phase I/II Study of Ibrutinib in Previously Treated Epidermal Growth Factor Receptor (EGFR) Mutant Non-Small Cell Lung Cancer. In: ClinicalTrials.gov [Internet]. Bethesda (MD): National Library of Medicine (US). Dec. 17, 2014 [cited Feb. 5, 2015] Available from: https://clinicaltrial.gov/ct2/show/NCT02321540?term=NCT02321540 NLM Identifier: NCT02321540.
M.D. Anderson Cancer Center. A Phase I/II Trial of PCI-32765 (BTK Inhibitor) in Combination With Carfilzomib in Relapse/Refractory Mantle Cell Lymphoma. In: ClinicalTrials.gov [Internet]. Bethesda (MD): National Library of Medicine (US). Oct. 16, 2014 [cited Feb. 5, 2015] Available from: https://clinicaltrial.gov/ct2/show/NCT02269085?term=NCT02269085 NLM Identifier: NCT02269085.
M.D. Anderson Cancer Center. Ibrutinib Post Stem Cell Transplantation (SCT) in Double-Hit B-Cell Lymphoma. In: ClinicalTrials.gov [Internet]. Bethesda (MD): National Library of Medicine (US). Oct. 21, 2014 [cited Feb. 5, 2015] Available from: https://clinicaltrial.gov/ct2/show/NCT02272666?term=NCT02272686 NLM Identifier: NCT02272686.
M.D. Anderson Cancer Center. Ibrutinib versus ibrutinib + rituximab (i vs iR) in patients with relapsed chronic lymphocytic leukemia (CLL). In: ClinicalTrials.gov [Internet]. Bethesda (MD): National Library of Medicine (US). Dec. 5, 2013—[cited Apr. 15, 2014]. Available from: http://clinicaltrials.gov/ct2/show/NCT02007044 NLM Identifier: NCT02007044.
M.D. Anderson Cancer Center. Phase 2 ibrutinib + rituximab in relapsed/refractory mantel cell lymphoma (R/R MCL). In: ClinicalTrials.gov [Internet]. Bethesda (MD): National Library of Medicine (US). Jun. 14, 2013—[cited Nov. 22, 2013]. Available from: http://clinicaltrials.gov/ct2/show/NCT01880567 NLM Identifier: NCT01880567.
M.D. Anderson Cancer Center. Phase 2 study of the combination of Bruton's tyrosine kinase inhibitor PCI-32765 and rituximab in high-risk chronic lymphocytic leukemia and small lymphocytic lymphoma patients. In: ClinicalTrials.gov [Internet]. Bethesda (MD): National Library of Medicine (US). Jan. 25, 2012—[cited Nov. 22, 2013]. Available from: http://clinicaltrials.gov/ct2/show/NCT01520519 NLM Identifier: NCT01520519.
M.D. Anderson Cancer Center. Pilot study to determine effects of the Btk inhibitor PCI-32765 on leukemia cell kinetics and trafficking, using heavy water labeling in subjects with CLL and SLL. In: ClinicalTrials.gov [Internet]. Bethesda (MD): National Library of Medicine (US). Dec. 13, 2012—[cited Nov. 22, 2013]. Available from: http://clinicaltrials.gov/ct2/show/NCT01752426 NLM Identifier: NCT01752426.
Maddocks et al. Ibrutinib in B-cell lymphomas. Current Treatment Options in Oncology 15:226-237 (2014) (Epub: Feb. 1, 2014).
Mahajan et al. Rational Design and Synthesis of a Novel Anti-leukemic Agent Targeting Bruton's Tyrosine Kinase (BTK), LFM-A13 [a-Cyano-β-Methyl-N-(2,5-Dibromophenyl)Propenamide]. J. of Biol. Chem. 274(14):9587-9599 (1999).
Mallis et al. Structural characterization of a proline-driven conformational switch within the Itk SH2 domain. Nat. Struct. Biol., 9(12):900-905 (2002).
Mangla et al., "Pleiotropic consequences of Bruton tyrosine kinase deficiency in myeloid lineages lead to poor inflammatory responses," Blood, 104(4):1191-1197 (2004).
Marina et al. Biology and Therapeutic Advances for Pediatric Osteosarcoma. The Oncologist 9:422-441 (2004).
Memorial Sloan-Kettering Cancer Center. Bruton's Tyrosine Kinase (BTK) Inhibitor, Ibrutinib, in Patients With Refractory/Recurrent Primary Central Nervous System Lymphoma (PCNSL) and Refractory/Recurrent Secondary Central Nervous System Lymphoma (SCNSL). In: ClinicalTrials.gov [Internet]. Bethesda (MD): National Library of Medicine (US). Dec. 9, 2014 [cited Feb. 5, 2015] Available from: https://clinicaltrial.gov/ct2/show/NCT02315326?term=NCT02315326 NLM Identifier: NCT02315326.
Mendel et al. In vivo antitumor activity of SU11248, a novel tyrosine kinase inhibitor targeting vascular endothelial growth factor and platelet-derived growth factor receptors: determination of a pharmacokinetic/pharmacodynamic relationship. Clin Cancer Res 9(1):327-337 (2003).
Merged Markush Service Search, Jun. 27, 2005.
Middendorp et al. Function of Bruton's Tyrosine Kinase during B Cell Development is Partially Independent of its Catalytic Activity. J Immunol 171:5988-5996 (2003).
Middendorp et al. Tumor Suppressor Function of Bruton Tyrosine Kinase is Independent of its catalytic activity. Blood 105(1):259-261 (2005).
Montero et al. Neuregulins and cancer Clin Cancer Res. Jun. 1, 2008;14(11):3237-41. doi: 10.1158/1078-0432.CCR-07-5133.
Mukoyama et al., "Preparation of imidazol [1,5-a]pyrazine derivatives, pharmaceutical compositions containing them, and their uses for prevention or treatment of protein tyrosine kinase-related diseases," retrieved from STN Database Accession No. 2005:299462 Patent No. JP2005089352, Abstract (2005).
National Cancer Institute (NCI). A multicenter phase 2 study of the Bruton's tyrosine kinase inhibitor PCI-32765 for treatment of relapsed hairy cell leukemia. In: ClinicalTrials.gov [Internet]. Bethesda (MD): National Library of Medicine (US). Nov. 2, 2013— [cited Nov. 22, 2013]. Available from: http://clinicaltrials.gov/ct2/show/NCT01981512 NLM Identifier: NCT01981512.
National Cancer Institute (NCI). Ibrutinib and rituximab compared with fludarabine phosphate, cyclophosphamide, and rituximab in treating patients with untreated chronic lymphocytic leukemia or small lymphocytic lymphoma. In: ClinicalTrials.gov [Internet]. Bethesda (MD): National Library of Medicine (US). Jan. 27, 2014—[cited Apr . 15, 2014]. Available from: http://clinicaltrials.gov/ct2/show/NCT02048813 NLM Identifier: NCT02048813.

(56) References Cited

OTHER PUBLICATIONS

National Cancer Institute (NCI). Ibrutinib in treating patients with relapsed hairy cell leukemia. In: ClinicalTrials.gov [Internet]. Bethesda (MD): National Library of Medicine (US). Apr. 24, 2013—[cited Nov. 22, 2013]. Available from: http://clinicaltrials.gov/ct2/show/NCT01841723 NLM Identifier: NCT01641723.
National Cancer Institute (NCI). Ibrutinib in treating patients with relapsed or refractory follicular lymphoma. In: ClinicalTrials.gov [Internet]. Bethesda (MD): National Library of Medicine (US). May 6, 2013—[cited Nov. 22, 2013]. Available from: http://clinicaltrials.gov/ct2/show/NCT01849263 NLM Identifier: NCT01849263.
National Cancer Institute (NCI). Lenalidomide and ibrutinib in treating patients with relapsed or refractory B-Cell non-Hodgkin lymphoma. In: ClinicalTrials.gov [Internet]. Bethesda (MD): National Library of Medicine (US). Sep. 27, 2013—[cited Nov. 22, 2013]. Available from: http://clinicaltrials.gov/ct2/show/NCT01955499 NLM Identifier: NCT01955499.
National Cancer Institute (NCI). Rituximab and bendamustine hydrochloride, riluximab and ibrutinib, or ibrutinib alone in treating older patients with previously untreated chronic lymphocytic leukemia. In: ClinicalTrials.gov [Internet]. Bethesda (MD): National Library of Medicine (US). Jun. 24, 2013—[cited Nov. 22, 2013]. Available from: http://clinicaltrials.gov/ct2/show/NCT01886872 NLM Identifier: NCT01886872.
National Cancer Institute (NCI). Rituximab, lenalidomide, and ibrutinib in treating patients with previously untreated stage II-IV follicular lymphoma. In: ClinicalTrials.gov [Internet]. Bethesda (MD): National Library of Medicine (US). Apr. 9, 2013—[cited Nov. 22, 2013]. Available from: http://clinicaltrials.gov/ct2/show/NCT01829568 NLM Identifier: NCT01829568.
National Cancer Institute. Ibrutinib and Combination Chemotherapy in Treating Patients With Relapsed or Refractory Diffuse Large B-Cell Lymphoma. In: ClinicalTrials.gov [Internet]. Bethesda (MD): National Library of Medicine (US). Jul. 16, 2014 [cited Feb. 5, 2015] Available from: https://clinicaltrial.gov/ct2/show/NCT02219737?term=NCT02219737 NLM Identifier: NCT02219737.
National Cancer Institute. Ibrutinib and Palbociclib Isethionate in Treating Patients With Previously Treated Mantle Cell Lymphoma. In: ClinicalTrials.gov [Internet]. Bethesda (MD): National Library of Medicine (US). Jun. 9, 2014—[cited Feb. 5, 2015] Available from: https://clinicaltrial.gov/ct2/show/NCT02159755?term=NCT02159755 NLM Identifier: NCT02159755.
National Cancer Institute. Ibrutinib in Treating Patients With Relapsed or Refractory B-cell Acute Lymphoblastic Leukemia. In: ClinicalTrials.gov [Internet]. Bethesda (MD): National Library of Medicine (US). Apr. 30, 2014 [cited Feb. 5, 2015] Available from: https://clinicaltrial.gov/ct2/show/NCT02129062?term=NCT02129062 NLM Identifier: NCT02129062.
National Cancer Institute. Ibrutinib in Treating Relapsed or Refractory B-cell Non-Hodgkin Lymphoma in Patients With HIV infection. In: ClinicalTrials.gov [Internet]. Bethesda (MD): National Library of Medicine (US). Apr. 7, 2014 [ cited Feb. 5, 2015]. Available from: https://clinicaltrial.gov/ct2/show/NCT02109224?term=NCT02109224. NLM Identifier: NCT02109224.
National Cancer Institute. Lenalidomide, Ibrutinib, and Rituximab in Treating Patients With Relapsed or Refractory Chronic Lymphocytic Leukemia or Small Lymphocytic Lymphoma. In: ClinicalTrials.gov [Internet]. Bethesda (MD): National Library of Medicine (US). May 30, 2014 [cited Feb. 15, 2015] Available from: https://clinicaltrial.gov/ct2/show/NCT02160015?term=NCT02160015 NLM Identifier: NCT02160015.
National Cancer Institute. Phase 1 Study of Ibrutinib and Immuno-Chemotherapy Using Dose-Adjusted-Temozolomide, Etoposide, Doxil, Dexamethasone, Ibrutinib,Rituximab (DA-TEDDI-R) in Primary CNS Lymphoma. In: ClinicalTrials.gov [Internet]. Bethesda (MD): National Library of Medicine (US). Jul. 29, 2014 [cited Feb. 5, 2015] Available from: https://clinicaltrial.gov/ct2/show/NCT02203526?term=NCT02203526 NLM Identifier: NCT02203526.
National Center Institute (NCI). Lenalidomide and Ibrutinib in treating patients with relapsed or refractory chronic lymphocytic leukemia or small lymphocytic lymphoma. In: ClinicalTrials.gov [Internet]. Bethesda (MD): National Library of Medicine (US). Jun. 24, 2013—[cited Nov. 22, 2013]. Available from: http://clinicaltrials.gov/ct2/show/NCT01886859 NLM Identifier: NCT01886859.
National Heart, Lung, and Blood Institute (NHLBI). PCI-32765 for special cases of chronic lymphocytic leukemia or small lymphocytic lymphoma. In: ClinicalTrials.gov [Internet]. Bethesda (MD): National Library of Medicine (US). Dec. 22, 2011—[cited Nov. 22, 2013]. Available from: http://clinicaltrials.gov/ct2/show/NCT01500733 NLM Identifier: NCT01500733.
Neidle, "Clinical Trial Design," Cancer Drug Design and Discovery, ch. 18.3.2, pp. 431 (2008).
Niiro et al. Regulation of B-Cell Fate by Antigen-Receptor Signals. Nature Reviews 2:945-956 (2002).
Nisitani et al. In situ detection of activated Bruton's tyrosine kinase in the Ig signaling complex by phosphopeptide-specific monoclonal antibodies. PNAS USA 96:2221-2226 (1999).
Nogrady (1985) Medicinal Chemistry A Biochemical Approach, Oxford University Press, New York, pp. 388-394.
Northwestern University. Ibrutinib After Intensive Induction in Treating Patients With Previously Untreated Mantle Cell Lymphoma. In: ClinicalTrials.gov [Internet]. Bethesda (MD): National Library of Medicine (US). Sep. 12, 2014 [cited Feb. 2-15 5] Available from: https://clinicaltrial.gov/ct2/show/NCT02242097?term=NCT02242097 NLM Identifier: NCT02242097.
Notification of Office Action for Eurasian Application No. EA200901313 dated Oct. 31, 2011.
O'Brien et al. Combination of the Bruton's tyrosine kinase (BTK) inhibitor PCI-32765 with bendamustine (B)/rituximan ®(BR) in patients (pts) with relapsed/refractory (R/R) chronic lymphocytic leukemia (CLL): Interm results of phase Ib/II study. J Clin Onc. 2012. Supp. Abstract 6515.
Ohio State University Comprehensive Cancer Center. PCI-32765 (Ibrutinib) in treating patients with relapsed or refractory chronic lymphocytic leukemia, small lymphocytic lymphoma, or B-cell prolymphocytic leukemia. In: ClinicalTrials.gov [Internet]. Bethesda (MD): National Library of Medicine (US). Apr. 23, 2012—[cited Nov. 22, 2013]. Available from: http://clinicaltrials.gov/ct2/show/NCT01589302 NLM Identifier: NCT01589302.
Ohio State University Comprehensive Cancer Center. Rituxan/Bendamustine/PCI-32765 in relapsed DLBCL, MCL, or indolent non-Hodgkin's lymphoma. In: ClinicalTrials.gov [Internet]. Bethesda (MD): National Library of Medicine (US). Nov. 1, 2011—[cited Feb. 6, 2014]. Available from: http://clinicaltrials.gov/ct2/show/NCT01479842 NLM Identifier: NCT01479842.
Oligino et al. Targeting B cells for the treatment of rheumatoid arthritis. Arthritis Res. Ther., 5(Suppl.4):S7-S11 (2002).
Ou. Second-generation irreversible epidermal growth factor receptor (EGFR) tyrosine kinase inhibitors (TKIs): A better mousetrap? A review of the clinical evidence. Crit Rev Onc/Hemat. 2012;83(3):407-421.
Pagel et al., "Induction of apoptosis using inhibitors of lysophosphatidic acid acyltransferase-beta and anti-CD20 monoclonal antibodies for treatment of human non-Hodgkin's lymphomas," Clin Cancer Res, 11(13):4857-4866 (2005).
Pan et al., "Discovery of selective irreversible inhibitors for Bruton's tyrosine kinase," ChemMedChem, 2:58-61 (2007).
Partial European Search Report for European Application No. EP 12172842.2 dated Jan. 24, 2013.
Peterson et al. Prolonged single-agent versus combination chemotherapy in indolent follicular lymphomas: a study of the cancer and leukemia group. Br. J. Clin. Oncol., 21(1):5-15 (Jan. 1, 2003).
Pharmacyclics, Inc. A Multi-Center Study of Ibrutinib in Combination With Obinutuzumab Versus Chlorambucil in Combination With Obinutuzumab in Patients With Treatment naïve CLL or SLL. In: ClinicalTrials.gov [Internet]. Bethesda (MD): National Library

(56) References Cited

OTHER PUBLICATIONS of Medicine (US). Oct. 1, 2014 [cited Feb. 5, 2015] Available from: https://clinicaltrial.gov/ct2/show/NCT02264574?term=NCT02264574 NLM Identifier: NCT02264574.
Pharmacyclics, Inc. A multicenter phase 2 study of PCI-32765 (Ibrutinib) in patients with relapsed or refractory chronic lymphocytic leukemia (CLL) or small lymphocytic lymphoma (SLL) with 17p deletion. In: ClinicalTrials.gov [Internet]. Bethesda (MD): National Library of Medicine (US). Dec. 3, 2012—[cited Nov. 22, 2013]. Available from: http://clinicaltrials.gov/ct2/show/NCT01744691 NLM Identifier: NCT01744691.
Pharmacyclics, Inc. A multicenter, open-label, phase 3 study of the Bruton's tyrosine kinase inhibitor PCI-32765 versus chlorambucil in patients 65 years or older with treatment-naive chronic lymphocytic leukemia or small lymphocytic lymphoma (RESONATE-2). In: ClinicalTrials.gov [Internet]. Bethesda (MD): National Library of Medicine (US). Oct. 29, 2012—[cited Nov. 22, 2013]. Available from: http://clinicaltrials.gov/ct2/show/NCT01722487 NLM Identifier: NCT01722487.
Pharmacyclics, Inc. A phase 3 study of ibrutinib (PCI-32765) versus ofatumumab in patients with relapsed or refractory chronic lymphocytic leukemia (RESONATE). In: ClinicalTrials.gov [Internet]. Bethesda (MD): National Library of Medicine (US). Apr. 11, 2012—[cited Nov. 22, 2013]. Available from: http://clinicaltrials.gov/ct2/show/NCT01578707 NLM Identifier: NCT01578707.
Pharmacyclics, Inc. An open-label extension study in patients 65 years or older with chronic lymphocytic leukemia (CLL) or small lymphocytic lymphoma (SLL) who participated in study PCYC-115-CA (PCI-32765 versus chlorambucil). In: ClinicalTrials.gov [Internet]. Bethesda (MD): National Library of Medicine (US). Nov. 2, 2012—[cited Nov. 22, 2013]. Available from: http://clinicaltrials.gov/ct2/show/NCT01724346 NLM Identifier: NCT01724346.
Pharmacyclics, Inc. Efficacy and safety study of PCI-32765 combined with ofatumumab in CLL (PCYC-1109-CA). In: ClinicalTrials.gov [Internet]. Bethesda (MD): National Library of Medicine (US). Oct. 7, 2010—[cited Nov. 22, 2013]. Available from: http://clinicaltrials.gov/ct2/show/NCT01217749 NLM Identifier: NCT01217749.
Pharmacyclics, Inc. Ibrutinib and Lenalidomide With Dose Adjusted EPOCH-R in Subjects With Relapsed/Refractory Diffuse Large B-cell Lymphoma. In: ClinicalTrials.gov [Internet]. Bethesda (MD): National Library of Medicine (US). May 12, 2014 [cited Feb. 5, 2015] Available from: https://clinicaltrial.gov/ct2/show/NCT02142049?term=NCT02142049 NLM Identifier: NCT02142049.
Pharmacyclics, Inc. Ibrutinib in combination with lenalidomide, with and without rituximab in participants with relapsed or refractory diffuse large B-cell lymphoma. in: ClinicalTrials.gov [Internet]. Bethesda (MD): National Library of Medicine (US). Feb. 10, 2014—[cited Apr. 15, 2014]. Available from: http://clinicaltrials.gov/ct2/show/NCT02077166 NLM Identifier: NCT02077166.
Pharmacyclics, Inc. Ibrutinib Wth Rituximab in Previously Treated Adults With Waldenstrom's Macroglobulinemia. in: ClinicalTrials.gov [Internet]. Bethesda (MD): National Library of Medicine (US). Jun. 9, 2014 [cited Feb. 5, 2015] Available from: https://clinicaltrial.gov/ct2/show/NCT02165397?term=NCT02165397 NLM Identifier: NCT02165397.
Pharmacyclics, Inc. Safety and efficacy of PCI-32765 in subjects with relapsed/refractory mantel cell lymphoma (MCL). In: ClinicalTrials.gov [Internet]. Bethesda (MD): National Library of Medicine (US). Oct. 18, 2010—[cited Nov. 22, 2013]. Available from: http://clinicaltrials.gov/ct2/show/NCT01236391 NLM Identifier: NCT01236391.
Pharmacyclics, Inc. Safety and efficacy study of Bruton's tyrosine kinase inhibitor in subjects with relapsed or refractory diffuse large B-cell lymphoma. In: ClinicalTrials.gov [Internet]. Bethesda (MD): National Library of Medicine (US). Feb. 2, 2011—[cited Nov. 22, 2013]. Available from: http://clinicaltrials.gov/ct2/show/NCT01325701 NLM Identifier: NCT01325701.
Pharmacyclics, Inc. Safety and tolerability study of PCI-32765 combined with fludarabine/cyclophosphamide/rituximab (FCR) and bendamustine/rituximab (BR) in chronic lymphocytic leukemia (CLL). In: ClinicalTrials.gov [Internet]. Bethesda (MD): National Library of Medicine (US). Feb. 2, 2011—[cited Nov. 22, 2013]. Available from: http://clinicaltrials.gov/ct2/show/NCT01292135 NLM Identifier: NCT01292135.
Pharmacyclics, Inc. Safety and tolerability study of PCI-32765 in B Cell lymphoma and chronic lymphocytic leukemia. In: ClinicalTrials.gov [Internet]. Bethesda (MD): National Library of Medicine (US). Apr. 19, 2010—[cited Nov. 25, 2013]. Available from: http://clinicaltrials.gov/ct2/show/NCT01109069 NLM Identifier: NCT01109069.
Pharmacyclics, Inc. Safety of PCI-32765 in chronic lymphocytic leukemia. In: ClinicalTrials.gov [Internet]. Bethesda (MD): National Library of Medicine (US). Apr. 13, 2010—[cited Nov. 22, 2013]. Available from: http://clinicaltrials.gov/ct2/show/NCT01105247 NLM Identifier: NCT01105247.
Pharmacyclics, Inc. Study of the Bruton's tyrosine kinase inhibitor in combination with carfilzomib (Kyprolis), in subjects with relapsed or relapsed and refractory multiple myeloma. In: ClinicalTrials.gov [Internet]. Bethesda (MD): National Library of Medicine (US). Sep. 27, 2013—[cited Nov. 22, 2013]. Available from: http://clinicaltrials.gov/ct2/show/NCT01962792 NLM Identifier: NCT01962792.
Pharmacyclics, Inc. Study of the Bruton's tyrosine kinase inhibitor in combination with rituximab in previously untreated subjects with follicular lymphoma. In: ClinicalTrials.gov [Internet]. Bethesda (MD): National Library of Medicine (US). Oct. 24, 2013—[cited Nov. 22, 2013]. Available from: http://clinicaltrials.gov/ct2/show/NCT01980654 NLM Identifier: NCT01980654.
Pharmacyclics, Inc. Study of the Bruton's Tyrosine Kinase Inhibitor in Subjects With Chronic Graft Versus Host Disease. In: ClinicalTrials.gov [Internet]. Bethesda (MD): National Library of Medicine (US). Jul. 11, 2014 [cited Feb. 5, 2015] Available from: https://clinicaltrial.gov/ct2/show/NCT02195869?term=NCT02195869 NLM Identifier: NCT02195869.
Pharmacyclics, Inc. Study of the Bruton's tyrosine kinase inhibitor in subjects with relapsed or relapsed and refractory multiple myeloma. In: ClinicalTrials.gov [Internet]. Bethesda (MD): National Library of Medicine (US). Nov. 18, 2011—[cited Nov. 22, 2013]. Available from: http://clinicaltrials.gov/ct2/show/NCT01478581 NLM Identifier: NCT01478581.
Pharmacyclics, Inc. Study of the Bruton's tyrosine kinase inhibitor in subjects with relapsed/refractory marginal zone lymphoma. In: ClinicalTrials.gov [Internet]. Bethesda (MD): National Library of Medicine (US). Oct. 29, 2013 [cited Nov. 22, 2013]. Available from: http://clinicaltrials.gov/ct2/show/NCT01980628 NLM Identifier: NCT01980628.
Pharmacyclics, Inc. Study of the safety and tolerability of PCI-32765 in patients with recurrent B cell lymphoma (PCYC-04753). In: ClinicalTrials.gov [Internet]. Bethesda (MD): National Library of Medicine (US). Feb. 20, 2009—[cited Nov. 22, 2013]. Available from: http://clinicaltrials.gov/ct2/show/NCT00849654 NLM Identifier: NCT00849654.
Picci, P. et al., "Osteosarcoma (osteogenic sarcoma)," Orphanet J Rare Dis, 2(6):1-4 (2007).
Pollyea et al., "A phase I dose escalation study of the Btk inhibitor PCI-32765 in relapsed and refractory B cell non-Hodgkin lymphoma and use of a novel fluorescent probe pharmacodynamic assay," 51st ASH Annual Meeting and Exposition, Poster Abstract #3713 (2009).
Ponader et al. The Bruton tyrosine kinase inhibitor PCI-32765 thwarts chronic lymphocytic leukemia cell survival and tissue homing in vitro and in vivo. Blood (Epub Dec. 16, 2011), 119(5):1182-1189 (Feb. 2012).
Powers et al. Irreversible Inhibitors of Serine, Cysteine, and Threonine Proteases. Chem. Rev., 102(12):4639-4750 (2002).
Prakash et al. Chicken sarcoma to human cancers: a lesson in molecular therapeutics. The Ochsner Journal, 7(2):61-64 (Jan. 1, 2007).
PRNewsire "U.S. FDA grants regular (full) approval for IMBRUVICA for two indications," Jul. 28, 2014.

(56) References Cited

OTHER PUBLICATIONS

PRNewswire, "Pharmacyclics, Inc. announces presentation of interim results from phase I trial of its first-in-human Btk inhibitor PCI-32765," Dec. 7, 2009.
PRNewswire, "Update on preclinical finding and development timeline for PCI-45292," Mar. 2, 2011.
Quek et al. A role for Bruton's tyrosine kinase (Btk) in platelet activation by collagen. Curr. Biol. 8(20):1137-1140 (1998).
Rao et al. Inhibition of invasion, angiogenesis, tumor growth, and metastasis by adenovirus-mediated transfer of antisense uPAR and MMP-9 in non-small cell lung cancer cells. Mol Cancer Ther 4(9):1399-1408 (2005).
Ritter et al. Osteosarcoma. Ann. Oncol. 21(Supplement 7):320-325 (2010).
Robak et al. A Targeted Therapy for Protein and Lipid Kinases in Chronic Lymphocytic Leukemia. Curr. Med. Chem. (Epub Jul. 24, 2012), 19(31):5294-5318 (2012).
Robak et al. Tyrosine kinase inhibitors as potential drugs for B-cell lymphoid malignancies and autoimmune disorders. Expert Opin. Investig. Drugs (Epub May 22, 2012), 21(7):921-947 (Jul. 2012).
Roberts et al., "Trends in the risks and benefits to patients with cancer participating in phase 1 clinical trials," JAMA, 292(17): 2130-2140 (2004).
Rushworth et al. BTK inhibitor ibrutinib is cytotoxic to myeloma and potently enhances bortezomib and lenalidomide activities through NF-κB. Cell Signal (Epub Sep. 11, 2012), 25(1):106-112 (Jan. 2013).
Sada et al. Protein-Tyrosine Kinases and Adaptor Proteins in FceRI-Mediated Signaling in Mast Cells. Curr. Mol. Med. 3(1):85-94 (2003).
Saulnier et al., "An efficient method for the synthesis of guanidine prodrugs," Bioorganic and Medicinal Chemistry Letters, vol. 4, p. 1985-90 (1994).
Schaeffer et al. Tec family kinases in lymphocyte signaling and function. Curr. Op. Imm. 12:282-288 (2000).
Schnute et al., "Bruton's tyrosine kinase (Btk)," Anti-Inflammatory Drug Discovery, Ed. J.I. Levin and S. Laufer, (2012), pp. 297-326.
Schwamb et al. B-cell receptor triggers drug sensitivity of primary CLL cells by controlling glucosylation of ceramides. Blood (Epub Aug. 27, 2012), 120(19):3978-3985 (Nov. 2012).
Science Daily Counting tumor cells in blood predicts treatment benefit in prostate cancer. (Jul. 7, 2008), http://www.sciencedaily.com/releases/2008/07/080706083142.htm , last accessed Jul. 23, 2013.
Science Daily, "Drug shows surprising efficacy as treatment for chronic leukemia, mantle cell lymphoma," (Jun. 19, 2013), http://www.sciencedaily.com/releases/2013/06/130619195217.htm, last accessed Jan. 15, 2016.
Science IP CAS Search, Mar. 16, 2006.
Science IP CAS Search, Sep. 5, 2006.
Shaffer et al. Lymphoid malignancies: the dark side of B-cell differentiation. Nature Reviews/Immunology 2:920-932 (2002).
Shah et al. Ibrutinib for the treatment of mantle cell lymphoma. Expert Rev. Hematol. 7(5):521-531 (2014) (Epub Aug. 27, 2014).
Silverman. The Organic Chemistry of Drug Design and Drug Action, Academic Press, Inc., San Diego, pp. 352-401 (1992).
Smaill et al., "Tyrosine kinase inhibitors. 15. 4-(phenylamino)quinazoline and 4-(phenylamino)pyrido[d]pyrimidine acrylamides as irreversible inhibitors of the ATP binding site of the epidermal growth factor receptor," J Med Chem, 42(10):1803-15 (1999).
Smith et al., "The Tec family of cytoplasmic tyrosine kinases: mammalian Btk, Bmx, Itk, Tec, Txk and homologs in other species," BioEssays, 23:436-46 (2001).
Smolen et al. Therapeutic Strategies for Rheumatoid Arthritis. Nature Reviews 2:473-488 (2003).
STN Registry No. 936563-96-1 Ibrutinib. Retrieved from STN Registry Jul. 27, 2015. 1 pg.
Strimbu et al. What are biomarkers? Curr Opin HIV AIDS 5(6):463-466 (2010.

Supplemental European Search Report for European Application No. EP 06850039 dated Feb. 15, 2010.
Supplementary European Search Report for European Application No. EP 14835935 dated Mar. 6, 2017.
TG Therapeutics, Inc. Ublituximab + ibrutinib in select B-cell malignancies. In: ClinicalTrials.gov [Internet]. Bethesda (MD): National Library of Medicine (US). Dec. 11, 2013—[cited Apr. 15, 2014]. Available from: http://clinicaltrials.gov/ct2/show/NCT02013128 NLM Identifier: NCT02013128.
The Lymphoma Academic Research Organisation. Bruton's tyrosine kinase (BTK) inhibition in B-cell lymphomas (BIBLOS). In: ClinicalTrials.gov [Internet]. Bethesda (MD): National Library of Medicine (US). Jan. 31, 2014—[cited Apr. 15, 2014]. Available from: http://clinicaltrials.gov/ct2/show/NCT02055924 NLM Identifier: NCT02055924.
Theil. Structure-aided drug design's next generation. Nature Biotechnol 2:513-519 (2004).
Thurn et al. (Future Oncol. Feb. 2011; 7(2): 263-2830.
Tinmouth et al. Fludarabine in alkylator-resistant follicular non-Hodgkin's lymphoma. Leuk. Lymphoma 41(1-2):137-145 (2001).
Traxler et al., "Use of a pharmacophore model for the design of EGF-R tyrosine kinase inhibitors: 4-(phenylamino)pyrazolo[3,4-d]pyramidines," J Med Chem, 40(22):3601-16 (1997).
Uckun et al. Bruton's Tyrosine Kinase (BTK) as a Dual-Function Regulator of Apoptosis. Biochem. Pharmacology 56:683-691 (1998).
Uckun et al. The Anti-leukemic Bruton's Tyrosin Kinase Inhibitor a-cyano-β-hydroxy-β-mehyl-N-(2,5-dibromophenyl)Propenamide (LFM-A13)Prevents Fatal Thromboembolism. Leuk. Lymphoma 44(9):1569-1577 (2003).
Uckun et al., "Bruton's tyrosine kinase as a molecular target in treatment of leukemias and lymphomas as well as inflammatory disorders and autoimmunity," Expert Opin Ther Pat, 20(11):1-14 (2010).
Uckun et al., "Btk as a mediator of radiation-induced apoptosis in DT-40 lymphoma B cells," Science, 273(5278):1096-100 (1996).
Uckun et al., "In vivo pharmacokinetic features, toxicity profile, and chemosensitizing activity of alpha-cyano-beta-hydroxy-beta-methyl-N-(2,5-dibromophenyl)propenamide (LFM-A13), a novel antileukemic agent targeting Bruton's tyrosine kinase," Clin Cancer Res, 8(5):1224-33 (2002).
University of California, San Diego. A Phase Ib/II Study of Ibrutinib in Combination With GA101—Obinutuzumab in Previously Untreated Chronic Lymphocytic Leukemia (CLL) Patients Over 65 Years of Age or With Comorbidities That Preclude the Use of Chemotherapy Based Treatment. In: ClinicalTrials.gov [Internet]. Bethesda (MD): National Library of Medicine (US). Oct. 30, 2014 [cited Feb. 5, 2015] Available from: https://clinicaltrial.gov/ct2/show/NCT02315768?term=NCT02315768 NLM Identifier: NCT02315768.
Vassilev et al. Bruton's Tyrosine Kinase as an Inhibitor of the Fas/CD95 Death-inducing Signaling Complex. J. Biol. Chem. 274(3):1646-1656 (1999).
Vassilev et al. Therapeutic Potential of Inhibiting Bruton's Tyrosine Kinase, (BTK). Current Pharmaceutical Design 10:1757-1766 (2004).
Vippagunta et al. Crystalline Solids, Advanced Drug Delivery Reviews, 48:3-26 (2001).
Vose. Mantle cell lymphoma: 2012 update on diagnosis, risk-stratification, and clinical management. Am. J. Hematol. 87(6):604-609 (Jun. 2012).
Wang et al. Targeting BTK with ibrutinib in relapsed or refractory mantel-cell lymphoma. N Engl J Med 369(6):507-516 (Aug. 8, 2013).
Wanner et al., "Mammalian Target of Rapamycin Inhibition Induces Cell Cycle Arrest in Diffuse Large B Cell Lymphoma (DLBCL) Cells and Sensitises DLBCL Cells to Rituximab," Brit J Haematol, 134: 475-484 (2006).
Wilkinson et al. Selective tyrosine kinase inhibitors. Expert Opin. Emerging Drugs 5(3):287-297 (2000).
Wilson et al., "The Bruton's tyrosine kinase (BTK) inhibitor, ibrutinib (PCI-32765), has preferential activity in the ABC subtype of relapsed/refractory de novo diffuse large B-cell lymphoma

(56) References Cited

OTHER PUBLICATIONS (DLBCL): interim results of a multicenter, open-label, phase 2 study," Blood 120:Abstract 666 (2012).
Witzens-Harig et al. Current treatment of mantle cell lymphoma: results of a national survey and consensus meeting. Ann Hematol. (Epub Aug. 29, 2012), 91(11)1 765-1772 (Nov. 2012).
Witzig et al. Detection of myeloma cells in the peripheral blood by flow cytometry. Cytometry (Communications in Clinical Cytometry), 26:113-120 (1996).
Witzig et al. Lenalidomide oral monotherapy produces durable responses in relapsed or refractory indolent non-Hodgkin's lymphoma. J. Clin. Oncol. 27:5404-5409 (Epub Oct. 5, 2009).
Wolff (Medicinal Chemistry) summarizes the state of the prodrug art. Wolff, Manfred E. "Burger's Medicinal Chemistry, 5ed, Part 1", John Wiley & Sons, 1995, pp. 975-977.
Wolff. Burger's Medicinal Chemistry and Drug Discovery. 5th Ed. Part 1, pp. 975-977 (1995).
Woyach et al., "Resistance Mechanisms for the Bruton's Tyrosine Kinase Inhibitor Ibrutinib," N Engl J Med, 370(24): 2286-2294 (2014).
Written Opinion for European Application No. EP 10823966.6 dated Dec. 6, 2011.
Yamamoto et al. The Orally Available Spleen Tyrosine Kinase Inhibitor 2-[7-(3,4Dimethoxyphenyl)-imidazo[1,2-c]pyrimidin-5-ylaminol-nicotinamide Dihydrochloride (BAY61-3606) Blocks Antigen-Induced Airway Inflammation in Rodents. J. Pharma. And Exp. Therapeutics 306(3):1174-1181 (2003).
Yang et al. Tyrosine kinase inhibition in diffuse large B-cell lymphoma: molecular basis for antitumor activity and drug resistance of dasatinib. Leukemia 22(9):1755-1766 (2006) [E-pub Jul. 3, 2008].
Yasuhiro et al., "ONO-WG-307, a novel, potent and selective inhibitor of Bruton's tyrosine kinase, in sustained inhibition of the Erk, Akt and PKD signaling pathways," 53rd American Society of Hematology Annual Meeting and Exposition, San Diego, CA, Poster #2021 (2011).
Zent et al. The Treatment of Recurrent/Refractory chronic Lymphocytic Leukemia/Small Lymphocytic Lymphoma (CLL) With Everolimus Results in Clinical Responses and Mobilization of CLL Cells Into the Circulation. Cancer 116(9):2201-2207 (2010).
Zhu et al., "Calpain inhibitor II induces caspase-dependent apoptosis in human acute lymphoblastic leukemia and non-Hodgkin's lymphoma cells as well as some solid tumor cells," Clin Cancer Res, 6:2456-63 (2000).

* cited by examiner

FIG. 1

| IC50 (nM) | | |
|---|---|---|
| 0.39 | Btk | R P I F I I T E Y M A N G C L L N Y L R E M R H R |
| 1.10 | Bmx | Y P L Y L V T E Y L S N G C L L N Y I R S H G K G |
| 5.49 | Tec | K P I Y I V T E F M E R G C L L n F L R Q R Q G H |
| 2.84 | Txk | K P L Y I V T E F M E N G C L L N Y L R E N K G K |
| 11.70 | Itk | A P I C L V F E F M E H G C L S D Y L R T G R G L |
| 7.80 | EGFR | S T V Q L I T Q L M P F G C L L D Y V R E H K D N |
| 21.57 | ErbB2 | S T V Q L V T Q L M P Y G C L L D H V R E N R G R |
| 0.64 | ErbB4 | P T I Q L V T Q L M P H G C L L E Y V H E H K D N |
| 21.90 | Jak3 | P E L R L V M E Y L P S G C L R D F L Q R H R A R |
| 0.94 | Blk | E P I Y I V T E Y M A R G C L L D F L K T D E G S |

*: p<0.01 between the control and treatment groups, and among different dose groups.

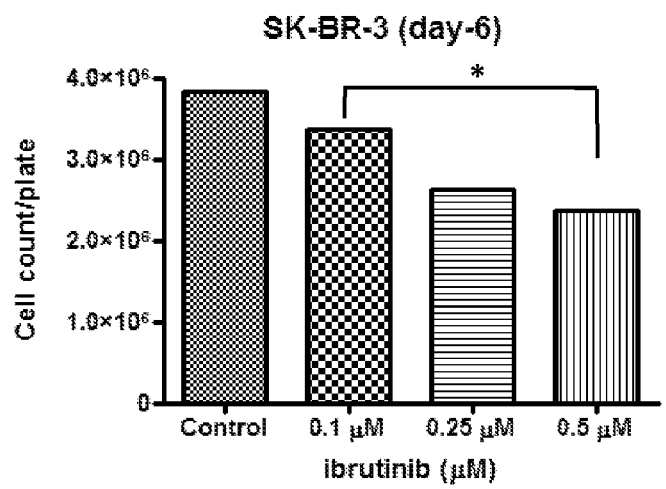

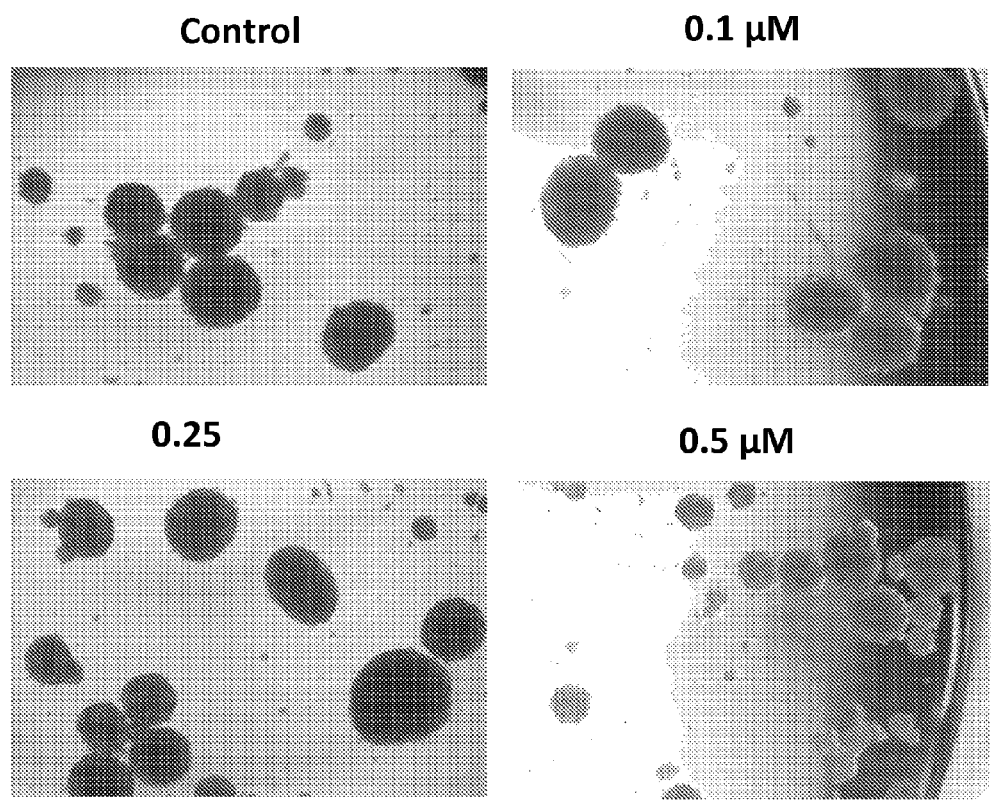

MDA-MB-453,
xenograft in vivo 1h treatment

FIG. 19B

| (nM) | Ibrutinib | Afatinib | |
|---|---|---|---|
| IC50 | 4.78 | 7.14 | EGFR |
| r: | 0.958 | 0.934 | |
| IC50 | 14.5 | 18.2 | HER2 |
| r: | 0.965 | 0.992 | |
| IC50 | 182.22 | 161.16 | HER4 |
| r: | 0.986 | 0.832 | |

FIG. 25B

| Enzyme | Condition | Initial Velocity, %-Conv*s-1 | 95%-conf interval, %-Conv*s-1 | %-Activity vs DMSO control |
|---|---|---|---|---|
| BTK | DMSO control, dialyzed | 0.03120 | 0.004431 | 100 |
| BTK | PCI-32765, 100nM, no dialysis | 0.00025 | 0.000083 | 0.8 |
| BTK | PCI-32765, 100nM, dialyzed | 0.00020 | 0.000099 | 0.7 |
| BTK | PCI-32765, 10nM, no dialysis | 0.00029 | 0.000035 | 0.9 |
| BTK | PCI-32765, 10nM, dialyzed | 0.00025 | 0.000018 | 0.8 |

FIG. 26B

| Enzyme | Condition | Initial Velocity, %-Conv*s-1 | 95%-conf interval, %-Conv*s-1 | %-Activity vs DMSO control |
|---|---|---|---|---|
| LCK | DMSO control, dialyzed | 0.00470 | 0.000285 | 100 |
| LCK | PCI-32765, 100nM, no dialysis | 0.00118 | 0.000103 | 25.1 |
| LCK | PCI-32765, 100nM, dialyzed | 0.00476 | 0.000296 | 101.3 |
| LCK | PCI-32765, 10nM, no dialysis | 0.00356 | 0.000049 | 75.8 |
| LCK | PCI-32765, 10nM, dialyzed | 0.00461 | 0.000222 | 98.2 |

FIG. 27B

| Enzyme | Condition | Initial Velocity, %-Conv*s-1 | 95%-conf interval, %-Conv*s-1 | %-Activity of DMSO control |
|---|---|---|---|---|
| EGFR | DMSO control, dialyzed | 0.00040 | 0.000031 | 100 |
| EGFR | PCI-32765, 100nM, no dialysis | 0.00001 | 0.000002 | 1.6 |
| EGFR | PCI-32765, 100nM, dialyzed | 0.00001 | 0.000002 | 2.1 |
| EGFR | PCI-32765, 10nM, no dialysis | 0.00001 | 0.000011 | 3.7 |
| EGFR | PCI-32765, 10nM, dialyzed | 0.00001 | 0.000005 | 2.5 |

FIG. 28B

| Enzyme | Condition | Initial Velocity, %-Conv*s-1 | 95%-conf interval, %-Conv*s-1 | %-Activity of DMSO control |
|---|---|---|---|---|
| HER4 | DMSO control, dialyzed | 0.00461 | 0.000147 | 100 |
| HER4 | PCI-32765, 100nM, no dialysis | 0.00003 | 0.000002 | 0.6 |
| HER4 | PCI-32765, 100nM, dialyzed | 0.00003 | 0.000003 | 0.6 |
| HER4 | PCI-32765, 10nM, no dialysis | 0.00006 | 0.000007 | 1.4 |
| HER4 | PCI-32765, 10nM, dialyzed | 0.00006 | 0.000004 | 1.2 |

| Enzyme | Compound ID | Conc., nM | Pre-incubation time, min | Initial Velocity, %-Conv*s-1 | 95%-conf, %-Conv*s-1 |
|---|---|---|---|---|---|
| BTK | PCI-32765 | 100nM | 90 | 4.40281E-05 | 3.33E-06 |
| BTK | PCI-32765 | 100nM | 60 | 4.34705E-05 | 1.11E-06 |
| BTK | PCI-32765 | 100nM | 30 | 4.30695E-05 | 1.2E-06 |
| BTK | PCI-32765 | 100nM | 15 | 4.6359E-05 | 4.2E-06 |
| BTK | PCI-32765 | 100nM | 5 | 0.000195288 | 2.31E-06 |
| BTK | DMSO | 0nM | 0 | 0.000904693 | 1.73E-05 |

| Parameter | Value | Units |
|---|---|---|
| Kobs | 0.370549 | min-1 |
| Kobs | 0.006176 | s-1 |

| Enzyme | Compound ID | Conc., nM | Pre-incubation time, min | Initial Velocity, %-Conv*s-1 | 95%-conf, %-Conv*s-1 |
|---|---|---|---|---|---|
| HER2 | PCI-32765 | 100nM | 90 | 0.000101529 | 1.3E-06 |
| HER2 | PCI-32765 | 100nM | 60 | 0.000175833 | 4.05E-06 |
| HER2 | PCI-32765 | 100nM | 30 | 0.000310592 | 2.38E-06 |
| HER2 | PCI-32765 | 100nM | 15 | 0.000457787 | 3.72E-06 |
| HER2 | PCI-32765 | 100nM | 5 | 0.000550079 | 4.88E-06 |
| HER2 | DMSO | 0nM | 0 | 0.000738112 | 6.85E-06 |

| Parameter | Value | Units |
|---|---|---|
| Kobs | 0.020101 | min-1 |
| Kobs | 0.000335 | s-1 |

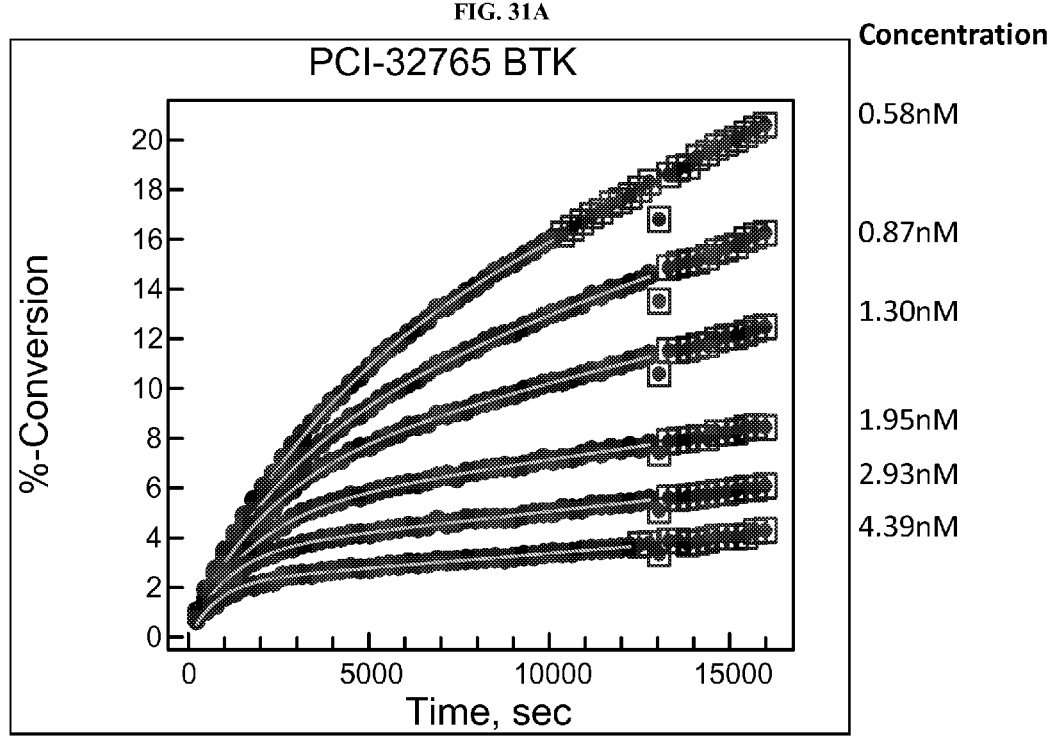

| Enzyme | Compound ID | Comound Conc., nM | Kobs, s-1 | 95%-conf, s-1 |
|---|---|---|---|---|
| BTK | PCI-32765 | 4.389575 | 0.001302 | 5.83E-05 |
| BTK | PCI-32765 | 2.926383 | 0.000897 | 2.2E-05 |
| BTK | PCI-32765 | 1.950922 | 0.000579 | 1.55E-05 |
| BTK | PCI-32765 | 1.300615 | 0.000437 | 1.46E-05 |
| BTK | PCI-32765 | 0.867076 | 0.000341 | 1.05E-05 |
| BTK | PCI-32765 | 0.578051 | 0.000221 | 1.79E-05 |

| Parameter | Value | Units |
|---|---|---|
| Kinact | 0.000350267 | s-1 |
| Ki*(1+[S]/61Km) | 747.9172847 | nM |
| K-2 | 0 | s-1 |
| Ki | 14.95834569 | nM |
| Kinact/61Ki | 2.34161E-05 | s-1*nM-1 |

| Enzyme | Compound ID | Compound Conc., nM | Kobs, s-1 | 95%-conf, s-1 |
|---|---|---|---|---|
| HER2 | PCI-32765 | 3333.333 | 0.000309726 | 3.09E-05 |
| HER2 | PCI-32765 | 1481.481 | 0.00019887 | 1.83E-05 |
| HER2 | PCI-32765 | 658.4362 | 0.000159447 | 9.92E-06 |
| HER2 | PCI-32765 | 438.9575 | 0.00012547 | 1.03E-05 |
| HER2 | PCI-32765 | 292.6383 | 9.77552E-05 | 5.17E-06 |
| HER2 | PCI-32765 | 130.0615 | 7.04784E-05 | 1.71E-06 |
| HER2 | PCI-32765 | 86.70765 | 6.29302E-05 | 1.25E-06 |
| HER2 | PCI-32765 | 57.8051 | 4.65864E-05 | 1.21E-06 |

METHODS FOR THE TREATMENT OF HER2 AMPLIFIED CANCER

RELATED APPLICATION

The present application is a continuation of U.S. patent application Ser. No. 15/198,694, filed Jun. 30, 2016, now U.S. Pat. No. 9,724,349, issued Aug. 8, 2017, which is a continuation of U.S. patent application Ser. No. 14/458,157, filed Aug. 12, 2014, now U.S. Pat. No. 9,415,050, issued Aug. 16, 2016, which claims the benefit of priority from U.S. Provisional Patent Application Nos. 61/865,059, filed Aug. 12, 2013, and 61/969,003, filed Mar. 21, 2014, each of which are herein incorporated by reference in their entireties.

SEQUENCE LISTING

The instant application contains a Sequence Listing which has been submitted electronically in ASCII format and is hereby incorporated by reference in its entirety. Said ASCII copy, created on Oct. 3, 2017, is named PIR-89003_SL.txt and is 3,705 bytes in size.

SUMMARY OF THE INVENTION

Disclosed herein, in certain embodiments, are pharmaceutical compositions for use in treating HER2 amplified breast cancer in a patient, wherein the pharmaceutical composition comprises (R)-1-(3-(4-amino-3-(4-phenoxyphenyl)-1H-pyrazolo[3,4-d]pyrimidin-1-yl)piperidin-1-yl)prop-2-en-1-one

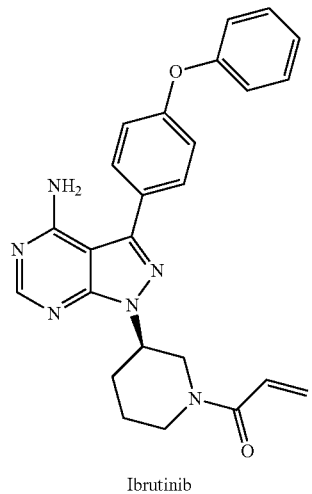

Ibrutinib

In some embodiments, a dose of ibrutinib is from about 100 mg/day up to, and including, about 2000 mg/day. In some embodiments, a dose of ibrutinib is from about 140 mg/day up to, and including, about 840 mg/day. In some embodiments, a dose of ibrutinib is from about 420 mg/day up to, and including, about 840 mg/day. In some embodiments, a dose of ibrutinib is about 140 mg/day. In some embodiments, a dose of ibrutinib is about 280 mg/day. In some embodiments, a dose of ibrutinib is about 420 mg/day. In some embodiments, a dose of ibrutinib is about 560 mg/day. In some embodiments, a dose of ibrutinib is about 700 mg/day. In some embodiments, a dose of ibrutinib is about 840 mg/day. In some embodiments, a dose of ibrutinib is about 980 mg/day. In some embodiments, a dose of ibrutinib is about 1120 mg/day. In some embodiments, a dose of ibrutinib is about 1260 mg/day. In some embodiments, a dose of ibrutinib is about 1400 mg/day. In some embodiments, the pharmaceutical composition further comprises co-administering an additional therapeutic agent. In some embodiments, the additional therapeutic agent is an anti-HER2 therapeutic agent. In some embodiments, the anti-HER2 therapeutic agent is selected from the group consisting of: trastuzumab, trastuzumab emtansine, pertuzumab, lapatinib, and MM-111 (Merrimack Pharmaceuticals). In some embodiments, the anti-HER2 therapeutic agent is trastuzumab. In some embodiments, the anti-HER2 therapeutic agent is trastuzumab emtansine. In some embodiments, the anti-HER2 therapeutic agent is lapatinib. In some embodiments, the anti-HER2 therapeutic agent is pertuzumab. In some embodiments, the anti-HER2 therapeutic agent is MM-111. In some embodiments, the additional therapeutic agent is a pan-ErbB inhibitor. In some embodiments, the pan-ErbB inhibitor is selected from the group consisting of: afatinib, neratinib, and dacomitinib. In some embodiments, the pan-ErbB inhibitor is afatinib. In some embodiments, the pan-ErbB inhibitor is neratinib. In some embodiments, the pan-ErbB inhibitor is dacomitinib. In some embodiments, the additional therapeutic agent is an anti-VEGF therapeutic agent. In some embodiments, the anti-VEGF therapeutic agent is selected from the group consisting of: bevacizumab, ranibizumab, lapatinib, sunitinib, sorafenib, axitinib, and pazopanib. In some embodiments, the anti-VEGF therapeutic agent is bevacizumab. In some embodiments, the anti-VEGF therapeutic agent is ranibizumab. In some embodiments, the anti-VEGF therapeutic agent is lapatinib. In some embodiments, the anti-VEGF therapeutic agent is sunitinib. In some embodiments, the anti-VEGF therapeutic agent is sorafenib. In some embodiments, the anti-VEGF therapeutic agent is axitinib. In some embodiments, the anti-VEGF therapeutic agent is pazopanib. In some embodiments, the additional therapeutic agent is selected from the group consisting of: temsirolimus, paclitaxel, ASLAN001 (also, ARRY-543, ASLAN Pharmaceuticals), vorinostat, doxorubicin, cyclophosphamide, cisplatin, docetaxel, and dasatinib. In some embodiments, the additional therapeutic agent is doxorubicin. In some embodiments, the additional therapeutic agent is docetaxel. In some embodiments, the additional therapeutic agent is paclitaxal. In some embodiments, the additional therapeutic agent is trastuzumab and docetaxel. In some embodiments, the additional therapeutic agent is pertuzumab and docetaxel. In some embodiments, the additional therapeutic agent is doxorubicin, cyclophosphamide and paclitaxal. In some embodiments, the additional therapeutic agent is doxorubicin, cyclophosphamide and 5-FU. In some embodiments, the HER2-amplified breast cancer is metastatic. In some embodiments, the HER2-amplified breast cancer has metastasized to the brain. In some embodiments, the HER2-amplified breast cancer is refractory to treatment. In some embodiments, the HER2-amplified breast cancer is refractory to a treatment selected from: trastuzumab, trastuzumab emtansine, pertuzumab, lapatinib, or MM-111. In some embodiments, the HER2-amplified breast cancer is refractory to trastuzumab. In some embodiments, the HER2-amplified breast cancer is recurrent. In some embodiments, the HER2-amplified breast cancer has a HER2:CEP17 ratio >4.0. In some embodiments, the HER2-amplified breast cancer has a HER2:CEP17 ratio of 2.2-4.0. In some embodiments, the HER2-amplified breast cancer is graded 3+ using IHC.

Disclosed herein, in certain embodiments, are pharmaceutical compositions for use in treating HER2 amplified cancer in a patient, wherein the pharmaceutical composition comprises (R)-1-(3-(4-amino-3-(4-phenoxyphenyl)-1H-pyrazolo[3,4-d]pyrimidin-1-yl)piperidin-1-yl)prop-2-en-1-one

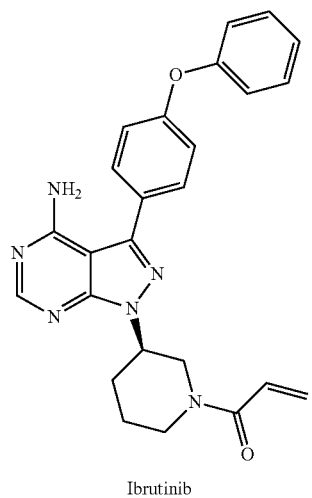

Ibrutinib

In some embodiments, the HER2-amplified cancer is selected from the group consisting of: breast, colon, endometrial, cervical, urothelial, lung (including, non-small cell lung cancer), ovarian, gastric, gastroesophageal junction (GEJ), head and neck, biliary tract, prostate, and pancreatic cancer. In some embodiments, the HER2-amplified cancer is HER2-amplified breast cancer. In some embodiments, the HER2-amplified cancer is HER2-amplified colon cancer. In some embodiments, the HER2-amplified cancer is HER2-amplified endometrial cancer. In some embodiments, the HER2-amplified cancer is HER2-amplified cervical cancer. In some embodiments, the HER2-amplified cancer is HER2-amplified urothelial cancer. In some embodiments, the HER2-amplified cancer is HER2-amplified lung cancer. In some embodiments, the HER2-amplified lung cancer is HER2-amplified non-small cell lung cancer. In some embodiments, the HER2-amplified cancer is HER2-amplified ovarian cancer. In some embodiments, the HER2-amplified cancer is HER2-amplified gastric cancer. In some embodiments, the HER2-amplified cancer is HER2-amplified gastroesophageal junction (GEJ) cancer. In some embodiments, the HER2-amplified cancer is HER2-amplified head and neck cancer. In some embodiments, the HER2-amplified cancer is HER2-amplified biliary tract cancer. In some embodiments, the HER2-amplified cancer is HER2-amplified prostate cancer. In some embodiments, the HER2-amplified cancer is HER2-amplified pancreatic cancer. In some embodiments, the HER2-amplified cancer is metastatic. In some embodiments, the HER2-amplified cancer has metastasized to the brain. In some embodiments, the HER2-amplified cancer has a HER2:CEP17 ratio >4.0. In some embodiments, the HER2-amplified cancer has a HER2:CEP17 ratio of 2.2-4.0. In some embodiments, the HER2-amplified cancer is graded 3+ using IHC. In some embodiments, the HER2-amplified cancer is refractory to treatment. In some embodiments, the treatment to which the HER2-amplified cancer is refractory is selected from: trastuzumab, trastuzumab emtansine, pertuzumab, lapatinib, or MM-111. In some embodiments, the treatment to which the HER2-amplified cancer is refractory is trastuzumab. In some embodiments, the HER2-amplified cancer is recurrent. In some embodiments, the pharmaceutical composition further comprises co-administering an additional therapeutic agent. In some embodiments, the additional therapeutic agent is an anti-HER2 therapeutic agent. In some embodiments, the anti-HER2 therapeutic agent is selected from the group consisting of: trastuzumab, trastuzumab emtansine, pertuzumab, lapatinib, and MM-111 (Merrimack Pharmaceuticals). In some embodiments, the anti-HER2 therapeutic agent is trastuzumab. In some embodiments, the anti-HER2 therapeutic agent is trastuzumab emtansine. In some embodiments, the anti-HER2 therapeutic agent is lapatinib. In some embodiments, the anti-HER2 therapeutic agent is pertuzumab. In some embodiments, the anti-HER2 therapeutic agent is MM-111. In some embodiments, the additional therapeutic agent is a pan-ErbB inhibitor. In some embodiments, the pan-ErbB inhibitor is selected from the group consisting of: afatinib, neratinib, and dacomitinib. In some embodiments, the pan-ErbB inhibitor is afatinib. In some embodiments, the pan-ErbB inhibitor is neratinib. In some embodiments, the pan-ErbB inhibitor is dacomitinib. In some embodiments, the additional therapeutic agent is an anti-VEGF therapeutic agent. In some embodiments, the anti-VEGF therapeutic agent is selected from the group consisting of: bevacizumab, ranibizumab, lapatinib, sunitinib, sorafenib, axitinib, and pazopanib. In some embodiments, the anti-VEGF therapeutic agent is bevacizumab. In some embodiments, the anti-VEGF therapeutic agent is ranibizumab. In some embodiments, the anti-VEGF therapeutic agent is lapatinib. In some embodiments, the anti-VEGF therapeutic agent is sunitinib. In some embodiments, the anti-VEGF therapeutic agent is sorafenib. In some embodiments, the anti-VEGF therapeutic agent is axitinib. In some embodiments, the anti-VEGF therapeutic agent is pazopanib. In some embodiments, the additional therapeutic agent is selected from the group consisting of: temsirolimus, paclitaxel, ASLAN001 (also, ARRY-543, ASLAN Pharmaceuticals), vorinostat, doxorubicin, cyclophosphamide, cisplatin, docetaxel, and dasatinib. In some embodiments, the additional therapeutic agent is doxorubicin. In some embodiments, the additional therapeutic agent is docetaxel. In some embodiments, the additional therapeutic agent is paclitaxal. In some embodiments, the additional therapeutic agent is trastuzumab and docetaxel. In some embodiments, the additional therapeutic agent is pertuzumab and docetaxel. In some embodiments, the additional therapeutic agent is doxorubicin, cyclophosphamide and paclitaxal. In some embodiments, the additional therapeutic agent is doxorubicin, cyclophosphamide and 5-FU. In some embodiments, a dose of ibrutinib is from about 100 mg/day up to, and including, about 2000 mg/day. In some embodiments, a dose of ibrutinib is from about 140 mg/day up to, and including, about 840 mg/day. In some embodiments, a dose of ibrutinib is from about 420 mg/day up to, and including, about 840 mg/day. In some embodiments, a dose of ibrutinib is about 140 mg/day. In some embodiments, a dose of ibrutinib is about 280 mg/day. In some embodiments, a dose of ibrutinib is about 420 mg/day. In some embodiments, a dose of ibrutinib is about 560 mg/day. In some embodiments, a dose of ibrutinib is about 700 mg/day. In some embodiments, a dose of ibrutinib is about 840 mg/day. In some embodiments, a dose of ibrutinib is about 980 mg/day. In some embodiments, a dose of ibrutinib is about 1120 mg/day. In some embodiments, a dose of ibrutinib is about 1260 mg/day. In some embodiments, a dose of ibrutinib is about 1400 mg/day.

Disclosed herein, in certain embodiments, are methods for treating HER2 amplified breast cancer in an individual in need thereof comprising administering to an individual in need thereof a composition comprising (R)-1-(3-(4-amino-3-(4-phenoxyphenyl)-1H-pyrazolo[3,4-d]pyrimidin-1-yl)piperidin-1-yl)prop-2-en-1-one

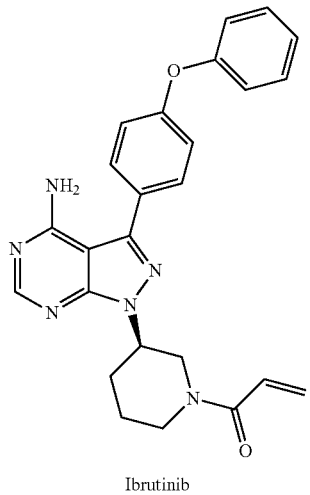

Ibrutinib

In some embodiments, a dose of ibrutinib is from about 100 mg/day up to, and including, about 2000 mg/day. In some embodiments, a dose of ibrutinib is from about 140 mg/day up to, and including, about 840 mg/day. In some embodiments, a dose of ibrutinib is from about 420 mg/day up to, and including, about 840 mg/day. In some embodiments, a dose of ibrutinib is about 140 mg/day. In some embodiments, a dose of ibrutinib is about 280 mg/day. In some embodiments, a dose of ibrutinib is about 420 mg/day. In some embodiments, a dose of ibrutinib is about 560 mg/day. In some embodiments, a dose of ibrutinib is about 700 mg/day. In some embodiments, a dose of ibrutinib is about 840 mg/day. In some embodiments, a dose of ibrutinib is about 980 mg/day. In some embodiments, a dose of ibrutinib is about 1120 mg/day. In some embodiments, a dose of ibrutinib is about 1260 mg/day. In some embodiments, a dose of ibrutinib is about 1400 mg/day. In some embodiments, the HER2-amplified breast cancer is metastatic. In some embodiments, the HER2-amplified breast cancer has metastasized to the brain. In some embodiments, the HER2-amplified breast cancer is refractory to treatment. In some embodiments, the HER2-amplified breast cancer is refractory to a treatment selected from: trastuzumab, trastuzumab emtansine, pertuzumab, lapatinib, or MM-111. In some embodiments, the HER2-amplified breast cancer is refractory to trastuzumab. In some embodiments, the HER2-amplified breast cancer is recurrent. In some embodiments, the HER2-amplified breast cancer has a HER2:CEP17 ratio >4.0. In some embodiments, the HER2-amplified breast cancer has a HER2:CEP17 ratio of 2.2-4.0. In some embodiments, the HER2-amplified breast cancer is graded 3+ using IHC. In some embodiments, the methods further comprise co-administering an additional therapeutic agent. In some embodiments, the additional therapeutic agent is an anti-HER2 therapeutic agent. In some embodiments, the anti-HER2 therapeutic agent is a kinase inhibitor. In some embodiments, the anti-HER2 therapeutic agent is selected from the group consisting of: trastuzumab, trastuzumab emtansine, pertuzumab, lapatinib, and MM-111 (Merrimack Pharmaceuticals). In some embodiments, the anti-HER2 therapeutic agent is trastuzumab. In some embodiments, the anti-HER2 therapeutic agent is trastuzumab emtansine. In some embodiments, the anti-HER2 therapeutic agent is lapatinib. In some embodiments, the anti-HER2 therapeutic agent is pertuzumab. In some embodiments, the anti-HER2 therapeutic agent is MM-111. In some embodiments, the additional therapeutic agent is a pan-ErbB inhibitor. In some embodiments, the pan-ErbB inhibitor is selected from the group consisting of: afatinib, neratinib, and dacomitinib. In some embodiments, the pan-ErbB inhibitor is afatinib. In some embodiments, the pan-ErbB inhibitor is neratinib. In some embodiments, the pan-ErbB inhibitor is dacomitinib. In some embodiments, the additional therapeutic agent is an anti-VEGF therapeutic agent. In some embodiments, the anti-VEGF therapeutic agent is selected from the group consisting of: bevacizumab, ranibizumab, lapatinib, sunitinib, sorafenib, axitinib, and pazopanib. In some embodiments, the anti-VEGF therapeutic agent is bevacizumab. In some embodiments, the anti-VEGF therapeutic agent is ranibizumab. In some embodiments, the anti-VEGF therapeutic agent is lapatinib. In some embodiments, the anti-VEGF therapeutic agent is sunitinib. In some embodiments, the anti-VEGF therapeutic agent is sorafenib. In some embodiments, the anti-VEGF therapeutic agent is axitinib. In some embodiments, the anti-VEGF therapeutic agent is pazopanib. In some embodiments, the additional therapeutic agent is selected from the group consisting of: temsirolimus, paclitaxel, ASLAN001 (also, ARRY-543, ASLAN Pharmaceuticals), vorinostat, doxorubicin, cyclophosphamide, cisplatin, docetaxel, and dasatinib. In some embodiments, the additional therapeutic agent is doxorubicin. In some embodiments, the additional therapeutic agent is docetaxel. In some embodiments, the additional therapeutic agent is paclitaxal. In some embodiments, the additional therapeutic agent is trastuzumab and docetaxel. In some embodiments, the additional therapeutic agent is pertuzumab and docetaxel. In some embodiments, the additional therapeutic agent is doxorubicin, cyclophosphamide and paclitaxal. In some embodiments, the additional therapeutic agent is doxorubicin, cyclophosphamide and 5-FU.

Disclosed herein, in certain embodiments, are methods for treating HER2 amplified cancer in an individual in need thereof comprising administering to an individual in need thereof a composition comprising (R)-1-(3-(4-amino-3-(4-phenoxyphenyl)-1H-pyrazolo[3,4-d]pyrimidin-1-yl)piperidin-1-yl)prop-2-en-1-one

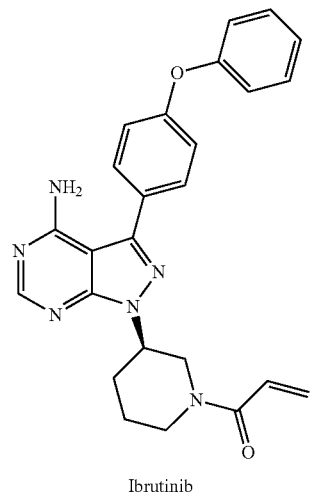

Ibrutinib

In some embodiments, a dose of ibrutinib is from about 100 mg/day up to, and including, about 2000 mg/day. In some embodiments, a dose of ibrutinib is from about 140 mg/day up to, and including, about 840 mg/day. In some embodiments, a dose of ibrutinib is from about 420 mg/day up to, and including, about 840 mg/day. In some embodiments, a dose of ibrutinib is about 140 mg/day. In some embodiments, a dose of ibrutinib is about 280 mg/day. In some embodiments, a dose of ibrutinib is about 420 mg/day. In some embodiments, a dose of ibrutinib is about 560 mg/day. In some embodiments, a dose of ibrutinib is about 700 mg/day. In some embodiments, a dose of ibrutinib is about 840 mg/day. In some embodiments, a dose of ibrutinib is about 980 mg/day. In some embodiments, a dose of ibrutinib is about 1120 mg/day. In some embodiments, a dose of ibrutinib is about 1260 mg/day. In some embodiments, a dose of ibrutinib is about 1400 mg/day. In some embodiments, the HER2-amplified cancer is selected from the group consisting of: breast, colon, endometrial, cervical, urothelial, lung (including, non-small cell lung cancer), ovarian, gastric, gastroesophageal junction (GEJ), head and neck, biliary tract, prostate, and pancreatic cancer. In some embodiments, the HER2-amplified cancer is HER2-amplified breast cancer. In some embodiments, the HER2-amplified cancer is HER2-amplified colon cancer. In some embodiments, the HER2-amplified cancer is HER2-amplified endometrial cancer. In some embodiments, the HER2-amplified cancer is HER2-amplified cervical cancer. In some embodiments, the HER2-amplified cancer is HER2-amplified urothelial cancer. In some embodiments, the HER2-amplified cancer is HER2-amplified lung cancer. In some embodiments, the HER2-amplified lung cancer is HER2-amplified non-small cell lung cancer. In some embodiments, the HER2-amplified cancer is HER2-amplified ovarian cancer. In some embodiments, the HER2-amplified cancer is HER2-amplified gastric cancer. In some embodiments, the HER2-amplified cancer is HER2-amplified gastroesophageal junction (GEJ) cancer. In some embodiments, the HER2-amplified cancer is HER2-amplified head and neck cancer. In some embodiments, the HER2-amplified cancer is HER2-amplified biliary tract cancer. In some embodiments, the HER2-amplified cancer is HER2-amplified prostate cancer. In some embodiments, the HER2-amplified cancer is HER2-amplified pancreatic cancer. In some embodiments, the HER2-amplified cancer is metastatic. In some embodiments, the HER2-amplified cancer has metastasized to the brain. In some embodiments, the HER2-amplified cancer has a HER2:CEP17 ratio >4.0. In some embodiments, the HER2-amplified cancer has a HER2:CEP17 ratio of 2.2-4.0. In some embodiments, the HER2-amplified cancer is graded 3+ using IHC. In some embodiments, the HER2-amplified cancer is refractory to treatment. In some embodiments, the treatment to which the HER2-amplified cancer is refractory is selected from: trastuzumab, trastuzumab emtansine, pertuzumab, lapatinib, or MM-111. In some embodiments, the treatment to which the HER2-amplified cancer is refractory is trastuzumab. In some embodiments, the HER2-amplified cancer is recurrent. In some embodiments, the methods further comprise co-administering an additional therapeutic agent. In some embodiments, the additional therapeutic agent is an anti-HER2 therapeutic agent. In some embodiments, the anti-HER2 therapeutic agent is a kinase inhibitor. In some embodiments, the anti-HER2 therapeutic agent is selected from the group consisting of: trastuzumab, trastuzumab emtansine, pertuzumab, lapatinib, and MM-111 (Merrimack Pharmaceuticals). In some embodiments, the anti-HER2 therapeutic agent is trastuzumab. In some embodiments, the anti-HER2 therapeutic agent is trastuzumab emtansine. In some embodiments, the anti-HER2 therapeutic agent is lapatinib. In some embodiments, the anti-HER2 therapeutic agent is pertuzumab. In some embodiments, the anti-HER2 therapeutic agent is MM-111. In some embodiments, the additional therapeutic agent is a pan-ErbB inhibitor. In some embodiments, the pan-ErbB inhibitor is selected from the group consisting of: afatinib, neratinib, and dacomitinib. In some embodiments, the pan-ErbB inhibitor is afatinib. In some embodiments, the pan-ErbB inhibitor is neratinib. In some embodiments, the pan-ErbB inhibitor is dacomitinib. In some embodiments, the additional therapeutic agent is an anti-VEGF therapeutic agent. In some embodiments, the anti-VEGF therapeutic agent is selected from the group consisting of: bevacizumab, ranibizumab, lapatinib, sunitinib, sorafenib, axitinib, and pazopanib. In some embodiments, the anti-VEGF therapeutic agent is bevacizumab. In some embodiments, the anti-VEGF therapeutic agent is ranibizumab. In some embodiments, the anti-VEGF therapeutic agent is lapatinib. In some embodiments, the anti-VEGF therapeutic agent is sunitinib. In some embodiments, the anti-VEGF therapeutic agent is sorafenib. In some embodiments, the anti-VEGF therapeutic agent is axitinib. In some embodiments, the anti-VEGF therapeutic agent is pazopanib. In some embodiments, the additional therapeutic agent is selected from the group consisting of: temsirolimus, paclitaxel, ASLAN001 (also, ARRY-543, ASLAN Pharmaceuticals), vorinostat, doxorubicin, cyclophosphamide, cisplatin, docetaxel, and dasatinib. In some embodiments, the additional therapeutic agent is doxorubicin. In some embodiments, the additional therapeutic agent is docetaxel. In some embodiments, the additional therapeutic agent is paclitaxal. In some embodiments, the additional therapeutic agent is trastuzumab and docetaxel. In some embodiments, the additional therapeutic agent is pertuzumab and docetaxel. In some embodiments, the additional therapeutic agent is doxorubicin, cyclophosphamide and paclitaxal. In some embodiments, the additional therapeutic agent is doxorubicin, cyclophosphamide and 5-FU.

Other objects, features and advantages of the methods and compositions described herein will become apparent from the following detailed description. It should be understood, however, that the detailed description and the specific examples, while indicating specific embodiments, are given by way of illustration only. The section headings used herein are for organizational purposes only and are not to be construed as limiting the subject matter described.

BRIEF DESCRIPTION OF THE FIGURES

FIG. 1: exemplifies the homology among members of the ErbB kinase and TEC kinase families and IC50 values for inhibition of each kinase by ibrutinib. FIG. 1 discloses SEQ ID NOS 3-12, respectively, in order of appearance.

FIG. 3A-FIG. 3B: exemplify the effects of ibrutinib on relative cell growth after 1 hour ibrutinib incubation (Day 1) followed by wash out and six days culture (Day 6) (A) BT-474 cells—ibrutinib (0.1 µM, 0.25 µM, 0.5 µM); (B) SK-BR3 cells—ibrutinib (0.1 µM, 0.25 µM, 0.5 µM).

FIG. 6A-FIG. 6C: exemplify the effects of ibrutinib on tumorsphere growth after 1 hour ibrutinib treatment followed by wash out and seven days culture. (A) Graph of tumorsphere size for increasing concentrations of ibrutinib (0.1 µM, 0.25 µM, 0.5 µM) *: p, 0.05; **: p<0.01. (B) Graph of tumorsphere size for each concentration of ibrutinib tested. (C) Photomicrograph of selected tumorspheres for each concentration of ibrutinib tested.

FIG. 19A and FIG. 19B: exemplify the comparison of signaling pathway inhibition between ibrutinib and afatinib (A) and the associated IC50 values (B).

FIG. 25A-FIG. 25C: exemplify BTK dialysis experiment. Ibrutinib irreversibly inhibits Btk.

FIG. 26A-FIG. 26C: exemplify LCK dialysis experiment. Ibrutinib reversibly inhibits LCK.

FIG. 27A-FIG. 27C: exemplify EFGR dialysis experiment. Ibrutinib irreversibly inhibits EFGR.

FIG. 28A-FIG. 28C: exemplify HER4 dialysis experiment. Ibrutinib irreversibly inhibits HER4.

FIG. 29A illustrates the progress curves profile after pre-incubation. FIG. 29B illustrates the initial velocity table. FIG. 29C illustrates a graphical representation of preincubation time vs. initial velocity. FIG. 29D illustrates the parameters associated with the time-dependent inhibition.

FIG. 30A illustrates the progress curves profile after pre-incubation. FIG. 30B illustrates the initial velocity table. FIG. 30C illustrates a graphical representation of preincubation time vs. initial velocity. FIG. 30D illustrates the parameters associated with the time-dependent inhibition.

FIG. 31A-FIG. 31D: exemplify the kinetics of BTK inhibition by ibrutinib. FIG. 31A illustrates the progress curves profile at the different concentrations of ibrutinib. FIG. 31B illustrates the parameters associated with the time-dependent inhibition. FIG. 31C illustrates a graphical representation of concentration vs Kobs. FIG. 31D illustrates the Kobs values for each concentration of ibrutinib. FIT was calculated using the equation: $FIT=Vs*t+((Vo-Vs)/Kobs)*(1-exp(-Kobs*t))$. Kobs was calculated using the equation: $Kobs=Kinact*[I]/([I]+Ki*(1+[S]/Km))$.

FIG. 32A illustrates the progress curves profile at the different concentrations of ibrutinib. FIG. 32B illustrates the parameters associated with the time-dependent inhibition. FIG. 32C illustrates a graphical representation of concentration vs Kobs. FIG. 32D illustrates the Kobs values for each concentration of ibrutinib. FIT was calculated using the equation: $FIT=Vs*t+((Vo-Vs)/Kobs)*(1-exp(-Kobs*t))$. Kobs was calculated using the equation: $Kobs=Kinact*[I]/([I]+Ki*(1+[S]/Km))$.

DETAILED DESCRIPTION OF THE INVENTION

Figure 2A:
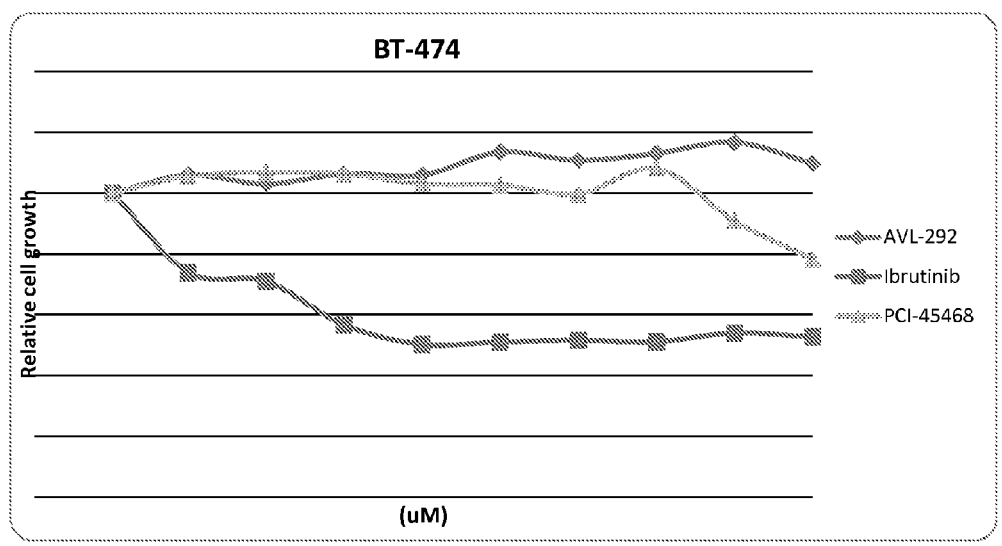
FIG. 2A-FIG. 2D: exemplify the effects of ibrutinib on relative cell growth (A) BT-474 cells—ibrutinib, AVL-292 and PCI-45468; (B) SK-BR3 cells—ibrutinib, AVL-292 and PCI-4546; (C) UACC-893 cells—ibrutinib; and (D) MDA-MB-453 cells—ibrutinib, AVL-292 and PCI-4546.
Figure 2B:
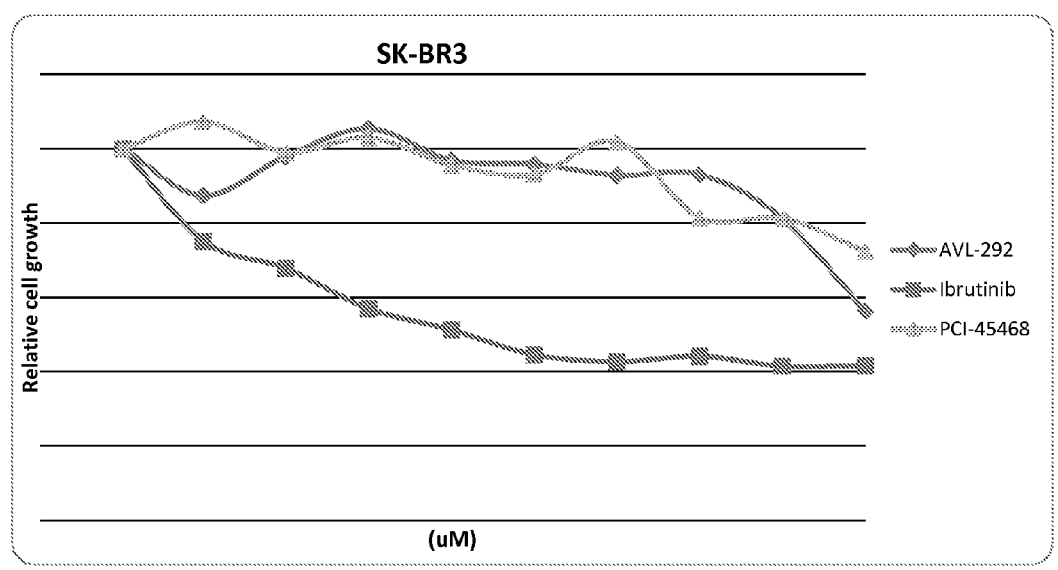
Figure 2C:
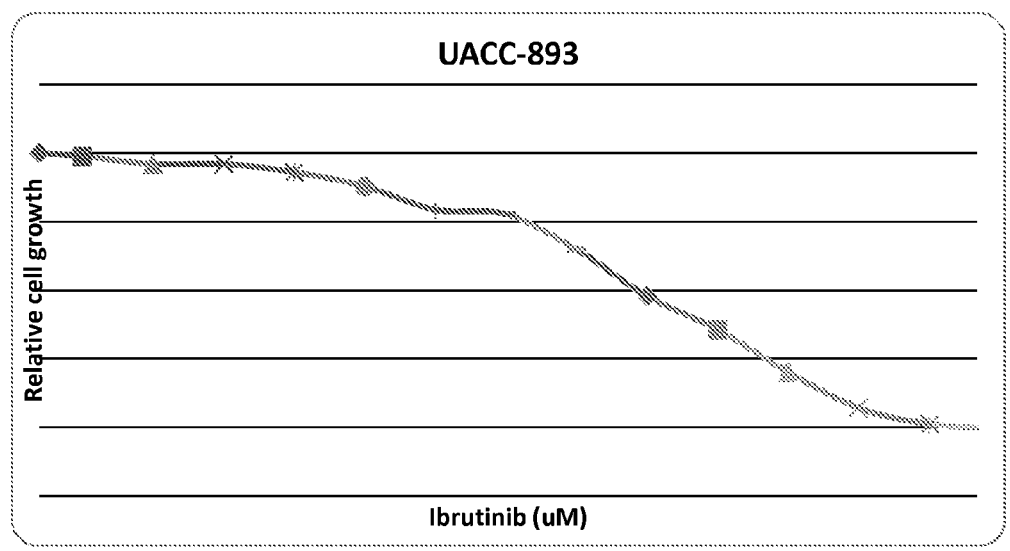
Figure 2D:
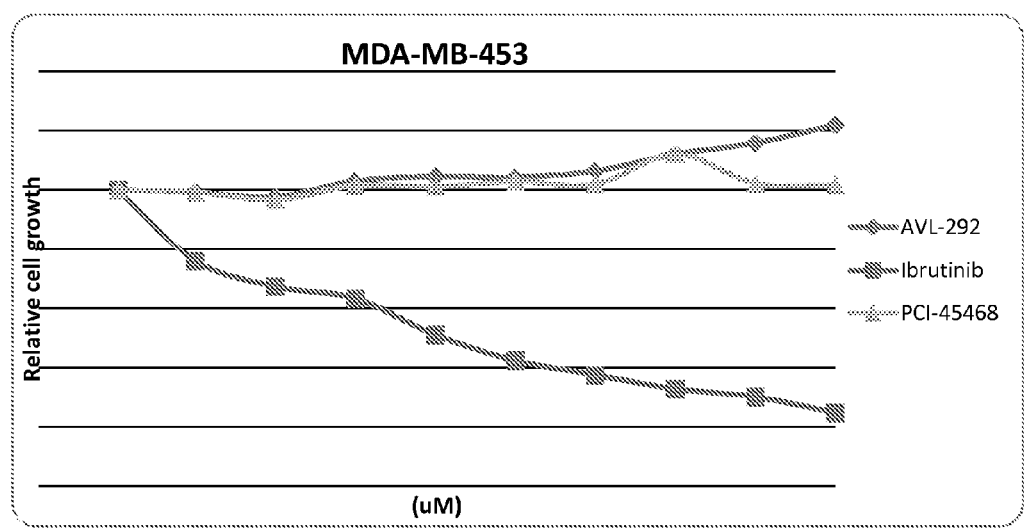

Disclosed herein, in certain embodiments, are methods and pharmaceutical compositions for treating HER2 amplified cancer in an individual in need thereof comprising administering to an individual in need thereof a composition comprising (R)-1-(3-(4-amino-3-(4-phenoxyphenyl)-1H-pyrazolo[3,4-d]pyrimidin-1-yl)piperidin-1-yl)prop-2-en-1-one

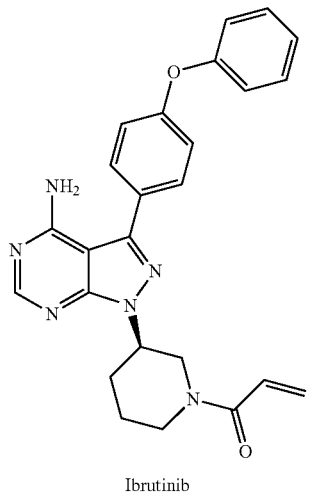

Ibrutinib

Further disclosed herein, in certain embodiments, are methods and pharmaceutical compositions for treating HER2 amplified cancer in an individual in need thereof comprising administering to an individual in need thereof a composition comprising (R)-1-(3-(4-amino-3-(4-phenoxyphenyl)-1H-pyrazolo[3,4-d]pyrimidin-1-yl)piperidin-1-yl)prop-2-en-1-one

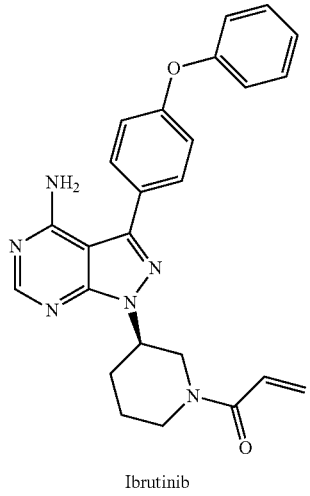

Ibrutinib

Certain Terminology

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, "ACK" and "Accessible Cysteine Kinase" are synonyms. They mean a kinase with an accessible cysteine residue. ACKs include, but are not limited to, BTK, ITK, BMX/ETK, TEC, EFGR, HER2, HER4, LCK, BLK, C-src, FGR, Fyn, HCK, Lyn, YES, ABL, Brk, CSK, FER, JAK3, SYK. In some embodiments, the ACK is HER2. In some embodiments, the ACK is HER4.

As used herein, "amelioration" refers to any lessening of severity, delay in onset, slowing of growth, slowing of metastasis, or shortening of duration of HER2-amplified breast cancer, whether permanent or temporary, lasting or transient that can be attributed to or associated with administration of the compound or composition.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Accession No. AAB47246), dog (GenBank Accession No. XP_549139), rat (GenBank Accession No. NP_001007799), chicken (GenBank Accession No. NP_989564), or zebra fish (GenBank Accession No. XP_698117), and fusion proteins of any of the foregoing that exhibit kinase activity towards one or more substrates of Bruton's tyrosine kinase (e.g. a peptide substrate having the amino acid sequence "AVLESEEEL-YSSARQ" (SEQ ID NO: 1)).

The term "HER2", also known as ERBB2, also known as "V-erb-b2 erythroblastic leukemia viral oncogene homolog 2" means either (a) the nucleic acid sequence encoding a receptor tyrosine kinase that is a member of the epidermal growth factor receptor subfamily, or (b) the protein thereof. For the nucleic acid sequence that comprises the human HER2 gene see GenBank Accession No. NM_004448. For the amino acid sequence that comprises the human HER2 protein see GenBank Accession No. NP_004439.

The term "HER4", also known as ERBB4, also known as "V-erb-b2 erythroblastic leukemia viral oncogene homolog 4" means either (a) the nucleic acid sequence encoding a receptor tyrosine kinase that is a member of the epidermal growth factor receptor subfamily, or (b) the protein thereof. For the nucleic acid sequence that comprises the human HER4 gene see GenBank Accession No. NM_001042599. For the amino acid sequence that comprises the human HER4 protein see GenBank Accession No. NP_001036064.

The term "homologous cysteine," as used herein refers to a cysteine residue found within a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys350.

The term "irreversible Btk inhibitor," as used herein, refers to an inhibitor of Btk that can form a covalent bond with an amino acid residue of Btk. In one embodiment, the irreversible inhibitor of Btk can form a covalent bond with a Cys residue of Btk; in particular embodiments, the irreversible inhibitor can form a covalent bond with a Cys 481 residue (or a homolog thereof) of Btk or a cysteine residue in the homologous corresponding position of another tyrosine kinase, as shown in FIG. 1.

As used herein, the term "pAKT" refers to phosphorylated AKT at Thr308 as detected by commercially available phospho-specific antibodies (e.g. Santa Cruz Biotech sc-16646).

As used herein, the term "pERK" refers to phosphorylated ERK1 and ERK2 at Thr202/Tyr 204 as detected by commercially available phospho-specific antibodies (e.g. Cell Signaling Technologies #4377).

The terms "individual", "patient" and "subject" are used interchangeable. They refer to a mammal (e.g., a human) which is the object of treatment, or observation. The term is not to be construed as requiring the supervision of a medical practitioner (e.g., a physician, physician's assistant, nurse, orderly, hospice care worker).

The terms "treat," "treating" or "treatment", as used herein, include lessening of severity of HER2-amplified breast cancer, delay in onset of HER2-amplified breast cancer, slowing the growth of HER2-amplified breast cancer, slowing metastasis of cells of HER2-amplified breast cancer, shortening of duration of HER2-amplified breast cancer, arresting the development of HER2-amplified breast cancer, causing regression of HER2-amplified breast cancer, relieving a condition caused by of HER2-amplified breast cancer, or stopping symptoms which result from HER2-amplified breast cancer. The terms "treat," "treating" or "treatment", include, but are not limited to, prophylactic and/or therapeutic treatments.

The term "breast cancer", as used herein, includes ductal carcinoma in situ (intraductal carcinoma), lobular carcinoma in situ, invasive (or infiltrating) ductal carcinoma, invasive (or infiltrating) lobular carcinoma, inflammatory breast cancer, triple-negative breast cancer, paget disease of the nipple, phyllodes tumor, angiosarcoma or invasive breast carcinoma. In some embodiments, the invasive breast carcinoma is further categorized into subtypes. In some embodiments, the subtypes include adenoid cystic (or adenocystic) carcinoma, low-grade adenosquamous carcinoma, medullary carcinoma, mucinous (or colloid) carcinoma, papillary carcinoma, tubular carcinoma, metaplastic carcinoma, micropapillary carcinoma or mixed carcinoma.

In some embodiments, the breast cancer is further classified according to stages or how far the tumor cells have spread within the breast tissues and to other portions of the body. In some embodiments, there are five stages of breast cancer, Stage 0-IV. In some embodiments, Stage 0 breast cancer refers to non-invasive breast cancers or that there are no evidence of cancer cells or abnormal non-cancerous cells breaking out of the origin site. In some embodiments, Stage I breast cancer refers to invasive breast cancer in which the cancer cells have invaded into surrounding tissues. In some embodiments, Stage I is subclassified into Stage IA and IB, in which Stage IA describes tumor measures up to about 2 cm with no spread of cancer cells. Stage IB describes absence of tumor in breast but have small lumps of cancer cells between about 0.2 mm to about 2 mm within the lymph nodes. In some embodiments, Stage II breast cancer is further subdivided into Stage IIA and IIB. In some embodiments, Stage IIA describes tumor between about 2 cm to about 5 cm in breast only, or absence of tumor in breast but with cancer between about 2 mm to about 2 cm in axillary lymph nodes. In some embodiments, Stage IIB describes tumor larger than about 5 cm in breast only, or tumor between about 2 cm to about 5 cm in breast with presence of small tumors from about 0.2 mm to about 2 mm in axillary lymph nodes. In some embodiments, Stage III breast cancer is further subdivided into Stage IIIA, IIIB, and IIIC. In some embodiments, Stage IIIA describes absence of tumor or tumor greater than about 5 cm in breast with small tumors in about 4-9 axillary lymph nodes or small tumors about 0.2 mm to about 2 mm in size in axillary lymph nodes. In some embodiments, Stage IIIB describes tumor spreading into the chest wall or skin of the breast causing swelling or ulcer and with presence of tumor in up to about 9 axillary lymph nodes. In some embodiments, inflammatory breast cancer is also considered as Stage IIIB. In some embodiments, Stage IIIC describes absence of tumor or tumor spreading into the chest wall or to the skin of the breast, with tumor present in 10 or more axillary lymph nodes. In some embodiments, Stage IV breast cancer refers to invasive breast cancer that has metastasized into the lymph nodes and other portions of the body.

HER2 Amplified Cancer

Described herein are methods of treating HER2 amplified breast cancer in an individual in need thereof comprising administering to the individual a composition comprising a therapeutically-effective amount of an ACK inhibitor compound (e.g., a BTK inhibitor, such as for example ibrutinib). As shown herein, ibrutinib is an ACK inhibitor compound that is effective in inhibiting the activity of ErbB kinases, such as EGFR (ErbB1), HER2 (ErbB2) and HER4 (ErbB4). Further described herein are methods of treating HER2 amplified cancer in an individual in need thereof comprising administering to the individual a composition comprising a therapeutically-effective amount of an ACK inhibitor compound (e.g., a BTK inhibitor, such as for example ibrutinib).

HER2 (Human Epidermal Growth Factor Receptor 2) also known as Neu, ErbB2, CD340 (cluster of differentiation 340) and p185 is an epidermal growth factor receptor found on cells. The HER2 gene is found on human chromosome 17. HER2 protein is composed of four plasma membrane-bound receptor tyrosine kinases. Signaling pathways activated by HER2 protein include: mitogen-activated protein kinase (MAPK), phosphoinositide 3-kinase (PI3K/Akt), phospholipase C γ, protein kinase C (PKC), and signal transducer and activator of transcription (STAT).

As used herein, "HER2-amplified cancer" means a cancer (e.g., breast cancer) characterized by amplification (or, over-expression) of the HER2 gene. Amplification of HER2 gene expression leads to increased membrane expression of the HER2 protein. Increased expression is associated with increased dimerization of HER2 proteins with HER3 and HER4. Increased dimerization leads to increased activation of the HER2 tyrosine kinase resulting in excessive mitosis and cell replication.

HER2 amplification has been identified in breast, colon, endometrial, cervical, urothelial, lung (including, non-small cell lung cancer), ovarian, gastric, gastroesophageal junction (GEJ), head and neck, biliary tract, prostate, and pancreatic adenocarcinomas. HER2 amplification is present in about 18%-25% of breast cancers. HER2 amplification is also present in about 30% of GEJ cancers and about 20% of gastric cancers. In some embodiments, the HER2 amplified cancer is selected from: breast, colon, endometrial, cervical, urothelial, lung, ovarian, salivary duct, gastric and gastroesophageal junction (GEJ) cancer. In some embodiments, the HER2 amplified cancer is HER2 amplified breast cancer. In some embodiments, the HER2 amplified cancer is HER2 amplified gastric cancer. In some embodiments, the HER2 amplified cancer is HER2 amplified gastroesophageal junction (GEJ) cancer.

HER2 amplified tumors are characterized by an aggressive phenotype (e.g., increased cell proliferation, increased cell survival, increased cell motility, and increased cell adhesion), increased metastasis, increased relapse, shorter disease-free survival and poorer overall survival. In some embodiments, the HER2 amplified cancer is metastatic HER2 amplified cancer. Individuals with HER2 amplified breast cancer are at a high risk of developing brain metastases. In some embodiments, the HER2 amplified breast cancer is metastatic HER2 amplified breast cancer. In some embodiments, the HER2 amplified breast cancer has metastasized to the brain.

The degree of HER2 amplification is variable amongst tumors. Some tumors have high levels of amplification (HER2:CEP17 ratio >4.0), whereas others have lower levels amplification (HER2:CEP17 ratio of 2.0-4.0, or HER2:CEP17 ratio of 2.2-4.0). Several tests are used to diagnose and classify HER2 amplification: immunohistochemistry (IHC), Fluorescence In Situ Hybridization (FISH), Subtraction Probe Technology Chromogenic In Situ Hybridization (SPoT-Light HER2 CISH), and Inform HER2 Dual In Situ Hybridization (ISH). Using IHC, a cancer is classified as HER2-amplified if it is rated 3+. Using FISH, a cancer is generally classified as HER2-amplified if it has a HER2:CEP17 ratio of 2.2-4.0. A HER2:CEP17 ratio of 1.8 to 2.2 is considered equivocal.

In some instances, HER2 amplified tumors is associated with the presence and in some cases elevated expression of heregulin. Heregulin (HRG, also known as neuregulin) is a member of the EGF-like growth and differentiation factors. There are four isoforms of HRG (HRG1-HRG4). HRG binds with high affinity to the receptors of ErbB3 and ErbB4, members of the human epidermal growth factor receptor (EGFR) family of receptors. Upon activation, ErbB3 undergoes heterodimerization with other members of the ErbB family, leading to cell differentiation, migration, proliferation, and survival.

In some cases, the presence and/or elevated level of HRG in breast cancer is correlated with poor histological grades. In some cases, the presence and/or elevated level of HRG in HER2 amplified breast cancer is correlated with poor histological grades. In some cases, the presence and/or elevated level of HRG in HER2 amplified tumors is correlated with poor histological grades.

In some cases, breast cancer contains an elevated level of HRG. In some cases, HER2 amplified breast cancer contains an elevated level of HRG. In some cases, HER2 amplified tumors contains an elevated level of HRG.

In some cases, HRG induces resistance in breast cancer. In some cases, HRG induces resistance in HER2 amplified breast cancer. In some cases, HRG induces resistance in HER2 amplified tumors.

In some cases, the presence or absence or the expression level of HRG is used to select a patient for therapy. In some cases, the presence or absence or the expression level of HRG is used to monitor a patient's treatment progress. In some cases, the presence or absence or the expression level of HRG is used to optimize a therapeutic regimen.

Current agents used to treat HER2-amplified cancer include trastuzumab, trastuzumab emtansine (also, ado-trastuzumab emtansine), pertuzumab, and lapatinib. Certain individuals with HER2 amplified breast cancer treated with trastuzumab develop recurrent disease, even if placed on adjuvant trastuzumab therapy. Many patients with HER2 amplified cancer do not respond to therapy or develop refractory disease, in some instances within 1 year of treatment. In some embodiments, the HER2 amplified cancer is recurrent. In some embodiments, the HER2 amplified cancer is refractory, for example to trastuzumab.

Administration

Described herein are methods and pharmaceutical compositions of treating HER2 amplified breast cancer in an individual in need thereof comprising administering to the individual a composition comprising a therapeutically-effective amount of an ACK inhibitor compound (e.g., a BTK inhibitor, such as for example ibrutinib). Further described herein are methods and pharmaceutical compositions of treating HER2 amplified cancer in an individual in need thereof comprising administering to the individual a composition comprising a therapeutically-effective amount of an ACK inhibitor compound (e.g., a BTK inhibitor, such as for example ibrutinib). In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

The ACK inhibitor compound (e.g., a BTK inhibitor, such as for example ibrutinib) is administered before, during or after the development of the HER2-amplified cancer. In some embodiments, the ACK inhibitor compound (e.g., a BTK inhibitor, such as for example ibrutinib) is used as a prophylactic and is administered continuously to subjects with a propensity to develop HER2-amplified cancer. In some embodiments, the ACK inhibitor compound (e.g., a BTK inhibitor, such as for example ibrutinib) is administered to an individual during or as soon as possible after the development of HER2-amplified cancer. In some embodiments, the administration of the ACK inhibitor compound (e.g., a BTK inhibitor, such as for example ibrutinib) is initiated within the first 48 hours of the onset of the symptoms, within the first 6 hours of the onset of the symptoms, or within 3 hours of the onset of the symptoms. In some embodiments, the initial administration of the ACK inhibitor compound (e.g., a BTK inhibitor, such as for example ibrutinib) is via any route practical, such as, for example, an intravenous injection, a bolus injection, infusion over 5 minutes to about 5 hours, a pill, a capsule, transdermal patch, buccal delivery, and the like, or combination thereof. The ACK inhibitor compound (e.g., a BTK inhibitor, such as for example ibrutinib) should be administered as soon as is practicable after the onset of a disorder is detected or suspected, and for a length of time necessary for the treatment of the disease, such as, for example, from about 1 month to about 3 months. The length of treatment can vary for each subject, and the length can be determined using the known criteria. In some embodiments, the ACK inhibitor compound (e.g., a BTK inhibitor, such as for example ibrutinib) is administered for at least 2 weeks, between about 1 month to about 5 years, or from about 1 month to about 3 years.

Therapeutically effective amounts will depend on the severity and course of the disorder, previous therapy, the patient's health status, weight, and response to the drugs, and the judgment of the treating physician. Prophylactically effective amounts depend on the patient's state of health, weight, the severity and course of the disease, previous therapy, response to the drugs, and the judgment of the treating physician.

In some embodiments, the ACK inhibitor compound (e.g., a BTK inhibitor, such as for example ibrutinib) is administered to the patient on a regular basis, e.g., three times a day, two times a day, once a day, every other day or every 3 days. In other embodiments, the ACK inhibitor compound (e.g., a BTK inhibitor, such as for example ibrutinib) is administered to the patient on an intermittent basis, e.g., twice a day followed by once a day followed by three times a day; or the first two days of every week; or the first, second and third day of a week. In some embodiments, intermittent dosing is as effective as regular dosing. In further or alternative embodiments, the ACK inhibitor compound (e.g., a BTK inhibitor, such as for example ibrutinib) is administered only when the patient exhibits a particular symptom, e.g., the onset of pain, or the onset of a fever, or the onset of an inflammation, or the onset of a skin disorder. Dosing schedules of each compound may depend on the other or may be independent of the other.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance regimen is administered if necessary. Subsequently, the dosage or the frequency of administration, or both, of the ACK inhibitor compound (e.g., a BTK inhibitor, such as for example ibrutinib) can be reduced, as a function of the symptoms, to a level at which the individual's improved condition is retained. Individuals can, however, require intermittent treatment on a long-term basis upon any recurrence of symptoms.

The amount of the ACK inhibitor compound (e.g., a BTK inhibitor, such as for example ibrutinib) will vary depending upon factors such as the particular compound, disorder and its severity, the identity (e.g., weight) of the subject or host in need of treatment, and is determined according to the particular circumstances surrounding the case, including, e.g., the specific agents being administered, the routes of administration, and the subject or host being treated. In general, however, doses employed for adult human treatment will typically be in the range of 0.02-5000 mg per day, or from about 1-1500 mg per day. The desired dose may be presented in a single dose or as divided doses administered simultaneously (or over a short period of time) or at appropriate intervals, for example as two, three, four or more sub-doses per day.

In some embodiments, the therapeutic amount of the ACK inhibitor (e.g., a BTK inhibitor, such as for example ibrutinib) is from 10 mg/day up to, and including, 2000 mg/day. In some embodiments, the therapeutic amount of the ACK inhibitor (e.g., a BTK inhibitor, such as for example ibrutinib) is from 40 mg/day up to, and including, 2000 mg/day. In some embodiments, the therapeutic amount of the ACK inhibitor (e.g., a BTK inhibitor, such as for example ibrutinib) is from 100 mg/day up to, and including, 2000 mg/day. In some embodiments, the amount of the ACK inhibitor (e.g., a BTK inhibitor, such as for example ibrutinib) is from 140 mg/day up to, and including, 840 mg/day. In some embodiments, the amount of the ACK inhibitor (e.g., a BTK inhibitor, such as for example ibrutinib) is from 420 mg/day up to, and including, 840 mg/day. In some embodiments, the amount of the ACK inhibitor (e.g. a BTK inhibitor, such as for example ibrutinib) is about 10 mg/day, about 11 mg/day, about 12 mg/day, about 13 mg/day, about 14 mg/day, about 15 mg/day, about 16 mg/day, about 17 mg/day, about 18 mg/day, about 19 mg/day, about 20 mg/day, about 25 mg/day, about 30 mg/day, about 35 mg/day, about 40 mg/day, about 45 mg/day, about 50 mg/day, about 55 mg/day, about 60 mg/day, about 65 mg/day, about 70 mg/day, about 75 mg/day, about 80 mg/day, about 85 mg/day, about 90 mg/day, about 95 mg/day, about 100 mg/day, about 110 mg/day, about 120 mg/day, about 125 mg/day, about 130 mg/day, about 135 mg/day, about 140 mg/day, about 150 mg/day, about 160 mg/day, about 170 mg/day, about 180 mg/day, about 190 mg/day, about 200 mg/day, about 280 mg/day, about 360 mg/day, about 420 mg/day, about 560 mg/day, about 700 mg/day, about 840 mg/day, about 980 mg/day, about 1120 mg/day, or about 1260 mg/day. In some embodiments, the amount of the ACK inhibitor (e.g., a BTK inhibitor, such as for example ibrutinib) is about 140 mg/day. In some embodiments, the amount of the ACK inhibitor (e.g., a BTK inhibitor, such as for example ibrutinib) is about 280 mg/day. In some embodiments, the amount of the ACK inhibitor (e.g., a BTK inhibitor, such as for example ibrutinib) is about 420 mg/day. In some embodiments, the amount of the ACK inhibitor (e.g., a BTK inhibitor, such as for example ibrutinib) is about 560 mg/day. In some embodiments, the amount of the ACK inhibitor (e.g., a BTK inhibitor, such as for example ibrutinib) is about 700 mg/day. In some embodiments, the amount of the ACK inhibitor (e.g., a BTK inhibitor, such as for example ibrutinib) is about 840 mg/day. In some embodiments, the amount of the ACK inhibitor (e.g., a BTK inhibitor, such as for example ibrutinib) is about 980 mg/day. In some embodiments, the amount of the ACK inhibitor (e.g., a BTK inhibitor, such as for example ibrutinib) is about 1120 mg/day. In some embodiments, the amount of the ACK inhibitor (e.g., a BTK inhibitor, such as for example ibrutinib) is about 1260 mg/day. In some embodiments, the amount of the ACK inhibitor (e.g., a BTK inhibitor, such as for example ibrutinib) is about 1400 mg/day.

In some embodiments, the dosage of the ACK inhibitor (e.g., a BTK inhibitor, such as for example ibrutinib) is escalated over time. In some embodiments, the dosage of the ACK inhibitor (e.g., a BTK inhibitor, such as for example ibrutinib) is escalated from at or about 1.25 mg/kg/day to at or about 12.5 mg/kg/day over a predetermined period of time. In some embodiments the predetermined period of time is over 1 month, over 2 months, over 3 months, over 4 months, over 5 months, over 6 months, over 7 months, over 8 months, over 9 months, over 10 months, over 11 months, over 12 months, over 18 months, over 24 months or longer.

The ACK inhibitor compound (e.g., a BTK inhibitor, such as for example ibrutinib) may be formulated into unit dosage forms suitable for single administration of precise dosages. In unit dosage form, the formulation is divided into unit doses containing appropriate quantities of one or both compounds. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

It is understood that a medical professional will determine the dosage regimen in accordance with a variety of factors. These factors include the solid tumor from which the subject suffers, the degree of metastasis, as well as the age, weight, sex, diet, and medical condition of the subject.

Compounds

Described herein are methods and pharmaceutical compositions of treating HER2 amplified breast cancer in an individual in need thereof comprising administering to the individual a composition comprising a therapeutically-effective amount of an ACK inhibitor compound (e.g., a BTK inhibitor, such as for example ibrutinib). Further described herein are methods and pharmaceutical compositions of treating HER2 amplified cancer in an individual in need thereof comprising administering to the individual a composition comprising a therapeutically-effective amount of an ACK inhibitor compound (e.g., a BTK inhibitor, such as for example ibrutinib).

Definition of standard chemistry terms are found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques are optionally used for chemical syntheses, chemical analyses, pharmaceutical preparation, formulation, and delivery, and treatment of patients. Standard techniques are optionally used for recombinant DNA, oligonucleotide synthesis, and tissue culture and transformation (e.g., electroporation, lipofection). Reactions and purification techniques are performed using documented methodologies or as described herein.

It is to be understood that the methods and compositions described herein are not limited to the particular methodology, protocols, cell lines, constructs, and reagents described herein and as such optionally vary. It is also to be understood that the terminology used herein is for the purpose of describing particular embodiments only, and is not intended to limit the scope of the methods and compositions described herein, which will be limited only by the appended claims.

Unless stated otherwise, the terms used for complex moieties (i.e., multiple chains of moieties) are to be read equivalently either from left to right or right to left. For example, the group alkylenecycloalkylene refers both to an alkylene group followed by a cycloalkylene group or as a cycloalkylene group followed by an alkylene group.

The suffix "ene" appended to a group indicates that such a group is a diradical. By way of example only, a methylene is a diradical of a methyl group, that is, it is a —$CH_2$— group; and an ethylene is a diradical of an ethyl group, i.e., —$CH_2CH_2$—.

An "alkyl" group refers to an aliphatic hydrocarbon group. The alkyl moiety includes a "saturated alkyl" group, which means that it does not contain any alkene or alkyne moieties. The alkyl moiety also includes an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, includes branched, straight chain, or cyclic moieties. Depending on the structure, an alkyl group includes a monoradical or a diradical (i.e., an alkylene group), and if a "lower alkyl" having 1 to 6 carbon atoms.

As used herein, $C_1$-$C_x$ includes $C_1$-$C_2$, $C_1$-$C_3$ ... $C_1$-$C_x$.

The "alkyl" moiety optionally has 1 to 10 carbon atoms (whenever it appears herein, a numerical range such as "1 to 10" refers to each integer in the given range; e.g., "1 to 10 carbon atoms" means that the alkyl group is selected from a moiety having 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl, iso-propyl, n-butyl, iso-butyl, sec-butyl, and t-butyl. Thus $C_1$-$C_4$ alkyl includes $C_1$-$C_2$ alkyl and $C_1$-$C_3$ alkyl. Alkyl groups are optionally substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

The term "alkenyl" refers to a type of alkyl group in which the first two atoms of the alkyl group form a double bond that is not part of an aromatic group. That is, an alkenyl group begins with the atoms —C(R)=C(R)—R, wherein R refers to the remaining portions of the alkenyl group, which are either the same or different. The alkenyl moiety is optionally branched, straight chain, or cyclic (in which case, it is also known as a "cycloalkenyl" group). Depending on the structure, an alkenyl group includes a monoradical or a diradical (i.e., an alkenylene group). Alkenyl groups are optionally substituted. Non-limiting examples of an alkenyl group include —CH=$CH_2$, —C($CH_3$)=$CH_2$, —CH=$CHCH_3$, —C($CH_3$)=$CHCH_3$. Alkenylene groups include, but are not limited to, —CH=CH—, —C($CH_3$)=CH—, —CH=$CHCH_2$—, —CH=$CHCH_2CH_2$— and —C($CH_3$)=$CHCH_2$—. Alkenyl groups optionally have 2 to 10 carbons, and if a "lower alkenyl" having 2 to 6 carbon atoms.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which is either the same or different. The "R" portion of the alkynyl moiety may be branched, straight chain, or cyclic. Depending on the structure, an alkynyl group includes a monoradical or a diradical (i.e., an alkynylene group). Alkynyl groups are optionally substituted. Non-limiting examples of an alkynyl group include, but are not limited to, —C≡CH, —C≡$CCH_3$, —C≡$CCH_2CH_3$, —C≡C—, and —C≡$CCH_2$—. Alkynyl groups optionally have 2 to 10 carbons, and if a "lower alkynyl" having 2 to 6 carbon atoms.

An "alkoxy" group refers to a (alkyl)O— group, where alkyl is as defined herein.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

The term "alkylamine" refers to the —N(alkyl)$_x$H$_y$ group, where x and y are selected from among x=1, y=1 and x=2, y=0. When x=2, the alkyl groups, taken together with the N atom to which they are attached, optionally form a cyclic ring system.

"Alkylaminoalkyl" refers to an alkyl radical, as defined herein, substituted with an alkylamine, as defined herein.

"Hydroxyalkylaminoalkyl" refers to an alkyl radical, as defined herein, substituted with an alkylamine, and alkylhydroxy, as defined herein.

"Alkoxyalkylaminoalkyl" refers to an alkyl radical, as defined herein, substituted with an alkylamine and substituted with an alkylalkoxy, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). In some embodiments, an amide moiety forms a linkage between an amino acid or a peptide molecule and a compound described herein, thereby forming a prodrug. Any amine, or carboxyl side chain on the compounds described herein can be amidified. The procedures and specific groups to make such amides are found in sources such as Greene and Wuts, Protective Groups in Organic Synthesis, 3$^{rd}$ Ed., John Wiley & Sons, New York, N.Y., 1999, which is incorporated herein by reference for this disclosure.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are found in sources such as Greene and Wuts, Protective Groups in Organic Synthesis, 3$^{rd}$ Ed., John Wiley & Sons, New York, N.Y., 1999, which is incorporated herein by reference for this disclosure.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e. a heteroatom). Heterocycle includes heteroaryl and heterocycloalkyl. Carbocycles and heterocycles can be optionally substituted.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

An "aryloxy" group refers to an (aryl)O— group, where aryl is as defined herein.

The term "carbonyl" as used herein refers to a group containing a moiety selected from the group consisting of —C(O)—, —S(O)—, —S(O)2-, and —C(S)—, including, but not limited to, groups containing a least one ketone group, and/or at least one aldehyde group, and/or at least one ester group, and/or at least one carboxylic acid group, and/or at least one thioester group. Such carbonyl groups include ketones, aldehydes, carboxylic acids, esters, and thioesters. In some embodiments, such groups are a part of linear, branched, or cyclic molecules.

The term "cycloalkyl" refers to a monocyclic or polycyclic radical that contains only carbon and hydrogen, and is optionally saturated, partially unsaturated, or fully unsaturated. Cycloalkyl groups include groups having from 3 to 10 ring atoms. Illustrative examples of cycloalkyl groups include the following moieties:

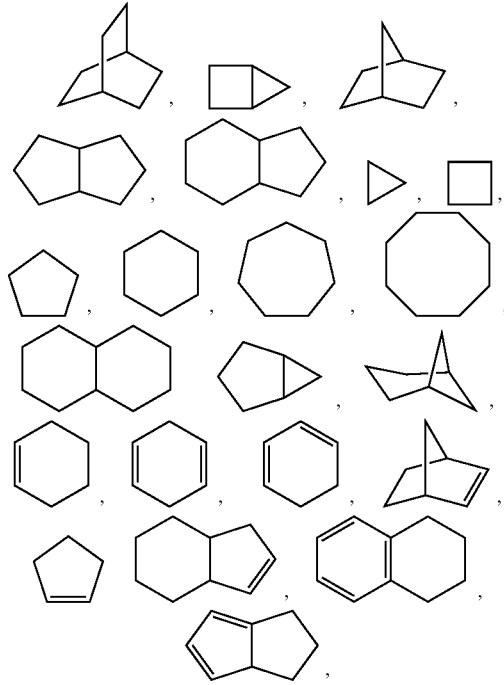

and the like. Depending on the structure, a cycloalkyl group is either a monoradical or a diradical (e.g., an cycloalkylene group), and if a "lower cycloalkyl" having 3 to 8 carbon atoms.

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, are optionally C-attached or N-attached where such is possible. For instance, a group derived from pyrrole includes pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

The terms "heteroaryl" or, alternatively, "heteroaromatic" refers to an aromatic group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Illustrative examples of heteroaryl groups include the following moieties:

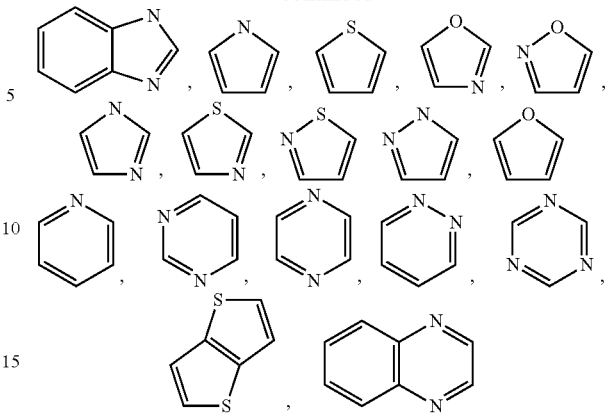

and the like. Depending on the structure, a heteroaryl group can be a monoradical or a diradical (i.e., a heteroarylene group).

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. In some embodiments, the radicals are fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

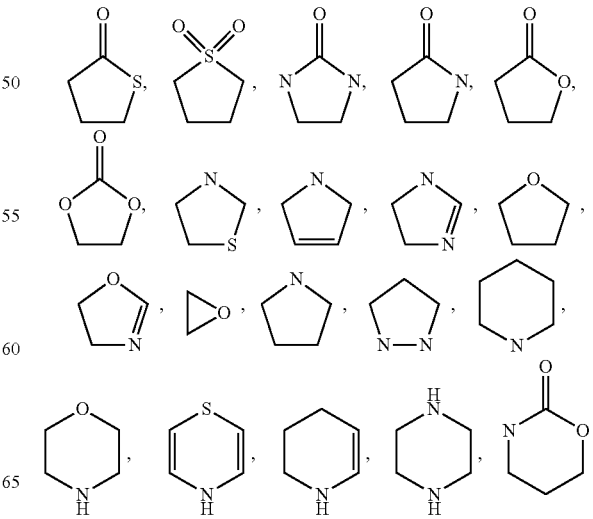

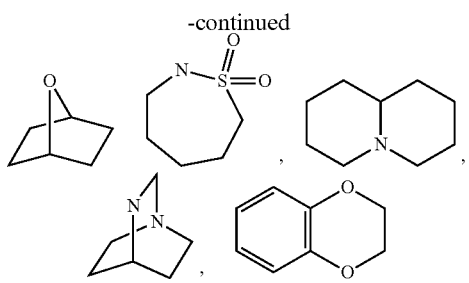

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

The term "halo" or, alternatively, "halogen" or "halide" means fluoro, chloro, bromo and iodo.

The term "haloalkyl," refers to alkyl structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "fluoroalkyl," as used herein, refers to alkyl group in which at least one hydrogen is replaced with a fluorine atom. Examples of fluoroalkyl groups include, but are not limited to, —$CF_3$, —$CH_2CF_3$, —$CF_2CF_3$, —$CH_2CH_2CF_3$ and the like.

As used herein, the term "heteroalkyl" refers to optionally substituted alkyl radicals in which one or more skeletal chain atoms is a heteroatom, e.g., oxygen, nitrogen, sulfur, silicon, phosphorus or combinations thereof. The heteroatom(s) are placed at any interior position of the heteroalkyl group or at the position at which the heteroalkyl group is attached to the remainder of the molecule. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. In addition, in some embodiments, up to two heteroatoms are consecutive, such as, by way of example, —$CH_2$—NH—O$CH_3$ and —$CH_2$—O—Si($CH_3$)$_3$—.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

A "thioalkoxy" or "alkylthio" group refers to a —S-alkyl group.

A "SH" group is also referred to either as a thiol group or a sulfhydryl group.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof. By way of example an optional substituents may be $L_sR_s$, wherein each $L_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted $C_1$-$C_6$ alkyl), or -(substituted or unsubstituted $C_2$-$C_6$ alkenyl); and each $R_s$ is independently selected from H, (substituted or unsubstituted $C_1$-$C_4$alkyl), (substituted or unsubstituted $C_3$-$C_6$cycloalkyl), heteroaryl, or heteroalkyl. The protecting groups that form the protective derivatives of the above substituents include those found in sources such as Greene and Wuts, above.

ACK Inhibitor Compounds

Described herein are methods and pharmaceutical compositions of treating HER2 amplified breast cancer in an individual in need thereof comprising administering to the individual a composition comprising a therapeutically-effective amount of an ACK inhibitor compound (e.g., a BTK inhibitor, such as for example ibrutinib). Further described herein are methods and pharmaceutical compositions of treating HER2 amplified cancer in an individual in need thereof comprising administering to the individual a composition comprising a therapeutically-effective amount of an ACK inhibitor compound (e.g., a BTK inhibitor, such as for example ibrutinib).

The ACK inhibitor compounds described herein are selective for kinases having an accessible cysteine that is able to form a covalent bond with a Michael acceptor moiety on the inhibitor compound. In some embodiments, the cysteine residue is accessible or becomes accessible when the binding site moiety of the irreversible inhibitor binds to the kinase. That is, the binding site moiety of the irreversible inhibitor binds to an active site of the ACK and the Michael acceptor moiety of irreversible inhibitor gains access (in one embodiment the step of binding leads to a conformational change in the ACK, thus exposing the cysteine) or is otherwise exposed to the cysteine residue of the ACK; as a result a covalent bond is formed between the "S" of the cysteine residue and the Michael acceptor of the irreversible inhibitor. Consequently, the binding site moiety of the irreversible inhibitor remains bound or otherwise blocks the active site of the ACK.

In one embodiment, the ACK is Btk, a homolog of Btk or a tyrosine kinase having a cysteine residue in an amino acid sequence position that is homologous to the amino acid sequence position of cysteine 481 in Btk. In some embodiments, the ACK is HER4. Inhibitor compounds described herein include a Michael acceptor moiety, a binding site moiety and a linker that links the binding site moiety and the Michael acceptor moiety (and in some embodiments, the structure of the linker provides a conformation, or otherwise directs the Michael acceptor moiety, so as to improve the selectivity of the irreversible inhibitor for a particular ACK).

In some embodiments, the ACK inhibitor is a compound of Formula (A):

Formula (A)

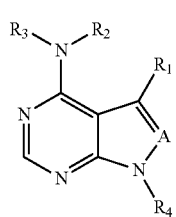

wherein
A is independently selected from N or CR$_5$;
R$_1$ is H, L$_2$-(substituted or unsubstituted alkyl), L$_2$-(substituted or unsubstituted cycloalkyl), L$_2$-(substituted or unsubstituted alkenyl), L$_2$-(substituted or unsubstituted cycloalkenyl), L$_2$-(substituted or unsubstituted heterocycle), L$_2$-(substituted or unsubstituted heteroaryl), or L$_2$-(substituted or unsubstituted aryl), where L$_2$ is a bond, O, S, —S(=O), —S(=O)$_2$, C(=O), -(substituted or unsubstituted C$_1$-C$_6$ alkyl), or -(substituted or unsubstituted C$_2$-C$_6$ alkenyl);
R$_2$ and R$_3$ are independently selected from H, lower alkyl and substituted lower alkyl;
R$_4$ is L$_3$-X-L$_4$-G, wherein,
L$_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;
X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;
L$_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;
or L$_3$, X and L$_4$ taken together form a nitrogen containing heterocyclic ring;
G is

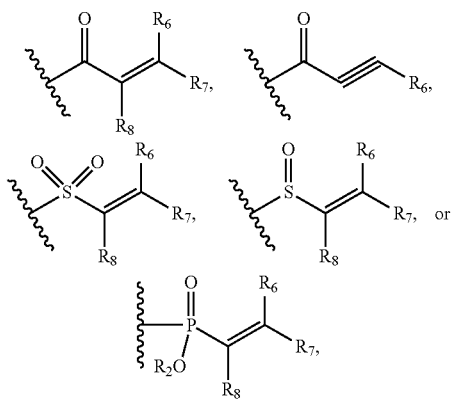

wherein, R$_6$, R$_7$ and R$_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;
R$_5$ is H, halogen, -L$_6$-(substituted or unsubstituted C$_1$-C$_3$ alkyl), -L$_6$-(substituted or unsubstituted C$_2$-C$_4$ alkenyl), -L$_6$-(substituted or unsubstituted heteroaryl), or -L$_6$-(substituted or unsubstituted aryl), wherein L$_6$ is a bond, O, S, —S(=O), S(=O)$_2$, NH, C(O), —NHC(O)O, —OC(O)NH, —NHC(O), or —C(O)NH;

each R$_9$ is independently selected from among H, substituted or unsubstituted lower alkyl, and substituted or unsubstituted lower cycloalkyl;
each R$_{10}$ is independently H, substituted or unsubstituted lower alkyl, or substituted or unsubstituted lower cycloalkyl; or
two R$_{10}$ groups can together form a 5-, 6-, 7-, or 8-membered heterocyclic ring; or R$_{10}$ and R$_{11}$ can together form a 5-, 6-, 7-, or 8-membered heterocyclic ring; or
each R$_{11}$ is independently selected from H or alkyl; and pharmaceutically active metabolites, pharmaceutically acceptable solvates, pharmaceutically acceptable salts, or pharmaceutically acceptable prodrugs thereof.

In one embodiment, the compound of Formula (A) has the structure:

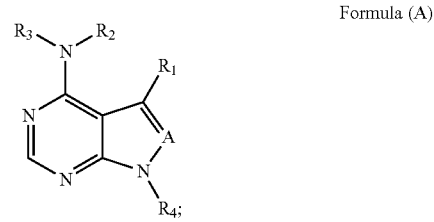

Formula (A)

wherein:
A is N;
R$_2$ and R$_3$ are each H;
R$_1$ is phenyl-O-phenyl or phenyl-S-phenyl; and
R$_4$ is L$_3$-X-L$_4$-G, wherein,
L$_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;
X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;
L$_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;
or L$_3$, X and L$_4$ taken together form a nitrogen containing heterocyclic ring;
G is

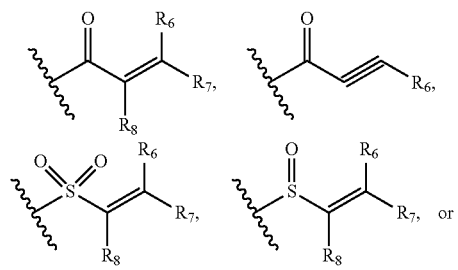

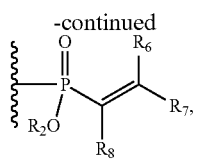

wherein, $R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl.

In some embodiments, the ACK inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib)

Ibrutinib

In some embodiments, the ACK inhibitor is PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13.

In some embodiments, the ACK inhibitor is 4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide (CGI-1746); 7-benzyl-1-(3-(piperidin-1-yl)propyl)-2-(4-(pyridin-4-yl)phenyl)-1H-imidazo[4,5-g]quinoxalin-6(5H)-one (CTA-056); (R)—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide (GDC-0834); 6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one (RN-486); N-[5-[5-(4-acetylpiperazine-1-carbonyl)-4-methoxy-2-methylphenyl]sulfanyl-1,3-thiazol-2-yl]-4-[(3,3-dimethylbutan-2-ylamino)methyl]benzamide (BMS-509744, HY-11092); or N-(5-((5-(4-Acetylpiperazine-1-carbonyl)-4-methoxy-2-methylphenyl)thio)thiazol-2-yl)-4-(((3-methylbutan-2-yl)amino)methyl)benzamide (HY11066).

In some embodiments, the ACK inhibitor is:

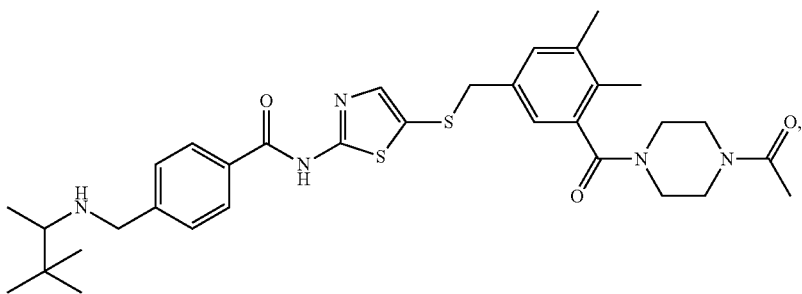

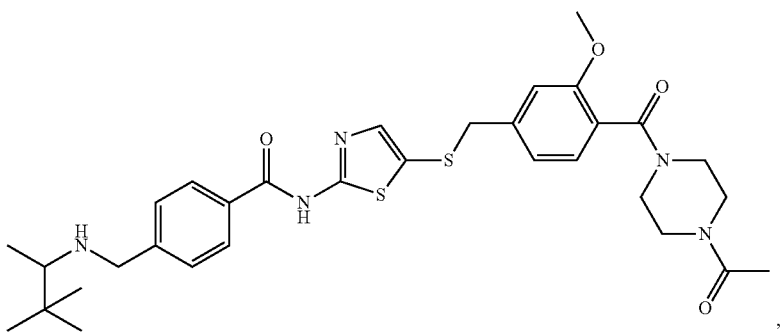

-continued
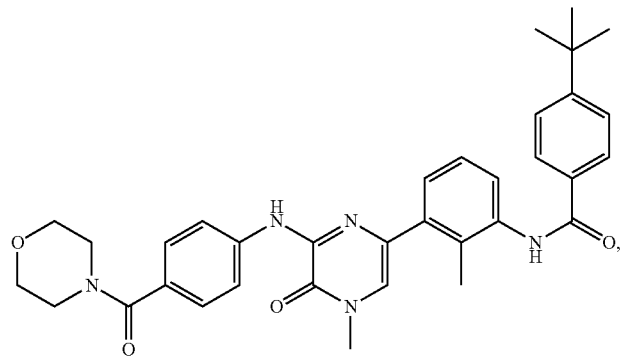
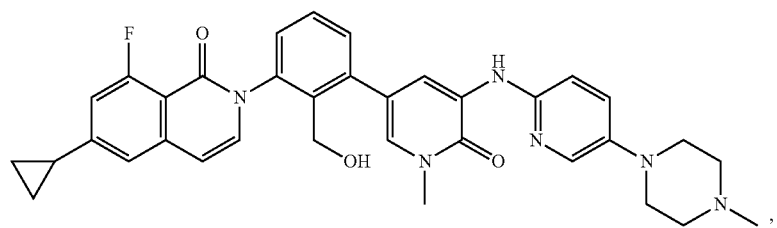
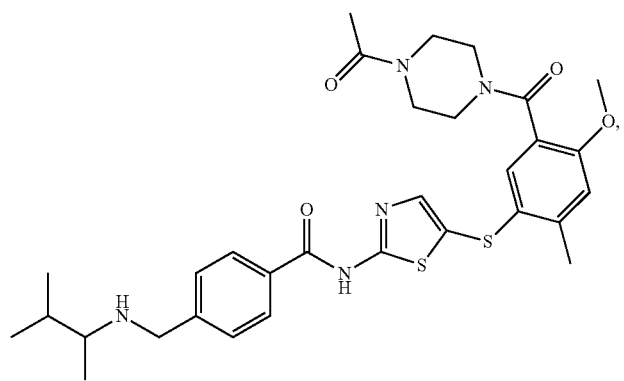
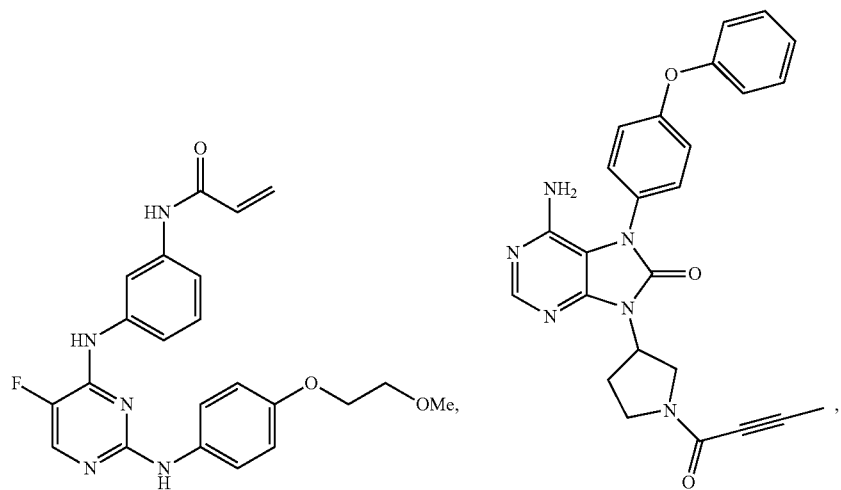

-continued
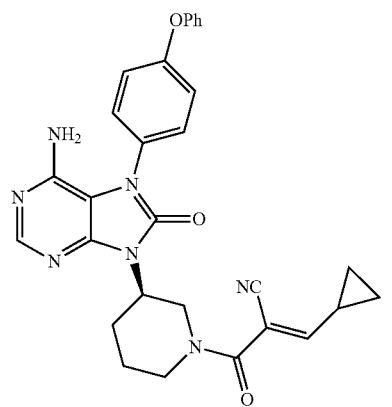
,
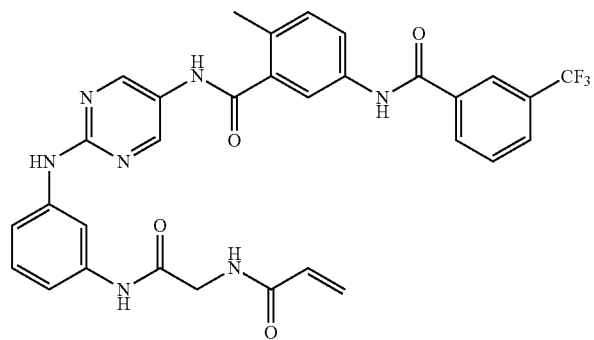
,
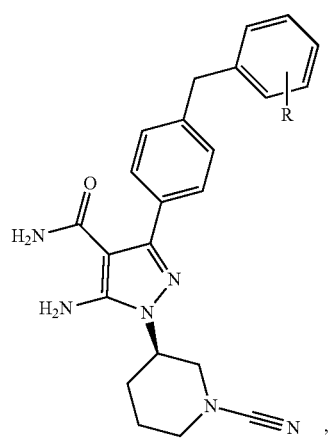
,
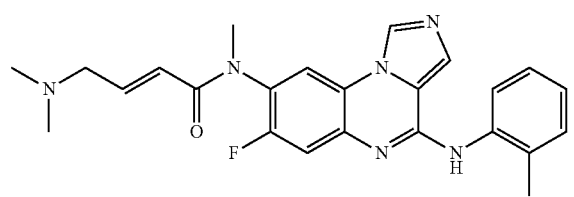
,
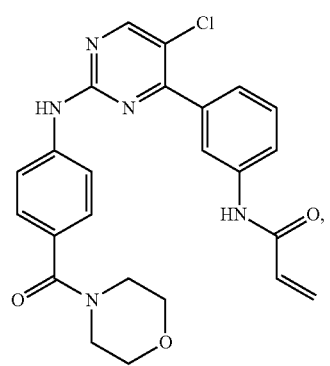
,
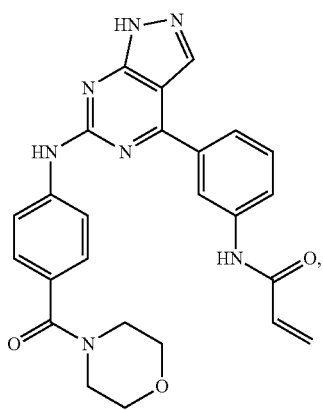
,
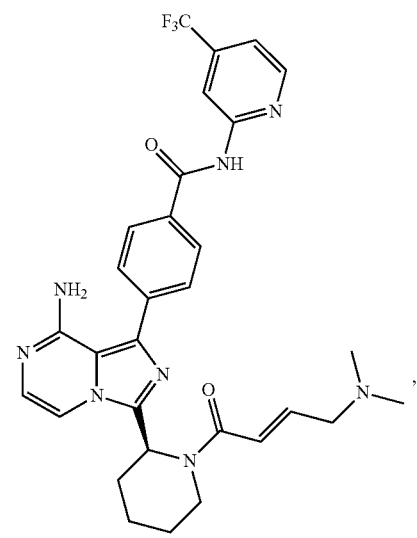
,
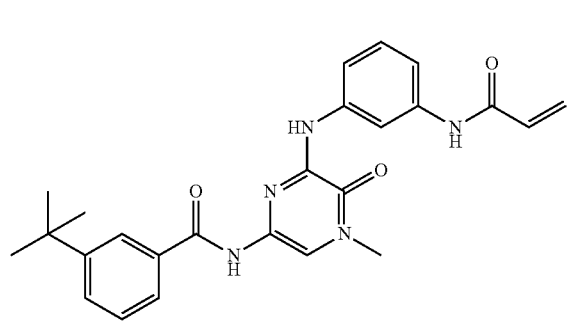
,
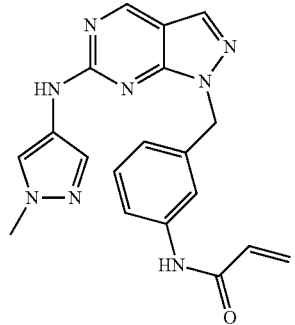
,

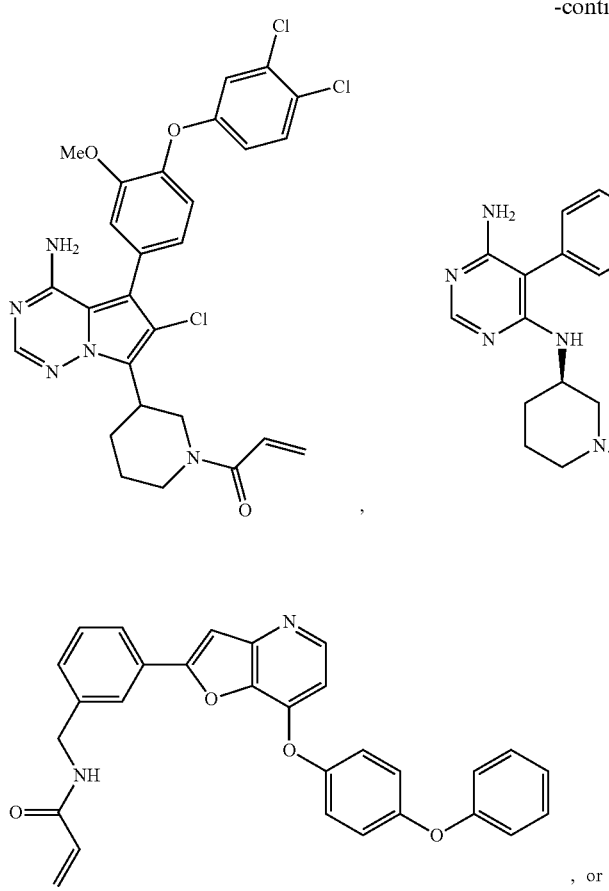

, or

Combination Therapies

Described herein are methods of treating HER2 amplified breast cancer in an individual in need thereof comprising co-administering to the individual a composition comprising a therapeutically-effective amount of an ACK inhibitor compound (e.g., a BTK inhibitor, such as for example ibrutinib) and an additional therapeutic agent. Further described herein are methods of treating HER2 amplified cancer in an individual in need thereof comprising co-administering to the individual a composition comprising a therapeutically-effective amount of an ACK inhibitor compound (e.g., a BTK inhibitor, such as for example ibrutinib) and an additional therapeutic agent. In some embodiments, the ACK inhibitor compound is a BTK inhibitor. In some embodiments, the BTK compound is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13. In some embodiments, the ACK inhibitor compound is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13. In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

In some embodiments, the additional therapeutic agent is an anticancer agent. In some embodiments, the additional therapeutic agent is a chemotherapeutic agent. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents for administration with ibrutinib include compounds used in "targeted therapy" and conventional chemotherapy.

In some embodiments, described herein are methods of treating HER2 amplified breast cancer in an individual in need thereof comprising co-administering to the individual a composition comprising a therapeutically-effective amount of an ACK inhibitor compound and an anticancer agent. In some embodiments, also described herein are methods of treating HER2 amplified cancer in an individual in need thereof comprising co-administering to the individual a composition comprising a therapeutically-effective amount of an ACK inhibitor compound and an anticancer agent.

In some embodiments, described herein are methods of treating HER2 amplified breast cancer in an individual in need thereof comprising co-administering to the individual a composition comprising a therapeutically-effective amount of an ACK inhibitor compound and a chemotherapeutic agent. In some embodiments, also described herein are methods of treating HER2 amplified cancer in an individual in need thereof comprising co-administering to the individual a composition comprising a therapeutically-effective amount of an ACK inhibitor compound and a chemotherapeutic agent. In some embodiments, the ACK inhibitor compound is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13. In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

In some embodiments, described herein are methods of treating HER2 amplified breast cancer in an individual in need thereof comprising co-administering to the individual a composition comprising a therapeutically-effective amount of an ACK inhibitor compound and ibrutinib. In some embodiments, also described herein are methods of treating HER2 amplified cancer in an individual in need thereof comprising co-administering to the individual a composition comprising a therapeutically-effective amount of an ACK inhibitor compound and ibrutinib.

Examples of chemotherapeutic agents for administration with ibrutinib for treatment of a HER2-amplified cancer include, but are not limited to: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine,dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®), and doxorubicin (ADRIAMYCIN@), Akti-1/2, HPPD, rapamycin, and any combinations thereof.

In some embodiments, the additional therapeutic agent for administration with an ACK inhibitor (e.g. a BTK inhibitor, such as for example ibrutinib) for treatment of a HER2-amplified cancer selected from among: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™ SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside (Ara-C); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above and any combinations thereof.

In some embodiments, the additional therapeutic agent for administration with an ACK inhibitor (e.g. a BTK inhibitor, such as for example ibrutinib) for treatment of a HER2-amplified cancer is selected from among (i) anti-hormonal agents that act to regulate or inhibit hormone action on tumors such as antiestrogens and selective estrogen receptor modulators (SERMs), including, for example, tamoxifen (NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above, and any combinations thereof.

In some embodiments, the additional therapeutic agent for administration with an ACK inhibitor (e.g. a BTK inhibitor, such as for example ibrutinib) for treatment of a HER2-amplified cancer selected from among therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug-conjugate, gemtuzumab ozogamicin (MYLOTARG®, Wyeth) and any combinations thereof.

In some embodiments, the additional therapeutic agent for administration with an ACK inhibitor (e.g. a BTK inhibitor, such as for example ibrutinib) for treatment of a HER2-amplified cancer is a humanized monoclonal antibody selected from among: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab. In some embodiments, the additional therapeutic agent is selected from erlotinib, docetaxel, 5-FU, gemcitabine, PD-0325901, cisplatin, carboplatin, paclitaxel, bevacizumab, trastuzumab, pertuzumab, temozolomide, tamoxifen, doxorubicin, Akti-1/2, HPPD, rapamycin, lapatinib, and any combinations thereof.

In some embodiments, the additional chemotherapeutic agent for administration with an AKT inhibitor (e.g. a BTK inhibitor, such as for example ibrutinib) for treatment of a HER2-amplified cancer is selected from among an antibody, a B cell receptor pathway inhibitor, a T cell receptor inhibitor, a PI3K inhibitor, an IAP inhibitor, an mTOR inhibitor, a radioimmunotherapeutic, a DNA damaging agent, a proteasome inhibitor, a histone deacetylase (HDCA) inhibitor, a protein kinase inhibitor, an IRAK inhibitor, a hedgehog inhibitor, an Hsp90 inhibitor, a telomerase inhibitor, a Jak1/2 inhibitor (e.g., ruxolitinib, baricitinib, CYT387, lestauritinib, pacritinib, TG101348, SAR302503, tofacitinib (Xeljanz), etanercept (Enbrel), GLPG0634, R256), a protease inhibitor, a PKC inhibitor, a PARP inhibitor, a proteosome inhibitor, a CYP3A4 inhibitor, an AKT inhibitor, an Erk inhibitor, an alkylating agent, an anti metabolite, a plant alkaloid, a terpenoid, a cytotoxin, a topoisomerase inhibitor, or a combination thereof. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, a CD22 inhibitor, a Bcl-2 inhibitor, an IRAK 1/4 inhibitor, a microtubule inhibitor, a Topo II inhibitor, anti TWEAK, anti-IL17 bispecific antibody, a CK2 inhibitor, anaplastic lymphoma kinase (ALK) and c-Met inhibitors, a T cell receptor inhibitor is Muromonab-CD3, demethylase enzyme inhibitors such as demethylase, HDM, LSDI and KDM, fatty acid synthase inhibitors such as spirocyclic piperidine derivatives, glucocorticosteroid receptor agonist, fusion anti-CD 19-cytotoxic agent conjugate, antimetabolite, p70S6K inhibitor, immune modulators, AKT/PKB inhibitor, procaspase-3 activator PAC-1, BRAF inhibitor, lactate dehydrogenase A (LDH-A) inhibitor, CCR2 inhibitor, CXCR4 inhibitor, chemokine receptor antagonists, DNA double stranded break repair inhibitors, NOR202, GA-101, TLR2 inhibitor, and any combinations thereof.

In some embodiments, the additional therapeutic agent for administration with an ACK inhibitor for treatment of a HER2-amplified cancer is an anti-HER2 therapeutic agent. In some embodiments, the additional therapeutic agent for administration with an ACK inhibitor for treatment of a HER2-amplified cancer is a kinase inhibitor. In some embodiments, the additional therapeutic agent for administration with an ACK inhibitor for treatment of a HER2-amplified cancer is selected from the group consisting of: trastuzumab, trastuzumab emtansine, pertuzumab, lapatinib, and MM-111 (Merrimack Pharmaceuticals). In some embodiments, the additional therapeutic agent for administration with an ACK inhibitor for treatment of a HER2-amplified cancer is trastuzumab. In some embodiments, the additional therapeutic agent for administration with an ACK inhibitor for treatment of a HER2-amplified cancer is trastuzumab emtansine. In some embodiments, the additional therapeutic agent for administration with an ACK inhibitor for treatment of a HER2-amplified cancer is lapatinib. In some embodiments, the additional therapeutic agent for administration with an ACK inhibitor for treatment of a HER2-amplified cancer is pertuzumab. In some embodiments, the additional therapeutic agent for administration with an ACK inhibitor for treatment of a HER2-amplified cancer is MM-111. In some embodiments, the ACK inhibitor is a BTK inhibitor. In some embodiments, the ACK inhibitor compound is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13. In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

In some embodiments, the additional therapeutic agent for administration with ibrutinib for treatment of a HER2-amplified cancer is an anti-HER2 therapeutic agent. In some embodiments, the additional therapeutic agent for administration with ibrutinib for treatment of a HER2-amplified cancer is a kinase inhibitor. In some embodiments, the additional therapeutic agent for administration with ibrutinib for treatment of a HER2-amplified cancer is selected from the group consisting of: trastuzumab, trastuzumab emtansine, pertuzumab, lapatinib, and MM-111 (Merrimack Pharmaceuticals). In some embodiments, the additional therapeutic agent for administration with ibrutinib for treatment of a HER2-amplified cancer is trastuzumab. In some embodiments, the additional therapeutic agent for administration with ibrutinib for treatment of a HER2-amplified cancer is trastuzumab emtansine. In some embodiments, the additional therapeutic agent for administration with ibrutinib for treatment of a HER2-amplified cancer is lapatinib. In some embodiments, the additional therapeutic agent for administration with ibrutinib for treatment of a HER2-amplified cancer is pertuzumab. In some embodiments, the additional therapeutic agent for administration with ibrutinib for treatment of a HER2-amplified cancer is MM-111.

In some embodiments, the additional therapeutic agent for administration with an ACK inhibitor for treatment of a HER2-amplified cancer is pan-ErbB inhibitor. In some embodiments, the additional therapeutic agent for administration with an ACK inhibitor for treatment of a HER2-amplified cancer is selected from the group consisting of: afatinib, neratinib, and dacomitinib. In some embodiments, the additional therapeutic agent for administration with an ACK inhibitor for treatment of a HER2-amplified cancer is afatinib. In some embodiments, the additional therapeutic agent for administration with an ACK inhibitor for treatment of a HER2-amplified cancer is neratinib. In some embodiments, the additional therapeutic agent for administration with an ACK inhibitor for treatment of a HER2-amplified cancer is dacomitinib. In some embodiments, the ACK inhibitor is a BTK inhibitor. In some embodiments, the ACK inhibitor compound is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13. In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

In some embodiments, the additional therapeutic agent for administration with ibrutinib for treatment of a HER2-amplified cancer is pan-ErbB inhibitor. In some embodiments, the additional therapeutic agent for administration with ibrutinib for treatment of a HER2-amplified cancer is selected from the group consisting of: afatinib, neratinib, and dacomitinib. In some embodiments, the additional therapeutic agent for administration with ibrutinib for treatment of a HER2-amplified cancer is afatinib. In some embodiments, the additional therapeutic agent for administration with ibrutinib for treatment of a HER2-amplified cancer is neratinib. In some embodiments, the additional therapeutic agent for administration with ibrutinib for treatment of a HER2-amplified cancer is dacomitinib.

In some embodiments, the additional therapeutic agent for administration with an ACK inhibitor for treatment of a HER2-amplified cancer is an anti-VEGF therapeutic agent. In some embodiments, the additional therapeutic agent for administration with an ACK inhibitor for treatment of a HER2-amplified cancer is selected from the group consisting of: bevacizumab, ranibizumab, lapatinib, sunitinib, sorafenib, axitinib, and pazopanib. In some embodiments, the additional therapeutic agent for administration with an ACK inhibitor for treatment of a HER2-amplified cancer is bevacizumab. In some embodiments, the additional therapeutic agent for administration with an ACK inhibitor for treatment of a HER2-amplified cancer is ranibizumab. In some embodiments, the additional therapeutic agent for administration with an ACK inhibitor for treatment of a HER2-amplified cancer is lapatinib. In some embodiments, the additional therapeutic agent for administration with an ACK inhibitor for treatment of a HER2-amplified cancer is sunitinib. In some embodiments, the additional therapeutic agent for administration with an ACK inhibitor for treatment of a HER2-amplified cancer is sorafenib. In some embodiments, the additional therapeutic agent for administration with an ACK inhibitor for treatment of a HER2-amplified cancer is axitinib. In some embodiments, the additional therapeutic agent for administration with an ACK inhibitor for treatment of a HER2-amplified cancer is pazopanib. In some embodiments, the ACK inhibitor is a BTK inhibitor. In some embodiments, the ACK inhibitor compound is selected from among ibrutinib (PCI-32765), PCI-45292, PCI-45466, AVL-101/CC-101 (Avila Therapeutic s/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13. In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

In some embodiments, the additional therapeutic agent for administration with ibrutinib for treatment of a HER2-amplified cancer is an anti-VEGF therapeutic agent. In some embodiments, the additional therapeutic agent for administration with ibrutinib for treatment of a HER2-amplified cancer is selected from the group consisting of: bevacizumab, ranibizumab, lapatinib, sunitinib, sorafenib, axitinib, and pazopanib. In some embodiments, the additional therapeutic agent for administration with ibrutinib for treatment of a HER2-amplified cancer is bevacizumab. In some embodiments, the additional therapeutic agent for administration with ibrutinib for treatment of a HER2-amplified cancer is ranibizumab. In some embodiments, the additional therapeutic agent for administration with ibrutinib for treatment of a HER2-amplified cancer is lapatinib. In some embodiments, the additional therapeutic agent for administration with ibrutinib for treatment of a HER2-amplified cancer is sunitinib. In some embodiments, the additional therapeutic agent for administration with ibrutinib for treatment of a HER2-amplified cancer is sorafenib. In some embodiments, the additional therapeutic agent for administration with ibrutinib for treatment of a HER2-amplified cancer is axitinib. In some embodiments, the additional therapeutic agent for administration with ibrutinib for treatment of a HER2-amplified cancer is pazopanib.

In some embodiments, the additional therapeutic agent for administration with an ACK inhibitor for treatment of a HER2-amplified cancer is selected from the group consisting of: temsirolimus, paclitaxel, ASLAN001 (also, ARRY-543, ASLAN Pharmaceuticals), vorinostat, doxorubicin, cyclophosphamide, cisplatin, docetaxel, and dasatinib. In some embodiments, the additional therapeutic agent for administration with an ACK inhibitor for treatment of a HER2-amplified cancer is docetaxel. In some embodiments, the additional therapeutic agent for administration with an ACK inhibitor for treatment of a HER2-amplified cancer is paclitaxal. In some embodiments, the additional therapeutic agent for administration with an ACK inhibitor for treatment of a HER2-amplified cancer is doxorubicin. In some embodiments, the ACK inhibitor is a BTK inhibitor. In some embodiments, the ACK inhibitor compound is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13. In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

In some embodiments, the additional therapeutic agent for administration with ibrutinib for treatment of a HER2-amplified cancer is selected from the group consisting of: temsirolimus, paclitaxel, ASLAN001 (also, ARRY-543, ASLAN Pharmaceuticals), vorinostat, doxorubicin, cyclophosphamide, cisplatin, docetaxel, and dasatinib. In some embodiments, the additional therapeutic agent for administration with ibrutinib for treatment of a HER2-amplified cancer is docetaxel. In some embodiments, the additional therapeutic agent for administration with ibrutinib for treatment of a HER2-amplified cancer is paclitaxal. In some embodiments, the additional therapeutic agent for administration with ibrutinib for treatment of a HER2-amplified cancer is doxorubicin.

In some embodiments, the additional therapeutic agent for administration with an ACK inhibitor for treatment of a HER2-amplified cancer is trastuzumab and docetaxel. In some embodiments, the ACK inhibitor is a BTK inhibitor. In some embodiments, the ACK inhibitor compound is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13. In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib). In some embodiments, the additional therapeutic agent for administration with ibrutinib for treatment of a HER2-amplified cancer is trastuzumab and docetaxel.

In some embodiments, the additional therapeutic agent for administration with an ACK inhibitor for treatment of a HER2-amplified cancer is pertuzumab and docetaxel. In some embodiments, the ACK inhibitor is a BTK inhibitor. In some embodiments, the ACK inhibitor compound is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13. In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib). In some embodiments, the additional therapeutic agent for administration with ibrutinib for treatment of a HER2-amplified cancer is pertuzumab and docetaxel.

In some embodiments, the additional therapeutic agent for administration with an ACK inhibitor for treatment of a HER2-amplified cancer is doxorubicin, cyclophosphamide and paclitaxal. In some embodiments, the ACK inhibitor is a BTK inhibitor. In some embodiments, the ACK inhibitor compound is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13. In some embodiments, the additional therapeutic agent for administration with ibrutinib for treatment of a HER2-amplified cancer is doxorubicin, cyclophosphamide and paclitaxal.

In some embodiments, the additional therapeutic agent for administration with an ACK inhibitor for treatment of a HER2-amplified cancer is doxorubicin, cyclophosphamide and 5-FU. In some embodiments, the ACK inhibitor is a BTK inhibitor. In some embodiments, the ACK inhibitor compound is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13. In some embodiments, the additional therapeutic agent for administration with ibrutinib for treatment of a HER2-amplified cancer is doxorubicin, cyclophosphamide and 5-FU.

In some embodiments, the additional therapeutic agent for administration with ibrutinib for treatment of a HER2-amplified cancer is a histone deacetylase (HDAC) inhibitor. In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat).

As described elsewhere herein, in some embodiments, the HER2-amplified cancer is selected from the group consisting of: breast, colon, endometrial, cervical, urothelial, lung (including, non-small cell lung cancer), ovarian, gastric, gastroesophageal junction (GEJ), head and neck, biliary tract, prostate, and pancreatic cancer. In some embodiments, the HER2-amplified cancer is HER2-amplified breast cancer. In some embodiments, the HER2-amplified cancer is HER2-amplified colon cancer. In some embodiments, the HER2-amplified cancer is HER2-amplified endometrial cancer. In some embodiments, the HER2-amplified cancer is HER2-amplified cervical cancer. In some embodiments, the HER2-amplified cancer is HER2-amplified urothelial cancer. In some embodiments, the HER2-amplified cancer is HER2-amplified lung cancer. In some embodiments, the HER2-amplified lung cancer is HER2-amplified non-small cell lung cancer. In some embodiments, the HER2-amplified cancer is HER2-amplified ovarian cancer. In some embodiments, the HER2-amplified cancer is HER2-amplified gastric cancer. In some embodiments, the HER2-amplified cancer is HER2-amplified gastroesophageal junction (GEJ) cancer. In some embodiments, the HER2-amplified cancer is HER2-amplified head and neck cancer. In some embodiments, the HER2-amplified cancer is HER2-amplified biliary tract cancer. In some embodiments, the HER2-amplified cancer is HER2-amplified prostate cancer. In some embodiments, the HER2-amplified cancer is HER2-amplified pancreatic cancer. In some embodiments, the HER2-amplified cancer is metastatic. In some embodiments, the HER2-amplified cancer has metastasized to the brain. In some embodiments, the HER2-amplified cancer has a HER2:CEP17 ratio >4.0. In some embodiments, the HER2-amplified cancer has a HER2:CEP17 ratio of 2.2-4.0. In some embodiments, the HER2-amplified cancer is graded 3+ using IHC. In some embodiments, the HER2-amplified cancer is refractory to treatment. In some embodiments, the treatment to which the HER2-amplified cancer is refractory is selected from: trastuzumab, trastuzumab emtansine, pertuzumab, lapatinib, or MM-111. In some embodiments, the treatment to which the HER2-amplified cancer is refractory is trastuzumab. In some embodiments, the HER2-amplified cancer is recurrent.

When an additional agent is co-administered with an ACK inhibitor, the additional agent and the ACK inhibitor do not have to be administered in the same pharmaceutical composition, and are optionally, because of different physical and chemical characteristics, administered by different routes. The initial administration is made, for example, according to established protocols, and then, based upon the observed effects, the dosage, modes of administration and times of administration are modified.

By way of example only, if a side effect experienced by an individual upon receiving an ACK inhibitor is nausea, then it is appropriate to administer an anti-emetic agent in combination with the ACK inhibitor.

Or, by way of example only, the therapeutic effectiveness of an ACK inhibitor described herein is enhanced by administration of an adjuvant (i.e., by itself the adjuvant has minimal therapeutic benefit, but in combination with another therapeutic agent, the overall therapeutic benefit to the patient is enhanced). Or, by way of example only, the benefit experienced by an individual is increased by administering an ACK inhibitor described herein with another therapeutic agent (which also includes a therapeutic regimen) that also has therapeutic benefit. In any case, regardless of the disease, disorder being treated, the overall benefit experienced by the patient is in some embodiments simply additive of the two therapeutic agents or in other embodiments, the patient experiences a synergistic benefit.

The particular choice of compounds used will depend upon the diagnosis of the attending physicians and their judgment of the condition of the patient and the appropriate treatment protocol. The compounds are optionally administered concurrently (e.g., simultaneously, essentially simultaneously or within the same treatment protocol) or sequentially, depending upon the nature of the disorder, the condition of the patient, and the actual choice of compounds used. The determination of the order of administration, and the number of repetitions of administration of each therapeutic agent during a treatment protocol, is based on an evaluation of the disease being treated and the condition of the patient.

In some embodiments, therapeutically-effective dosages vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disorder being treated and so forth. In addition, when co-administered with an additional therapeutic agent, an ACK inhibitor described herein is administered either simultaneously with the additional therapeutic agent, or sequentially. If administered sequentially, the attending physician will decide on the appropriate sequence of administering protein in combination with the biologically active agent(s).

If the additional therapeutic agent and the ACK inhibitor are administered simultaneously, the multiple therapeutic agents are optionally provided in a single, unified form, or in multiple forms (by way of example only, either as a single pill or as two separate pills). In some embodiments, one of the therapeutic agents is given in multiple doses, or both are given as multiple doses. If not simultaneously, the timing between the multiple doses is from about more than zero weeks to less than about four weeks. In addition, the combination methods, compositions and formulations are not to be limited to the use of only two agents; the use of multiple therapeutic combinations is also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

In some embodiments, the pharmaceutical agents which make up the combination therapy disclosed herein are administered in a combined dosage form, or in separate dosage forms intended for substantially simultaneous administration. In some embodiments, the pharmaceutical agents that make up the combination therapy are administered sequentially, with either therapeutic compound being administered by a regimen calling for two-step administration. In some embodiments, the two-step administration regimen calls for sequential administration of the active agents or spaced-apart administration of the separate active agents. The time period between the multiple administration steps ranges from a few minutes to several hours, depending upon the properties of each pharmaceutical agent, such as potency, solubility, bioavailability, plasma half-life and kinetic profile of the pharmaceutical agent. In some embodiments, circadian variation of the target molecule concentration determines the optimal dose interval.

In some embodiments, the ACK inhibitor compound and the additional therapeutic agent are administered in a unified dosage form. In some embodiments, the ACK inhibitor compound and the additional therapeutic agent are administered in separate dosage forms. In some embodiments, the ACK inhibitor compound and the additional therapeutic agent are administered simultaneously or sequentially.

Pharmaceutical Compositions/Formulations

Disclosed herein, in certain embodiments, are compositions comprising a therapeutically effective amount of an ACK inhibitor compound, and a pharmaceutically acceptable excipient. In some embodiments, the ACK inhibitor compound (e.g., a BTK inhibitor, such as for example ibrutinib) is a compound of Formula (A). In some embodiments, the ACK inhibitor compound is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13. In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

Pharmaceutical compositions of ACK inhibitor compound (e.g., a BTK inhibitor, such as for example ibrutinib) are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

A pharmaceutical composition, as used herein, refers to a mixture of an ACK inhibitor compound (e.g., a BTK inhibitor, such as for example ibrutinib) with other chemical components, such as carriers, stabilizers, diluents, dispersing agents, suspending agents, thickening agents, and/or excipients.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

Pharmaceutical compositions are optionally manufactured in a conventional manner, such as, by way of example only, by means of conventional mixing, dissolving, granulating, dragee-making, levigating, emulsifying, encapsulating, entrapping or compression processes.

The pharmaceutical formulations described herein are administered by any suitable administration route, including but not limited to, oral, parenteral (e.g., intravenous, subcutaneous, intramuscular), intranasal, buccal, topical, rectal, or transdermal administration routes.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the compositions are formulated into capsules. In some embodiments, the compositions are formulated into solutions (for example, for IV administration).

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

In some embodiments, the pharmaceutical compositions are formulated such that the amount of the ACK inhibitor (e.g., a BTK inhibitor, such as for example ibrutinib) in each unit dosage form is about 140 mg per day.

Dosage Forms

The compositions described herein can be formulated for administration to a subject via any conventional means including, but not limited to, oral, parenteral (e.g., intravenous, subcutaneous, or intramuscular), buccal, intranasal, rectal or transdermal administration routes. In some embodiments, the composition is formulated for administration in a separate dosage form. In some embodiments, the composition is formulated for administration in a combined dosage form.

In some embodiments, the pharmaceutical compositions described herein, which include ibrutinib and/or an additional therapeutic agent can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of ibrutinib and/or an anticancer agent, with one or more pharmaceutical excipients to form a bulk blend composition. When referring to these bulk blend compositions as homogeneous, it is meant that the particles of ibrutinib and/or an additional therapeutic agent, are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of ibrutinib and/or an anticancer agent. In another embodiment, some or all of the particles of ibrutinib and/or an anticancer agent, are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of ibrutinib and/or an additional therapeutic agent, from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®, and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxypropylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of ibrutinib or the second agent, from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of ibrutinib or an additional therapeutic agent, described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of ibrutinib and/or an additional therapeutic agent, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with ibrutinib and/or an additional therapeutic agent, which sufficiently isolate the compound of any of ibrutinib or an additional therapeutic agent, from other non-compatible excipients. Materials compatible with compounds of any of ibrutinib or an additional therapeutic agent, are those that delay the release of the compounds of any of ibrutinib or an additional therapeutic agent, in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® 5100, Eudragit® RD100, Eudragit® E100, Eudragit® L12.5, Eudragit® 512.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds of any of ibrutinib or an additional therapeutic agent may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of compounds of any of ibrutinib or an additional therapeutic agent are microencapsulated prior to being formulated into one of the above forms. In still another embodiment, some or most of the particles are coated prior to being further formulated by using standard coating procedures, such as those described in *Remington's Pharmaceutical Sciences*, 20th Edition (2000).

In other embodiments, the solid dosage formulations of the compounds of any of ibrutinib and/or an additional therapeutic agent are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with a compound of any of ibrutinib and/or an anti-cancer agent, described herein, may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH >7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH >6. Aquateric (FMC) is an aqueous based system and is a spray dried CAP psuedolatex with particles <1 µm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-555, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions; Poly Vinyl Acetate Phthalate (PVAP). PVAP dissolves in pH >5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include ibrutinib and/or an additional therapeutic agent, are delivered using a pulsatile dosage form. A pulsatile dosage form is capable of providing one or more immediate release pulses at predetermined time points after a controlled lag time or at specific sites. Many other types of controlled release systems known to those of ordinary skill in the art and are suitable for use with the formulations described herein. Examples of such delivery systems include, e.g., polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983.

In some embodiments, pharmaceutical formulations are provided that include particles of ibrutinib and/or an additional therapeutic agent, described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, $2^{nd}$ Ed., pp. 754-757 (2002). In addition the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116,817 and 6,391,452, each of which is specifically incorporated by reference. Formulations that include ibrutinib and/or an additional therapeutic agent, which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. The nasal dosage form should be isotonic with nasal secretions.

For administration by inhalation described herein may be in a form as an aerosol, a mist or a powder. Pharmaceutical compositions described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal Formulations

Buccal formulations may be administered using a variety of formulations known in the art. For example, such formulations include, but are not limited to, U.S. Pat. Nos. 4,229,447, 4,596,795, 4,755,386, and 5,739,136, each of which is specifically incorporated by reference. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with ibrutinib and/or an additional therapeutic agent, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The transdermal dosage forms described herein may incorporate certain pharmaceutically acceptable excipients which are conventional in the art. In one embodiments, the transdermal formulations described herein include at least three components: (1) a formulation of a compound of ibrutinib and an additional therapeutic agent; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of ibrutinib and an additional therapeutic agent. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Injectable Formulations

Formulations that include a compound of ibrutinib and/or an additional therapeutic agent, suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Other Formulations

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Diagnostic Methods

Disclosed herein are methods of using biomarkers for stratification of patients, for monitoring the progression of a treatment, or for optimization of a therapeutic regimen. In some embodiments, the biomarkers are evaluated based on the presence or absence of modifications or mutations in the biomarkers, or by expression level. In some embodiments, the biomarkers include heregulin. In some embodiments, the treatment or therapeutic regimen comprises a combination of an ACK inhibitor and an additional therapeutic agent. In some embodiments, the additional therapeutic agent is an anti-HER2 therapeutic agent, a pan-ErbB inhibitor, or an anti-VEGF therapeutic agent. In some embodiments, the anti-HER2 therapeutic agent is selected from trastuzumab, trastuzumab emtansine, pertuzumab, lapatinib, or MM-111. In some embodiments, the pan-ErbB inhibitor is selected from afatinib, neratinib, and dacomitinib. In some embodiments, the anti-VEGF therapeutic agent is selected from bevacizumab, ranibizumab, lapatinib, sunitinib, sorafenib, axitinib, and pazopanib. In some embodiments, the additional therapeutic agent is selected from temsirolimus, paclitaxel, ASLAN001 (also, ARRY-543, ASLAN Pharmaceuticals), vorinostat, doxorubicin, cyclophosphamide, cisplatin, docetaxel, and dasatinib. In some embodiments, the additional therapeutic agent is selected from trastuzumab and docetaxel; pertuzumab and docetaxel; doxorubicin, cyclophosphamide, and paclitaxal; or doxorubicin, cyclophosphamide, and 5-FU. In some embodiments, the ACK inhibitor is a BTK inhibitor. In some embodiments, the ACK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) and LFM-A13. In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib). In some embodiments, HRG induces resistance in HER2-amplified tumor. In some embodiments, ibrutinib sensitizes HRG-induced resistant breast cancer cells. In some embodiments, elevated levels of ibrutinib sensitize HRG-induced resistant breast cancer cells. In some embodiments, the breast cancer cells include cells from the BT-474 and MDA-MB-453 cell lines.

In some embodiments, the expression level of heregulin is 0.5-fold, 1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 15-fold, 20-fold, 50-fold, 75-fold, 100-fold, 200-fold, 500-fold, 1000-fold, or more compared to the reference level of heregulin. In some embodiments, the expression level of heregulin is 0.5-fold, 1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 15-fold, 20-fold, 50-fold, 75-fold, 100-fold, 200-fold, 500-fold, 1000-fold, or less compared to the reference level of heregulin.

In some embodiments, the reference level is the expression level of heregulin in an individual who does not have HER2 amplified tumor. In some embodiments, the reference level is the expression level of heregulin in an individual prior to treatment with a combination of an ACK inhibitor and an additional therapeutic agent.

Methods for determining the expression level or the presence of biomarkers such as heregulin are well known in the art, for example, by ELISA, radioimmunoassay (RIA), electrochemiluminescence (ECL), Western blot, multiplexing technologies, or other similar methods. Cell surface expression of biomarkers are measured, for example, by flow cytometry, immunohistochemistry, Western Blot, immunoprecipitation, magnetic bead selection, and quantification of cells expressing either of these cell surface markers. Biomarker RNA expression levels could be measured by RT-PCR, Qt-PCR, microarray, Northern blot, or other similar technologies.

As disclosed herein, determining the expression or presence of the biomarker of interest at the protein or nucleotide level is accomplished using any detection method known to those of skill in the art. By "detecting expression" or "detecting the level of is intended determining the expression level or presence of a biomarker protein or gene in the biological sample. Thus, "detecting expression" encompasses instances where a biomarker is determined not to be expressed, not to be detectably expressed, expressed at a low level, expressed at a normal level, or overexpressed.

In certain aspects of the method provided herein, the tumor samples are isolated, detected or measured. In certain embodiments, the tumor samples are isolated, detected or measured using immunophenotyping techniques. In other embodiments, the tumor samples are isolated, detected or measured using fluorescence activated cell sorting (FACS) techniques.

In certain aspects, the expression or presence of these various biomarkers and any clinically useful prognostic markers in a biological sample are detected at the protein or nucleic acid level, using, for example, immunohistochemistry techniques or nucleic acid-based techniques such as in situ hybridization and RT-PCR. In one embodiments, the expression or presence of one or more biomarkers is carried out by a means for nucleic acid amplification, a means for nucleic acid sequencing, a means utilizing a nucleic acid microarray (DNA and RNA), or a means for in situ hybridization using specifically labeled probes.

In other embodiments, determining the expression or presence of one or more biomarkers is carried out through gel electrophoresis. In one embodiment, the determination is carried out through transfer to a membrane and hybridization with a specific probe.

In other embodiments, the determining the expression or presence of one or more biomarkers carried out by a diagnostic imaging technique.

In still other embodiments, the determining the expression or presence of one or more biomarkers carried out by a detectable solid substrate. In one embodiment, the detectable solid substrate is paramagnetic nanoparticles functionalized with antibodies.

In some embodiments, expression level of a biomarker protein of interest in a biological sample is detected by means of a binding protein capable of interacting specifically with that biomarker protein or a biologically active variant thereof. In some embodiments, labeled antibodies, binding portions thereof, or other binding partners are used. The word "label" when used herein refers to a detectable compound or composition that is conjugated directly or indirectly to the antibody so as to generate a "labeled" antibody. In some embodiments, the label is detectable by itself (e.g., radioisotope labels or fluorescent labels) or, in the case of an enzymatic label, catalyzes chemical alteration of a substrate compound or composition that is detectable.

The antibodies for detection of a biomarker protein are either monoclonal or polyclonal in origin, or are synthetically or recombinantly produced. The amount of complexed protein, for example, the amount of biomarker protein associated with the binding protein, for example, an antibody that specifically binds to the biomarker protein, is determined using standard protein detection methodologies known to those of skill in the art. A detailed review of immunological assay design, theory and protocols are found in numerous texts in the art (see, for example, Ausubel et al., eds. (1995) Current Protocols in Molecular Biology) (Greene Publishing and Wiley-Interscience, NY)); Coligan et al., eds. (1994) Current Protocols in Immunology (John Wiley & Sons, Inc., New York, N.Y.).

The choice of marker used to label the antibodies will vary depending upon the application. However, the choice of the marker is readily determinable to one skilled in the art. These labeled antibodies are used in immunoassays as well as in histological applications to detect the presence of any biomarker or protein of interest. The labeled antibodies are either polyclonal or monoclonal. Further, the antibodies for use in detecting a protein of interest are labeled with a radioactive atom, an enzyme, a chromophoric or fluorescent moiety, or a colorimetric tag as described elsewhere herein. The choice of tagging label also will depend on the detection limitations desired. Enzyme assays (ELISAs) typically allow detection of a colored product formed by interaction of the enzyme-tagged complex with an enzyme substrate. Radionuclides that serve as detectable labels include, for example, I-131, I-123, I-125, Y-90, Re-188, Re-186, At-211, Cu-67, Bi-212, and Pd-109. Examples of enzymes that serve as detectable labels include, but are not limited to, horseradish peroxidase, alkaline phosphatase, beta-galactosidase, and glucose-6-phosphate dehydrogenase. Chromophoric moieties include, but are not limited to, fluorescein and rhodamine. The antibodies are conjugated to these labels by methods known in the art. For example, enzymes and chromophoric molecules are conjugated to the antibodies by means of coupling agents, such as dialdehydes, carbodiimides, dimaleimides, and the like. Alternatively, conjugation occurs through a ligand-receptor pair. Examples of suitable ligand-receptor pairs are biotin-avidin or biotin-streptavidin, and antibody-antigen.

In certain embodiments, expression or presence of the biomarkers disclosed herein is determined by radioimmunoassays or enzyme-linked immunoassays (ELISAs), competitive binding enzyme-linked immunoassays, dot blot (see, for example, Promega Protocols and Applications Guide, Promega Corporation (1991), Western blot (see, for example, Sambrook et al. (1989) Molecular Cloning, A Laboratory Manual, Vol. 3, Chapter 18 (Cold Spring Harbor Laboratory Press, Plainview, N.Y.), chromatography such as high performance liquid chromatography (HPLC), or other assays known in the art. Thus, the detection assays involve steps such as, but not limited to, immunoblotting, immunodiffusion, immunoelectrophoresis, or immunoprecipitation.

In some embodiments, the expression or presence of the biomarkers described herein are also determined at the nucleic acid level. Nucleic acid-based techniques for assessing expression are well known in the art and include, for example, determining the level of biomarker mRNA in a biological sample. Many expression detection methods use isolated RNA. Any RNA isolation technique that does not select against the isolation of mRNA is utilized for the purification of RNA (see, e.g., Ausubel et al., ed. (1987-1999) Current Protocols in Molecular Biology (John Wiley & Sons, New York). Additionally, large numbers of tissue samples are readily processed using techniques well known to those of skill in the art, such as, for example, the single-step RNA isolation process disclosed in U.S. Pat. No. 4,843,155.

Thus, in some embodiments, the detection of a biomarker or other protein of interest is assayed at the nucleic acid level using nucleic acid probes. The term "nucleic acid probe" refers to any molecule that is capable of selectively binding to a specifically intended target nucleic acid molecule, for example, a nucleotide transcript. Probes are synthesized by one of skill in the art, or derived from appropriate biological preparations. Probes are specifically designed to be labeled, for example, with a radioactive label, a fluorescent label, an enzyme, a chemiluminescent tag, a colorimetric tag, or other labels or tags that are discussed above or that are known in the art. Examples of molecules that are utilized as probes include, but are not limited to, RNA and DNA.

For example, isolated mRNA are used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that hybridize to the mRNA encoded by the gene being detected. The nucleic acid probe comprises of, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker, biomarker described herein above. Hybridization of an mRNA with the probe indicates that the biomarker or other target protein of interest is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in a gene chip array. A skilled artisan readily adapts known mRNA detection methods for use in detecting the level of mRNA encoding the biomarkers or other proteins of interest.

An alternative method for determining the level of an mRNA of interest in a sample involves the process of nucleic acid amplification, e.g., by RT-PCR (see, for example, U.S. Pat. No. 4,683,202), ligase chain reaction (Barany (1991) Proc. Natl. Acad. Sci. USA 88:189 193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression is assessed by quantitative fluorogenic RT-PCR (i.e., the TaqMan System).

Expression levels of an RNA of interest are monitored using a membrane blot (such as used in hybridization analysis such as Northern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934. The detection of expression also comprises using nucleic acid probes in solution.

In one embodiment of the invention, microarrays are used to determine expression or presence of one or more biomarkers. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, U.S. Pat. Nos. 6,040,138, 5,800,992 and 6,020,135, 6,033,860, and 6,344,316. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261. In some embodiments, an array is fabricated on a surface of virtually any shape or even a multiplicity of surfaces. In some embodiments, an array is a planar array surface. In some embodiments, arrays include peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992. In some embodiments, arrays are packaged in such a manner as to allow for diagnostics or other manipulation of an all-inclusive device.

In some embodiments, the sample for use in the methods is obtained from cells of solid tumor (e.g. breast cancer cell lines). In some embodiments, the cell lines include BT-474, SK-BR3, MDA-MB-453 and UACC-893. In some embodiments, the cell lines include Mino and DoHH2 cell lines.

In some embodiments, the sample is any tissue or fluid samples from a patient. Samples include, but are not limited to, blood, lymph, urine, gynecological fluids, biopsies, and smears. Bodily fluids useful for the methods disclosed herein include blood, urine, saliva, nipple aspirates, or any other bodily secretion or derivative thereof. In some embodiments, blood includes whole blood, plasma, serum, or any derivative of blood. In some embodiments, the body sample comprises breast cells, for example breast tissue from a biopsy, or a breast tumor tissue sample.

In some embodiments, body samples are obtained from a patient by a variety of techniques including, for example, by scraping or swabbing an area, by using a needle to aspirate bodily fluids, or by removing a tissue sample (i.e., biopsy). Methods for collecting various body samples are well known in the art. In some embodiments, a breast tissue sample is obtained by, for example, fine needle aspiration biopsy, core needle biopsy, or excisional biopsy. Fixative and staining solutions may be applied to the cells or tissues for preserving the specimen and for facilitating examination. Body samples, particularly breast tissue samples, may be transferred to a glass slide for viewing under magnification.

Kits/Articles of Manufacture

Described herein are kits for treating HER2 amplified breast cancer in an individual in need thereof comprising administering to the individual a composition comprising a therapeutically-effective amount of an ACK inhibitor compound (e.g., a BTK inhibitor, such as for example ibrutinib). Further described herein are kits for treating HER2 amplified cancer in an individual in need thereof comprising administering to the individual a composition comprising a therapeutically-effective amount of an ACK inhibitor compound (e.g., a BTK inhibitor, such as for example ibrutinib).

For use in the therapeutic applications described herein, kits and articles of manufacture are also described herein. In some embodiments, such kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder that benefit by inhibition of Btk, or in which Btk is a mediator or contributor to the symptoms or cause.

The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

In some embodiments, a label is on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, a pharmaceutical composition comprising the ACK inhibitor compound (e.g., a BTK inhibitor, such as for example ibrutinib) is presented in a pack or dispenser device which can contain one or more unit dosage forms. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following specific and non-limiting examples are to be construed as merely illustrative, and do not limit the present disclosure in any way whatsoever.

Example 1

Assays and Reagents
Cells and Reagents:
Breast cancer lines (BT-474, SK-BR3, MDA-MB-453 and UACC-893) were obtained from ATCC and cultured as indicated from the source. Antibodies were obtained from Cell Signaling and Santa Cruz Biotechnologies. Western blotting reagents were obtained from Life Technology (Invitrogen). Antibody to Btk was obtained from BD Biosciences.

BT-474 and SK-BR-3 cells (ATCC) were cultured in DMEM and McCoy 5A media, respectively, supplemented with 10% fetal calf serum. Antibodies to EGFR, pEGFR (Y1086), HER2, pHER2 (Y1248), HER3, pHER3 (Y1289), Akt, pAkt, MEK, pMEK, and pBtk (Y223) were from Cell Signaling Technology. Antibodies to HER4, pHER4 (Y1056), ERK, pERK, and α-tubulin were from Santa Cruz Biotechnology, Inc. Antibody to BTK was from BD Biosciences.

Kinase Activity Assay:
The LabChip platform was used for enzyme activity assay performed by Nanosyn, Inc. The recombinant enzymes were used at 5 nM with substrate at 1 µM.

Cell Proliferation Assay with Alamar Blue:
Cells were plated at 10,000 cells/well in 100 µL. After 3 days incubation at 37° C. in a 5% $CO_2$ incubator, alamar blue (Invitrogen 1:10) was added into each well and incubated for another 2.5-3 hours. The plate was read at Excitation/Emission wavelengths of 545/590 nm.

Cell Growth Inhibition Wash Out Assay:
Cells were plated at 350,000 cells/plate for BT-474, and 300,000 cells/plate for SK-BR-3 cells in 10 cm plate. Cells were treated with ibrutinib for 1 h. After wash-out and fresh media added, the culture continued for another 6 days. Cell number in each plate was counted by cell counter after trypsinization.

Cell Cycle Analysis:
Cells were plated at 350,000 cells/plate for BT-474, and 300,000 cells/plate for SK-BR-3 cells in 10 cm plate. Cells were treated with ibrutinib for 1 h. After washing twice with media, the culture was continued for 24 h. Cells were fixed in 70% ethanol, and stained with PI/RNase. The data were acquired with BD FACSCalibur, and the cell cycle analysis was performed using FlowJo software.

Immunoblotting:
Cells were washed once with cold PBS and lysed in 1× sample buffer (Invitrogen). The whole cell lysate was boiled, sonicated, and then loaded onto a 4-15% gradient SDS-PAGE gel. The proteins were transferred to PVDF membrane. After probing with antibodies, the detection was conducted using an Odyssey spectrometer (Li-Cor). Paired mouse and rabbit antibodies were used to probe the total and corresponding phosphorylated proteins.

Tumorsphere Culture:
BT-474 cells were treated with ibrutinib for 1 h at 120,000 cells in 1 mL media, in triplicate. The culture was conducted in a 6-well ultra-low adherent plate using MammoCult media as suggested by manufacturer (Stem Cell Technologies). For treatment, cells were trypsinized and the single cell suspension were treated with ibrutinib for 1 h in triplicate. After washing twice, the cells were resuspended in 6 mL complete MammoCult media, and cultured for 7 days. For tumorsphere counting, concentrate the spheres into 1.5 mL media, and transfer into a 96-well plate. The number of tumorspheres was counted using a Nikon phase-contrast microscope for the spheres larger than 5 mm, using a ruler installed in the eyepiece. The size of tumorspheres was measured from photos taken in the microscope with 4× objective. 5 pictures were taken for each well, and the size of tumorspheres in computer monitor was measured.

Aldefluor Assay:
BT-474 cells were treated with ibrutinib for 1 h, washed twice, and the culture continued for 3 days, or were cultured continuously in the presence of 0.1 µM ibrutinib for 3 days. The assay was conducted according to directions provided by the manufacturer (Stem CellTechnologies). Cells were incubated with the Aldefluor reagent for 35 minutes prior to flow cytometry.

Western Blotting:
Whole cell lysates in 1× sample buffer (Invitrogen) were electrophoresed on a 4%-12% Bis-Tris gel. After transferring the proteins onto a PVDF membrane, the blot was probed by antibodies, and signal was detected using an Odyssey imager (LI-COR Biosciences). Paired mouse and rabbit antibodies were used to probe the total and corresponding phosphorylated proteins.

Apoptosis Assay:
Cells were stained with annexin-V/PI or PI/RNase, and apoptotic cells were quantitated using a FACSCalibur flow cytometer (Becton Dickinson). The numbers of annexin-V positive cells or subG0 cells were calculated.

Results
Inhibition of ErbB Kinases by Ibrutinib
ErbB family of kinases share high degrees of homology in their kinase domain with Btk around a conserved cysteine residue, which can bond irreversibly to ibrutinib (FIG. 1). The ability of ibrutinib to inhibit the various kinases illustrated in FIG. 1 was assayed. As shown in the figure, ibrutinib was able to inhibit EGFR (ErbB1), ErB2 and Erb4 in addition to BTK and other members of the TEC kinase family (e.g. BMX, TEC, TXK, ITK, JAK3 and BLK). In a separate experiment, it was further observed that kinase inhibition was dialysis resistant (data not shown), which supports covalent inhibition.

Figure 3A:
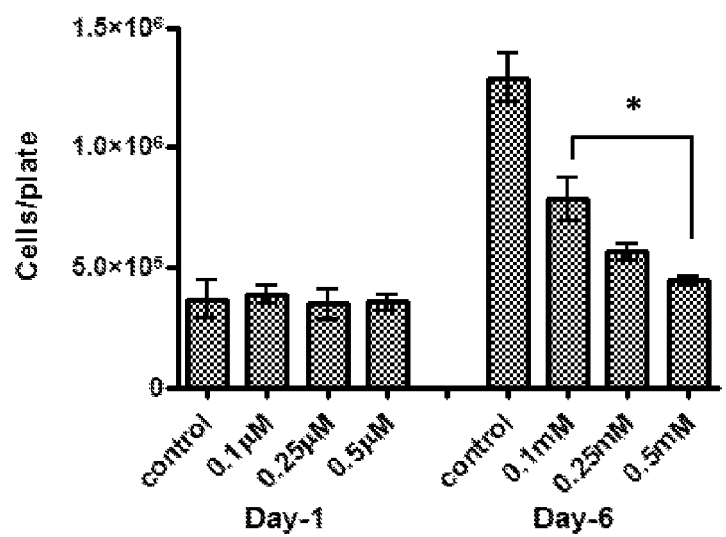
Figure 4A:
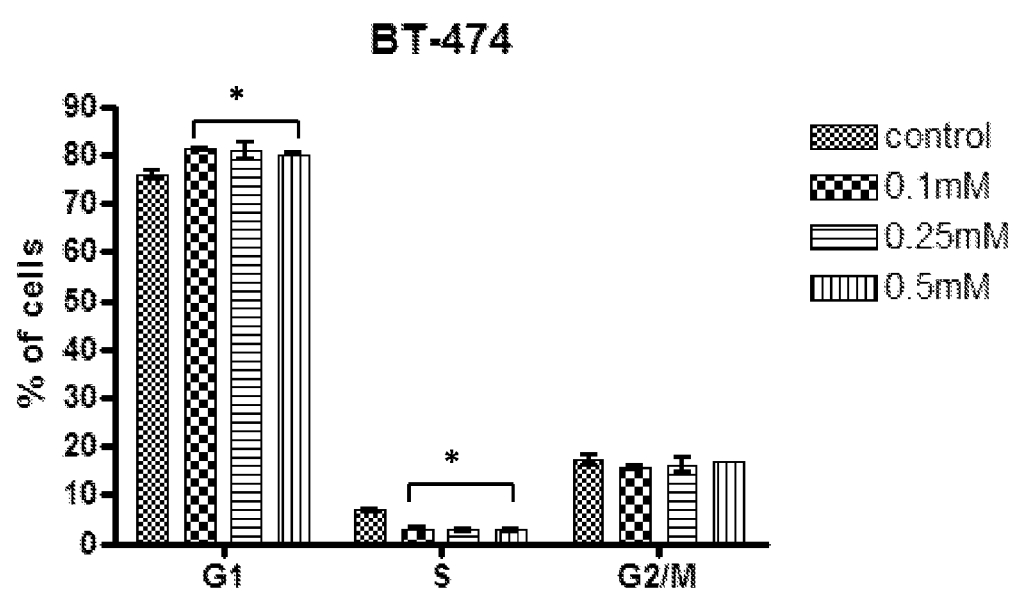
FIG. 4A-FIG. 4B: exemplify cells with 1 h exposure to ibrutinib had G1 arrest as measured at 24 h for both (A) BT-474 cells and (B) SK-BR3 cells.
Figure 4B:
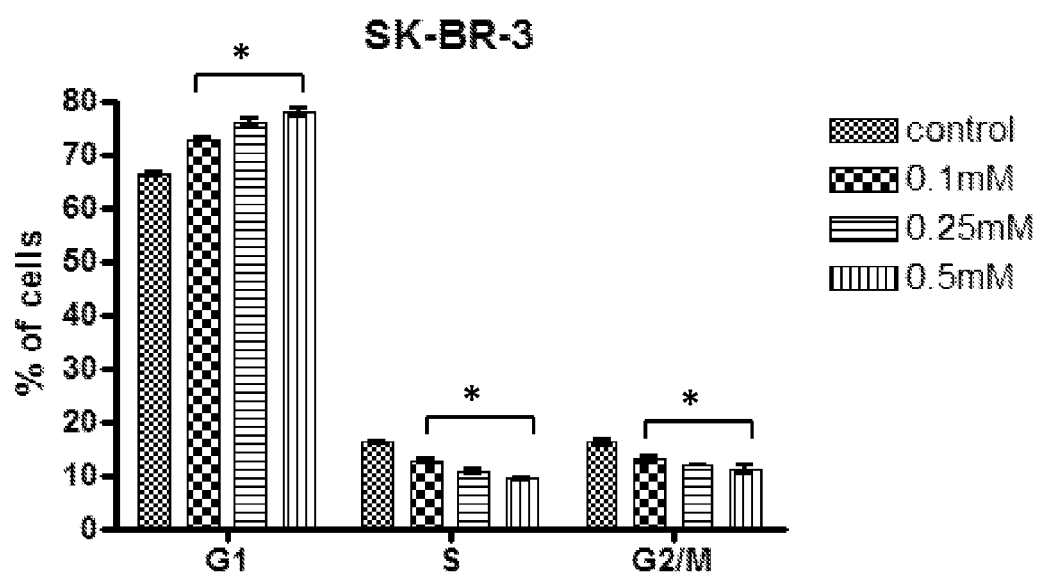
Figure 33:
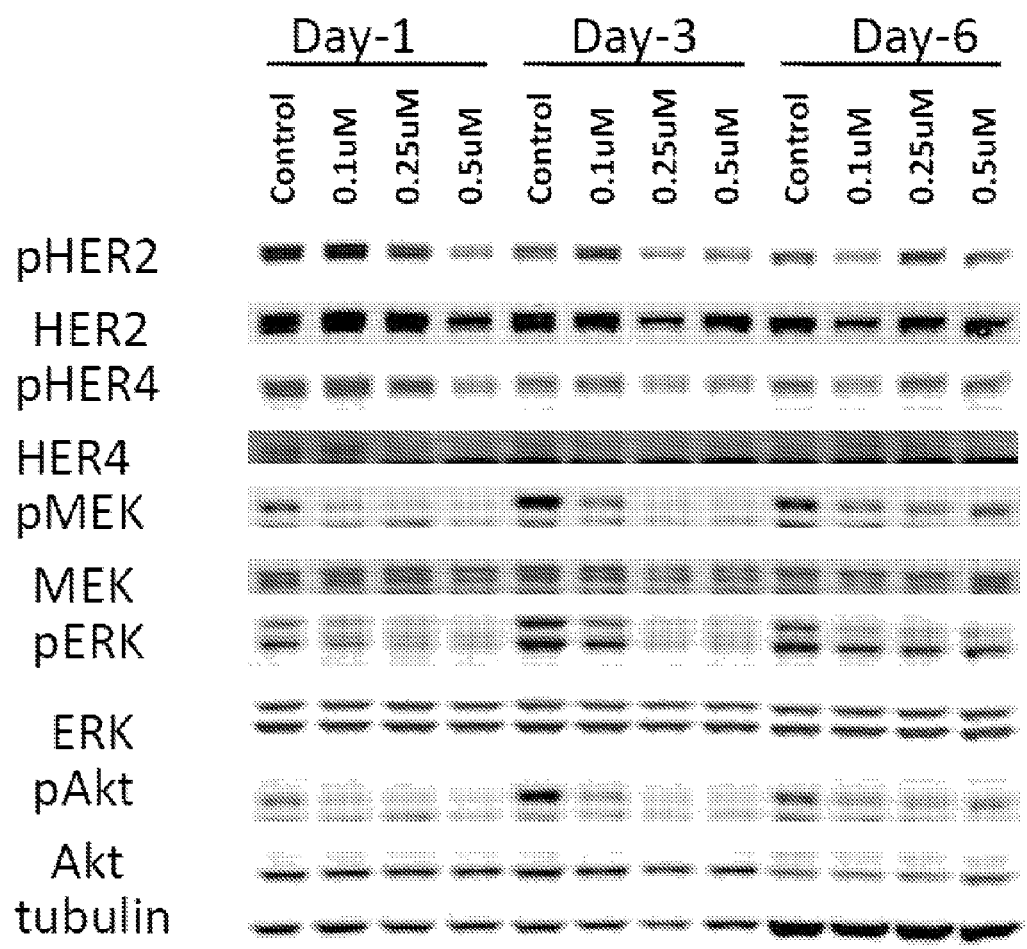
FIG. 33: exemplifies one hour treatment of ibrutinib followed by washout on signaling pathways. Ibrutinib has a long-lasting inhibitory effect even after day 6 on HER signaling pathway.

Growth Inhibition of HER-2 Positive Breast Cancer Cells
Breast cancer lines (BT-474, SK-BR3, MDA-MB-453 and UACC-893) which are HER2 amplified were cultured in the presence of ibrutinib, AVL-292 and PCI-45468. After 3 days continuous exposure to ibrutinib, it was observed that the HER-2 positive breast cancer cells are sensitive to the growth inhibitory effect of ibrutinib as assay by alamar blue assay (see e.g., FIGS. 2A-2D). After 1 hour exposure to ibrutinib followed by wash out and culturing for 6 days, it was observed that the growth inhibitory effect was sustained and was dose dependent (see, e.g., FIGS. 3A and 3B). Further, one hour treatment with ibrutinib has a lasting inhibitory effect even after day 6 on HER signaling pathway (see, e.g. FIG. 33). Cell cycle analysis showed that cells with 1 h exposure to ibrutinib had G1 arrest as measured at 24 h (see, e.g., FIGS. 4A and 4B). For BT-474 cells, the difference was statistically significant ($p<0.05$) between the control and ibrutinib treated groups. For SK-BR-3 cells, the difference was statistically significant (p<0.05 or p<0.01) between the control and ibrutinib treated groups, and among different dose groups.

Figure 5A:
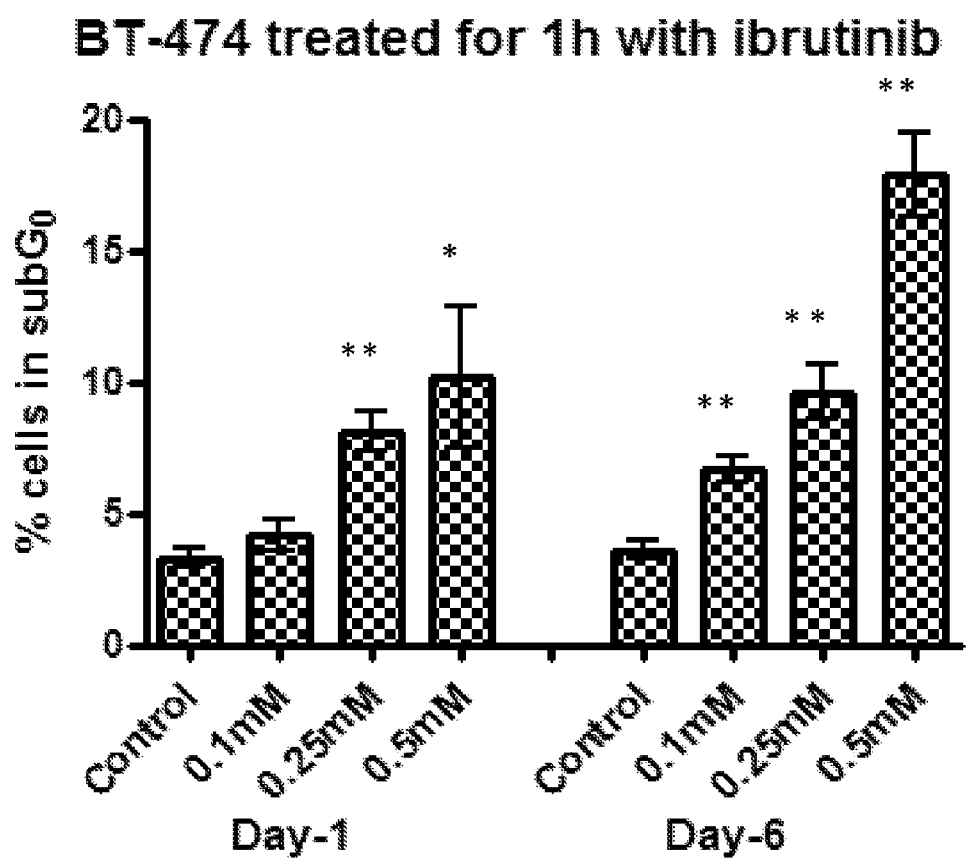
FIG. 5A-FIG. 5C: exemplify the effects of ibrutinib and PCI-24781 on BT-474 cell apoptosis. (A) One hour of ibrutinib treatment (Day 1) followed by followed by wash out and six days culture (Day 6). Apoptosis was measured as percentage of cells in sub G0. (B, C) three days continuous ibrutinib and PCI-24781 incubation with or without the caspase inhibitor Q-VD-OPH. Apoptosis was measured as percentage of cells (B) with annexin-V positivity or (C) in sub G0. *p<0.05; **: p<0.01.
Figure 5B:
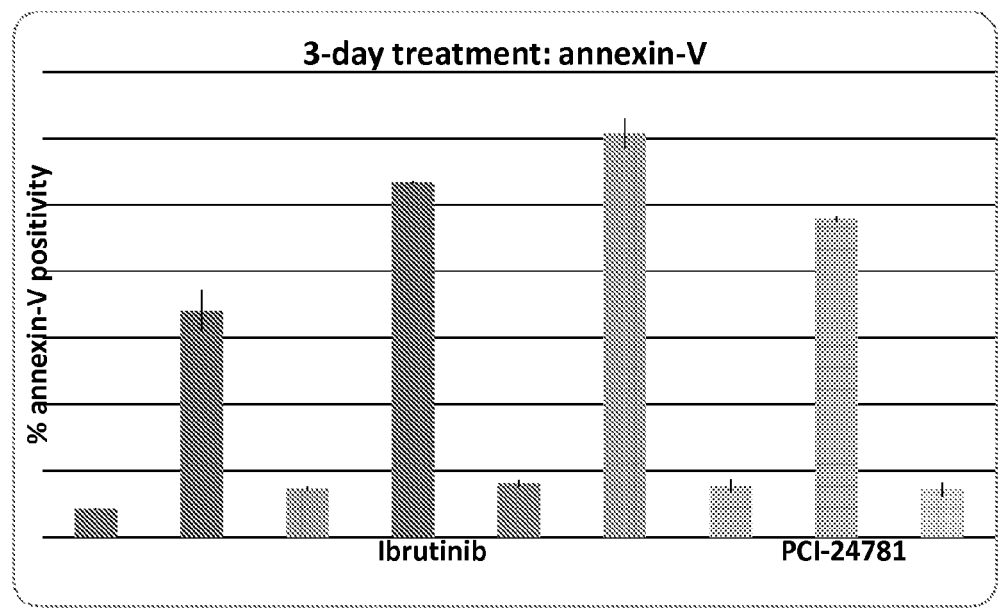
Figure 5C:
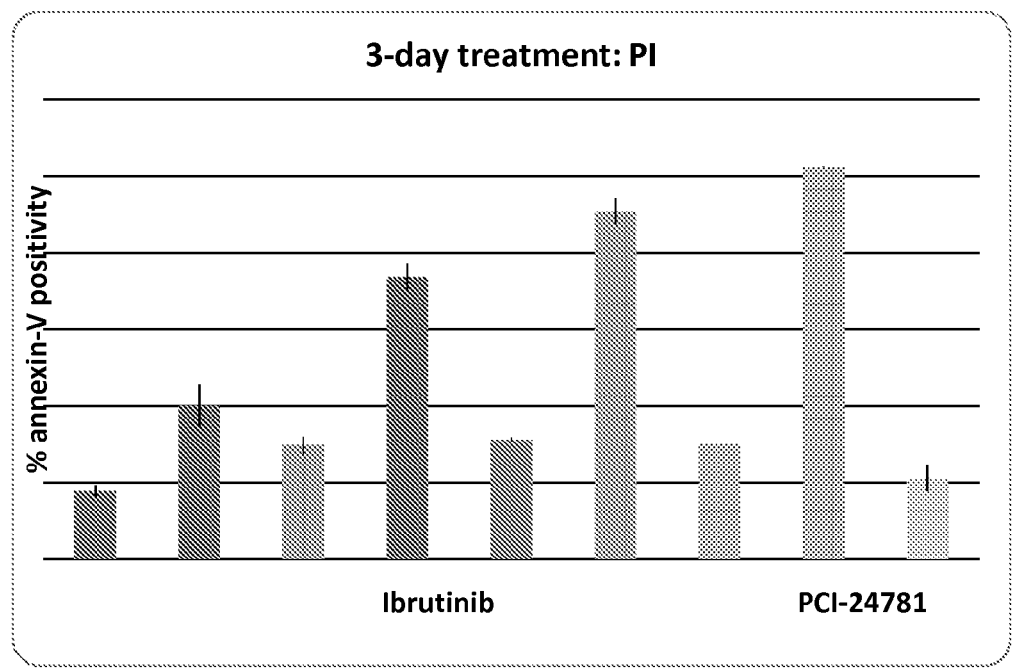
Figure 6A:
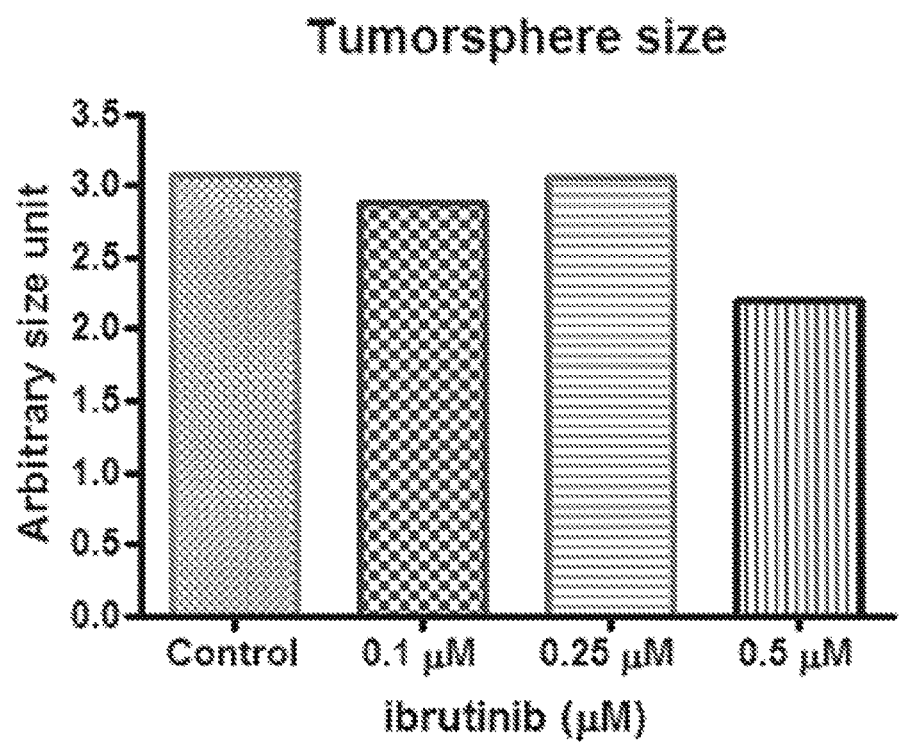
Figure 6B:
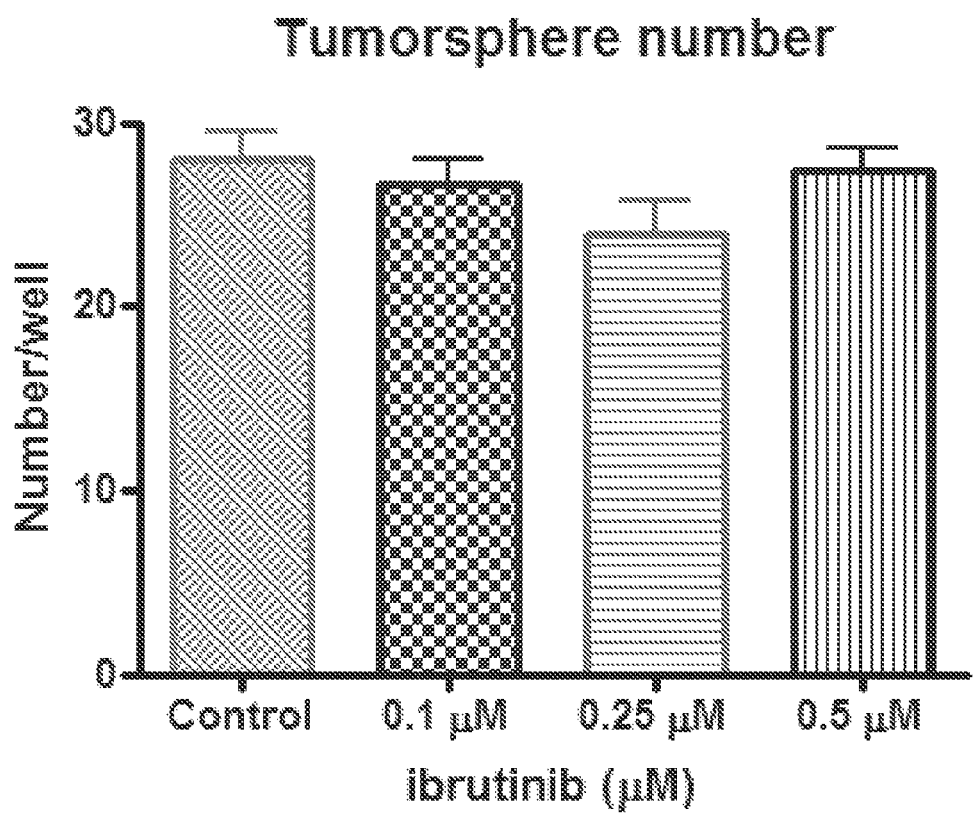
Figure 7:
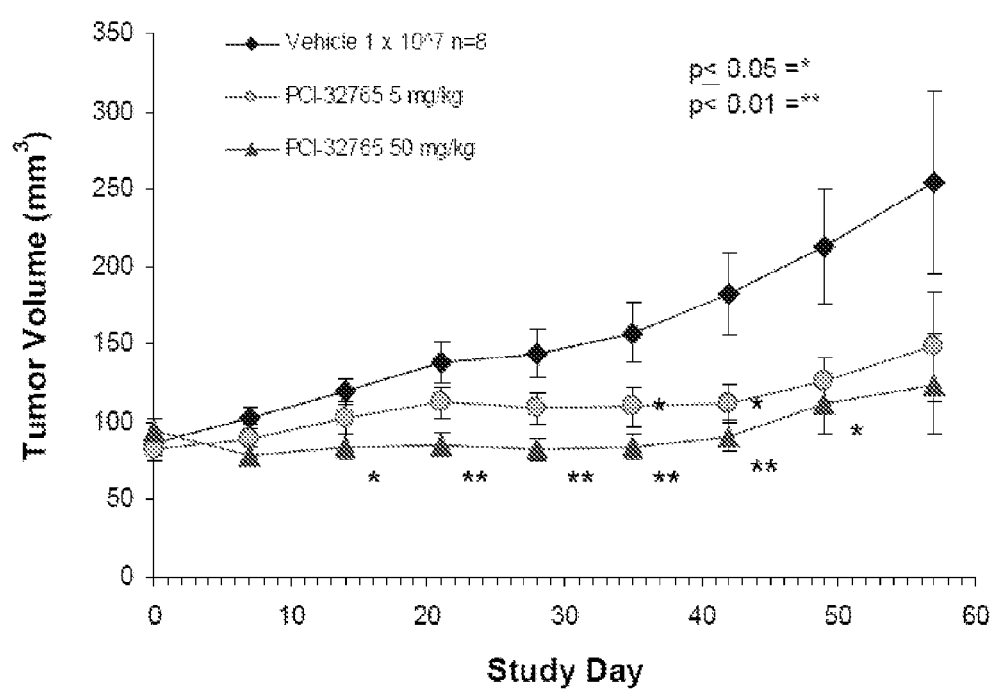
FIG. 7: exemplifies the effects of ibrutinib on tumor volume of a MDA-MB-453 mouse xenograft.
Figure 17:
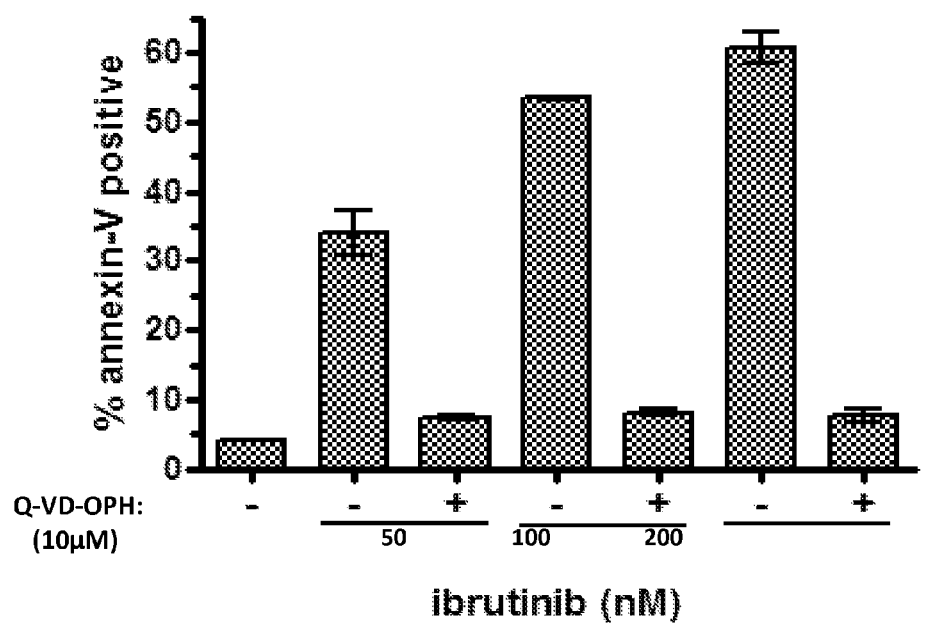
FIG. 17: exemplifies the effect of ibrutinib on BT-474 cell apoptosis. Ibrutinib was incubated for three days continuously with or without the caspase inhibitor Q-VD-OPH.

Ibrutinib induced apoptosis in BT-474 cells (see, e.g., FIGS. 5A-C and FIG. 17). One hour of drug treatment caused a low level of apoptosis 6 days after the exposure (FIG. 5A), while continuous treatment (3-day) resulted in dramatic apoptosis which was caspase-dependent Q-VD-OPH (FIGS. 5B and 5C, and FIG. 17). Apoptosis was measured as percentage of cells in sub G0 or with annexin-V positivity. Ibrutinib also inhibited tumorsphere growth of BT-474 cells in culture without affecting tumorsphere number (see, e.g. FIG. 6A-B) and inhibited solid tumor growth in a mouse MDA-MB-453 xenograft (see e.g. FIG. 7).

Figure 8:
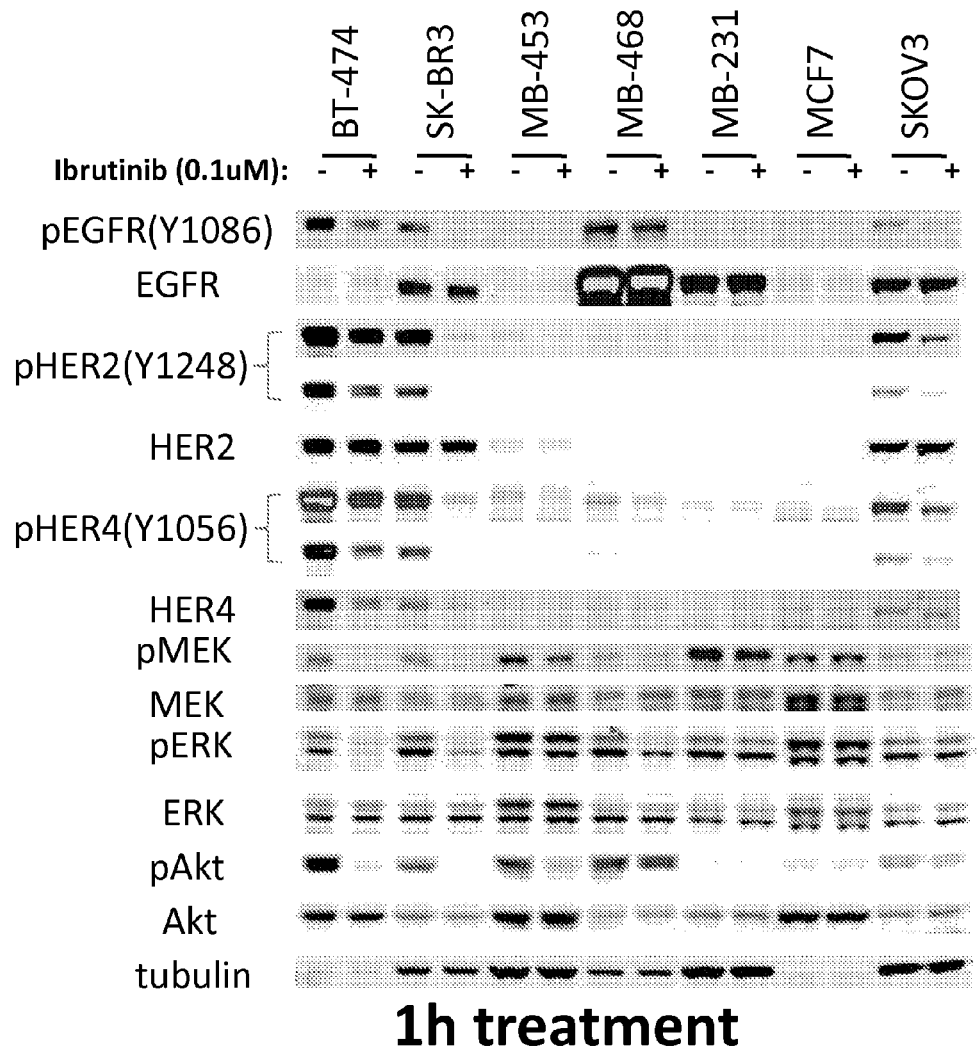
FIG. 8: exemplifies gene expression levels of various biomarkers in multiple cancer cell lines with (+) or without (−) addition of 0.1 µM ibrutinib (1 hour treatment).
Figure 9:
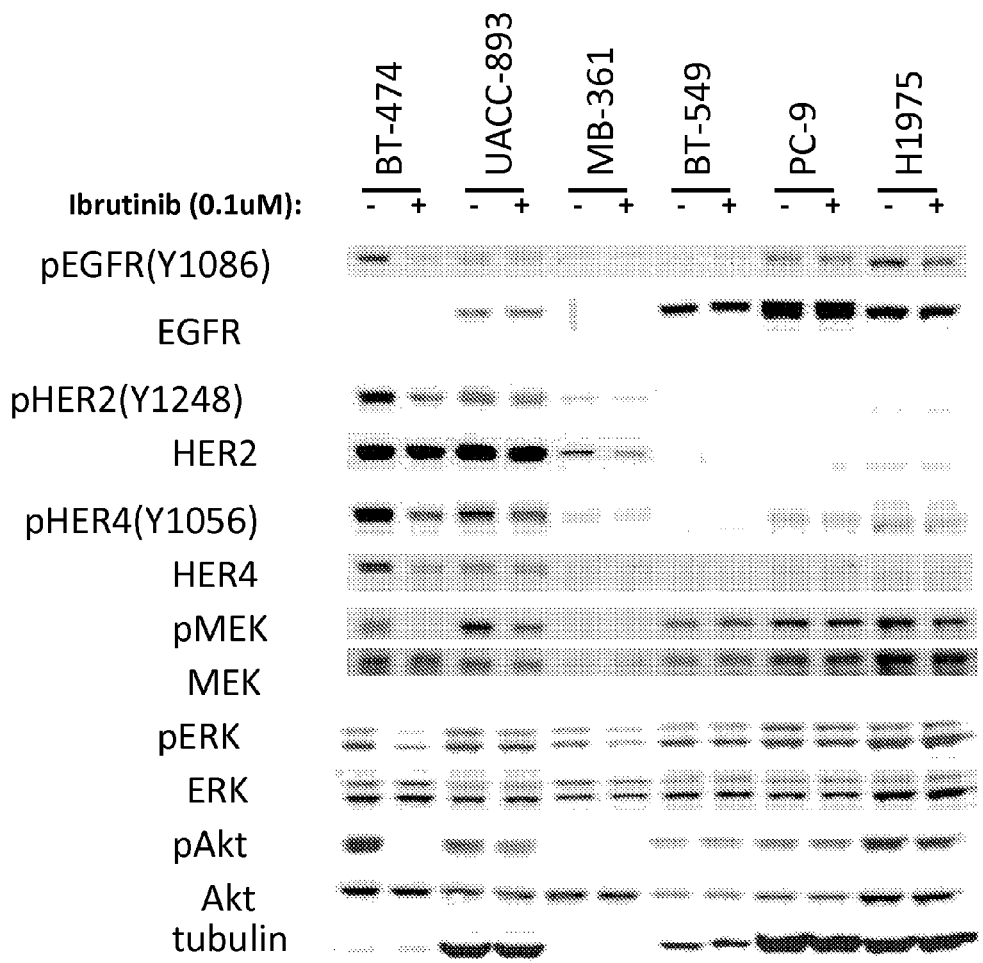
FIG. 9: exemplifies gene expression levels of various biomarkers in multiple cancer cell lines with (+) or without (−) addition of 0.1 µM ibrutinib (1 hour treatment).
Figure 10:
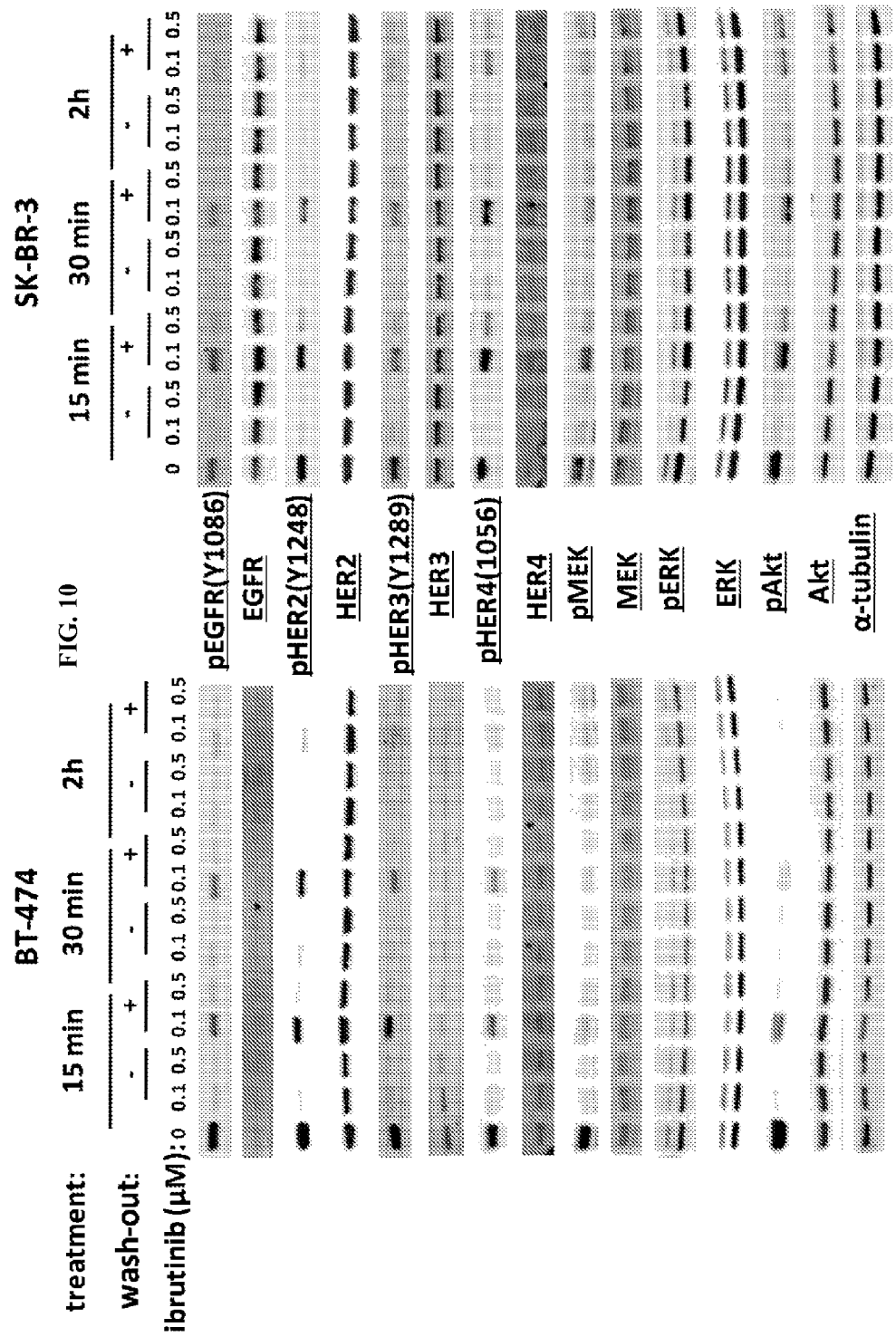
FIG. 10: exemplifies gene expression levels of various biomarkers in BT474 (left panel) and SKBR-3 (right panel) breast cancer cell lines with (+) or without (−) addition of 0.1 µM or 0.5 µM of ibrutinib, at 15, 30 or 2 hour treatment, and with (+) or without (−) washout.

The expression of total and phosphorylated forms of EGFR, HER2, HER4, MEK, ERK, and AKT was examined in various cancer cells lines in the absence or presence of ibrutinib (0.1 µM) after 1 hour of treatment. Breast cancer lines that were sensitive to ibrutinib are also HER2/4-amplified (see, e.g., FIGS. 8 and 9). In a washout experiment, where cells were treated with ibrutinib for various times and then cultured for an additional 2 hours, inhibition of ErbB kinases and down-stream signaling pathways persisted after ibrutinib washout, and was time and concentration dependent (see, e.g., FIG. 10).

Figure 11:
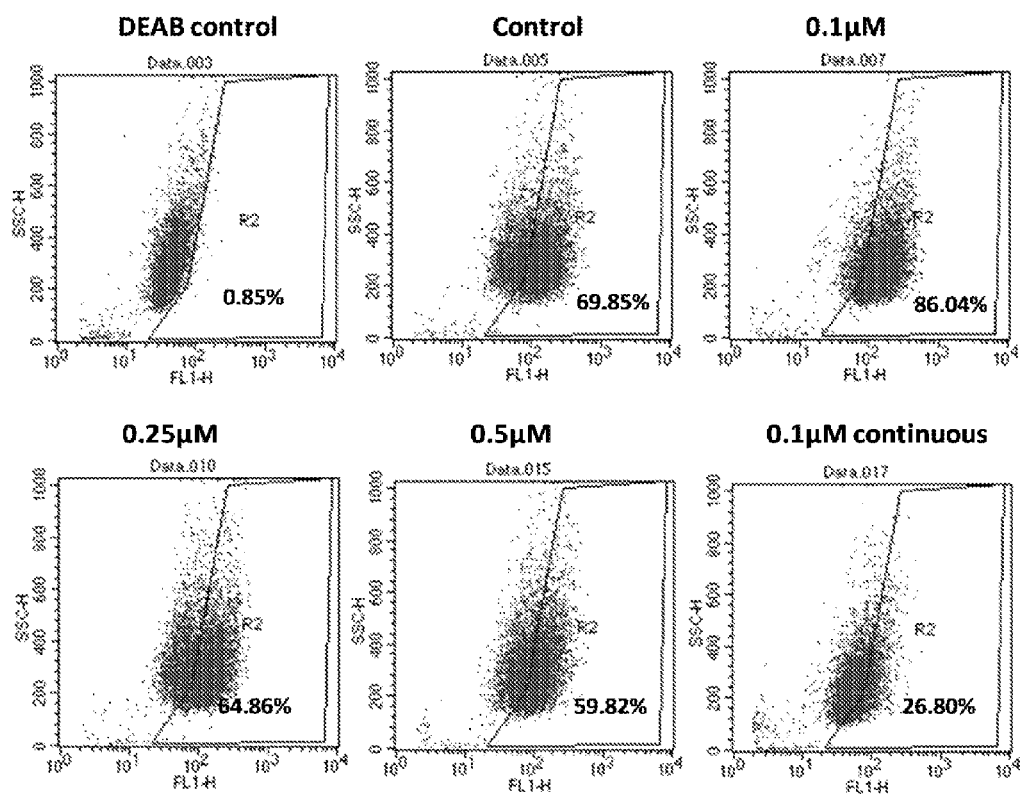
FIG. 11: exemplifies the effects of ibrutinib on expression of the progenitor cell marker aldehyde dehydrogenase (ALDH) by Aldefluor assay. BT-474 breast cancer cells were treated with 0, 0.1 µM, 0.25 µM 0.5 µM ibrutinib for 1 h followed by washout and three days continued culture or 0.1 µM ibrutinib continuously for three days.
Figure 18A:
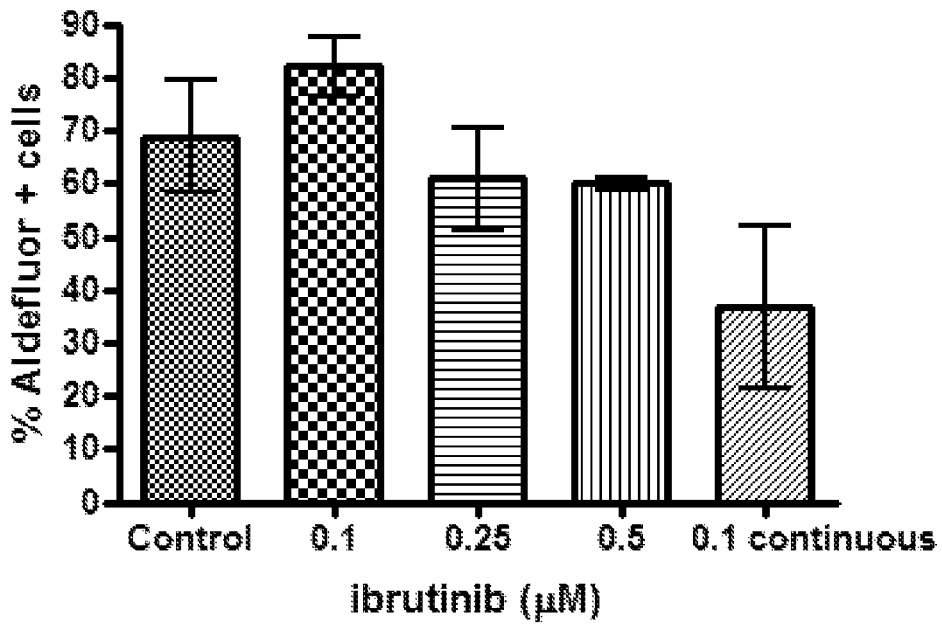
FIG. 18A and FIG. 18B: exemplify the effects of ibrutinib on expression of the progenitor cell marker aldehyde dehydrogenase (ALDH) by Aldefluor assay (A) and propidium iodide (PI) assay (B) *: p=0.06.
Figure 18B:
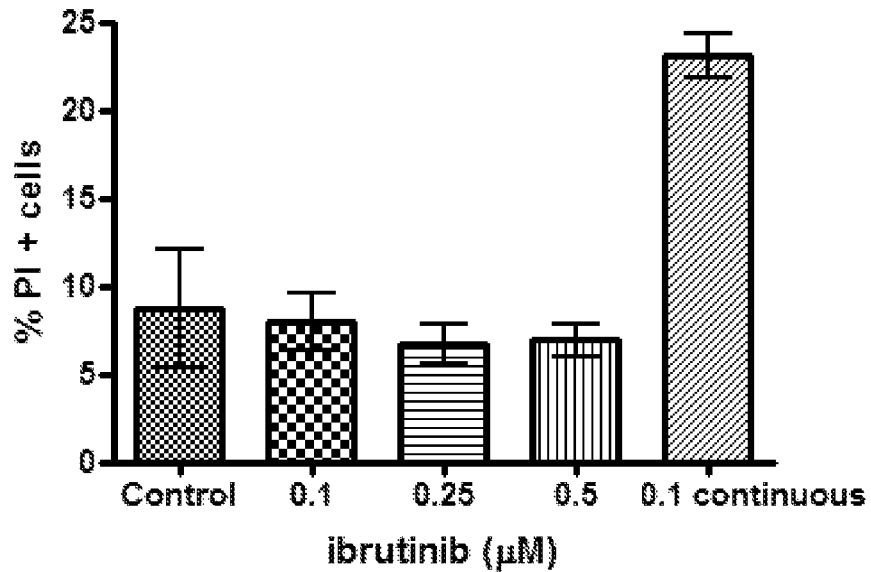

The effect of ibrutinib on progenitor cell marker expression in BT-474 breast cancer cells was analyzed by Aldefluor assay, which identifies progenitor cells based on expression of aldehyde dehydrogenase (ALDH). Diethylaminobenzaldehyde (DEAB) inhibits aldehyde dehydrogenase activity and was used as a control in the assay. It was observed that one hour or continuous treatment with ibrutinib decreased putative "stem-like" subpopulation of breast cancer cells (see, e.g., FIG. 11 and FIG. 18). For example, decreased aldehyde dehydrogenase activity detected by the Aldefluor assay was noted after short exposures to high concentrations or continuous exposure to low concentration of ibrutinib. Thus, short exposure to ibrutinib causes a reduction of growth potential for putative "stem-like" cancer cells.

Figure 12:
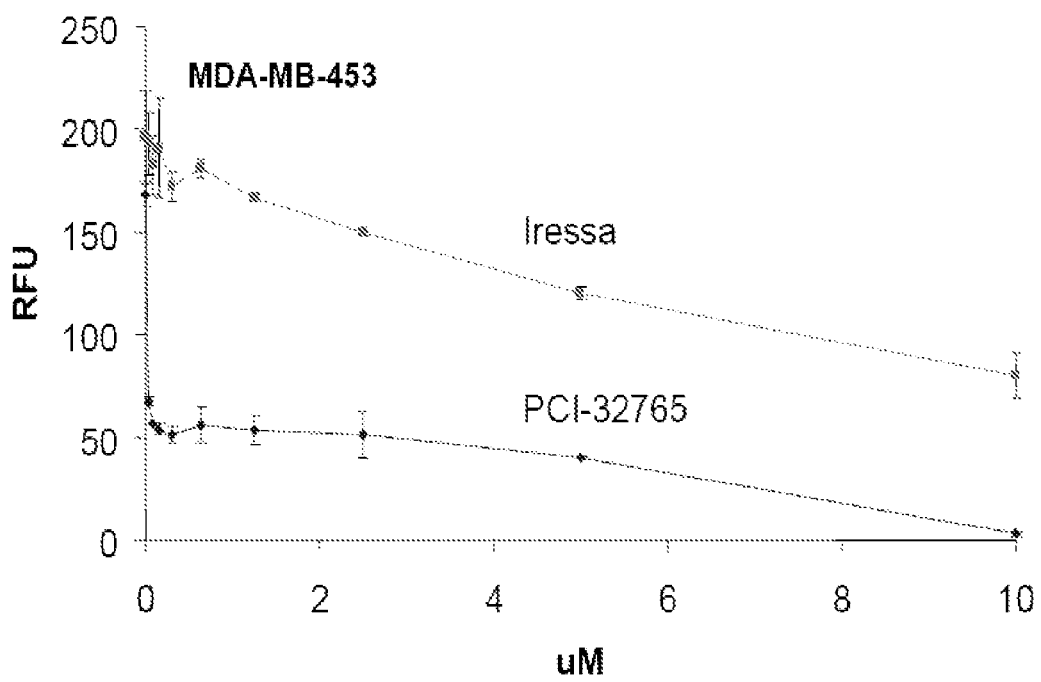
FIG. 12: is an exemplary dose response comparison of the effects of increasing concentrations of gefitinib (Iressa) and ibrutinib on MDA-MB-453 cells.
Figure 13A:
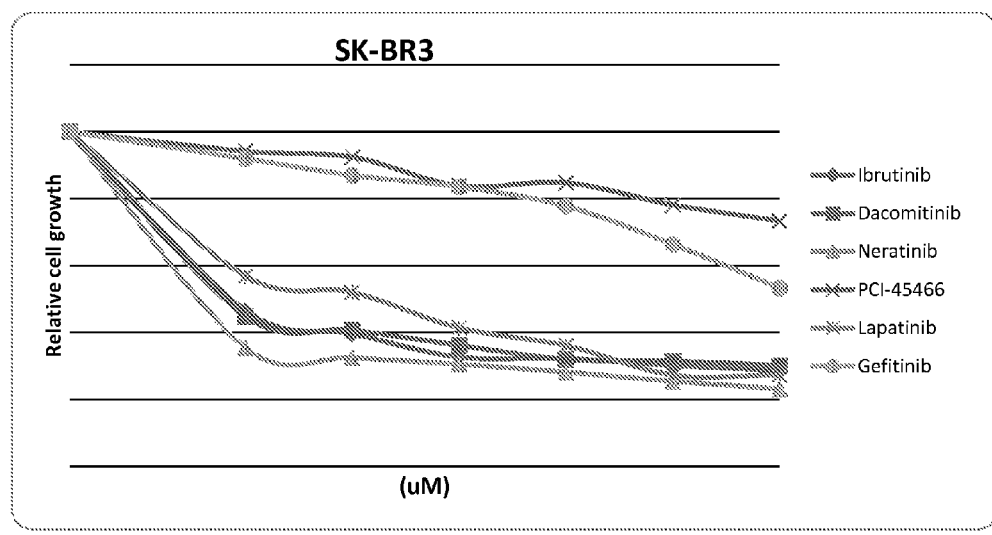
FIG. 13A-FIG. 13B: exemplify the dose response effects of ibrutinib, dacomitinib, neratinib, PCI-45466, lapatinib, and gefitinib on relative cell growth of (A) SK-BR3 cells and (B) MDA-MB-453 cells.
Figure 13B:
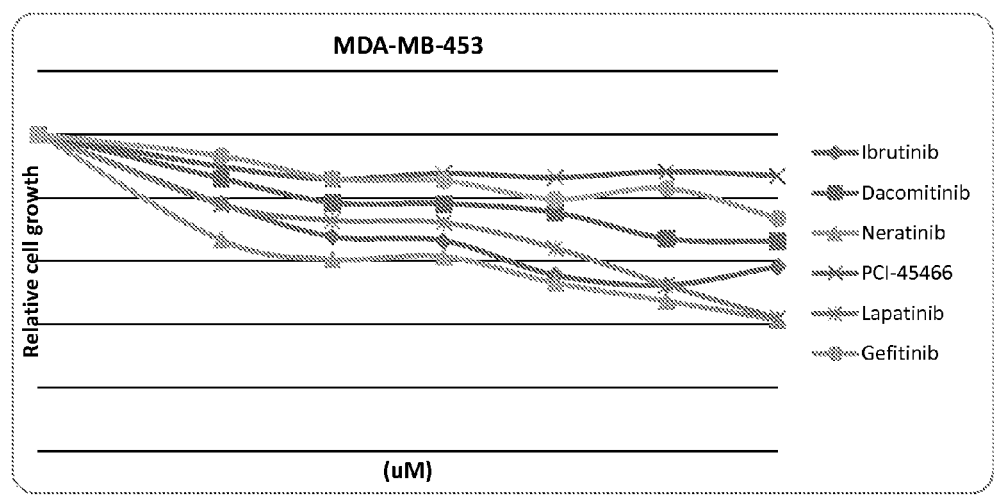
Figure 14A:
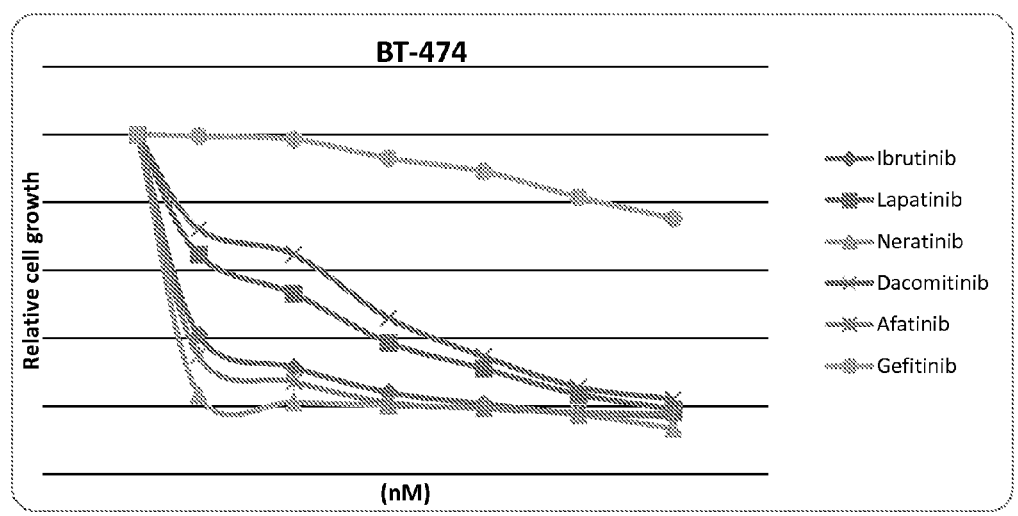
FIG. 14A-FIG. 14C: exemplify the dose response effects of ibrutinib, lapatinib, neratinib, dacomitinib, afatinib, and gefitinib on relative cell growth of (A) BT-474 cells, (B) SK-BR3 cells and (C) MDA-MB-453 cells.
Figure 14B:
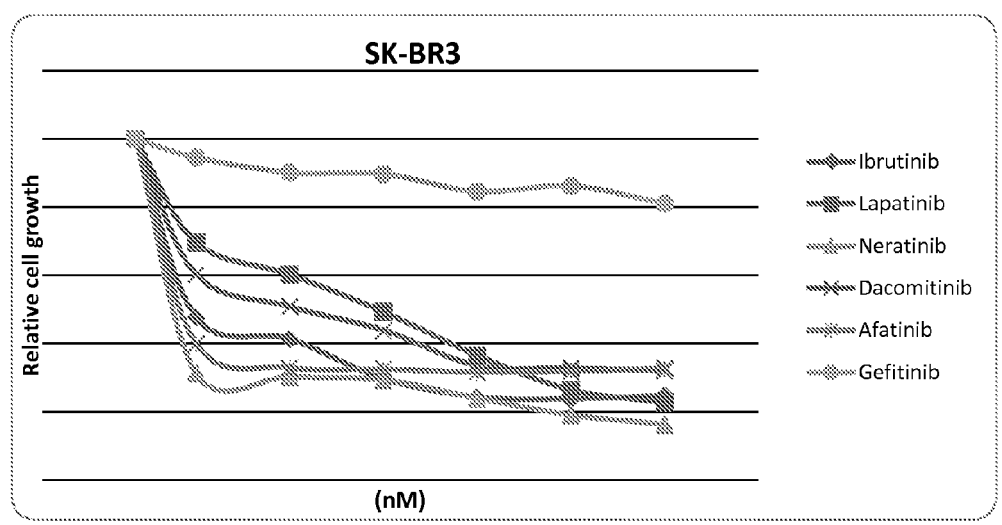
Figure 14C:
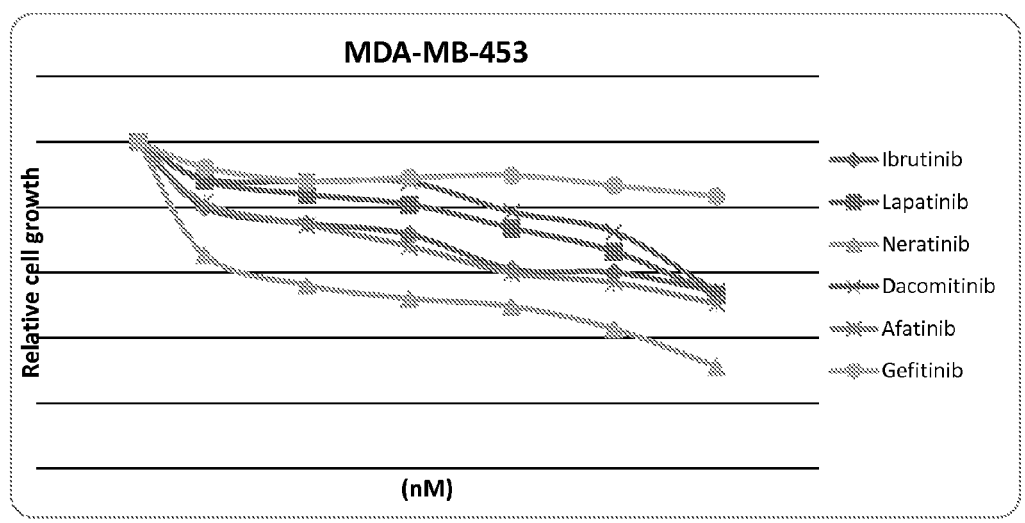
Figure 15A:
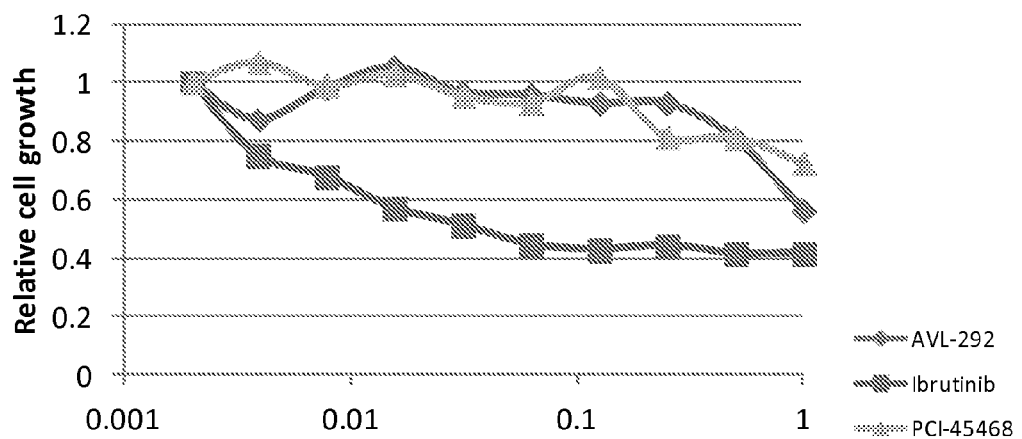
FIG. 15A-FIG. 15C: exemplify the dose response effects of ibrutinib, AVL-292 and PCI-45468 on relative cell growth of (A) SK-BR3 cells, (B) MDA-MB-453 and (C) BT-474 cells.
Figure 15B:
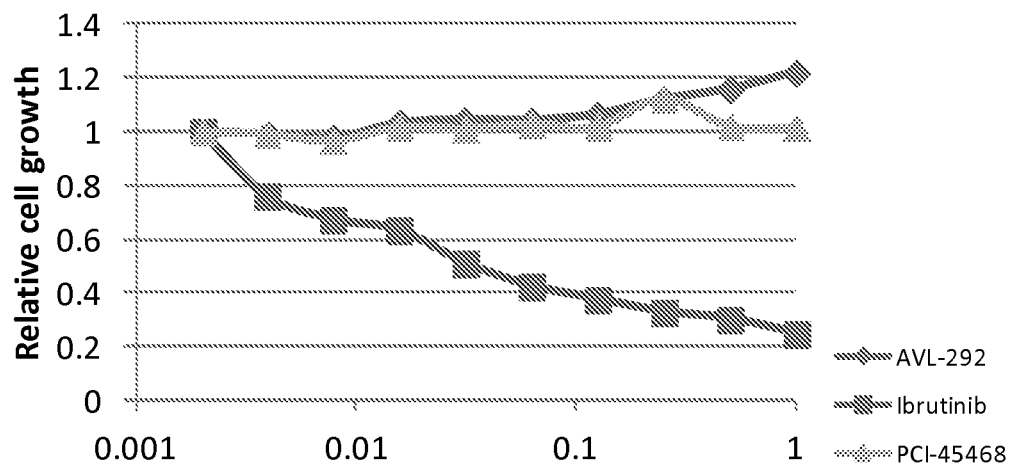
Figure 15C:
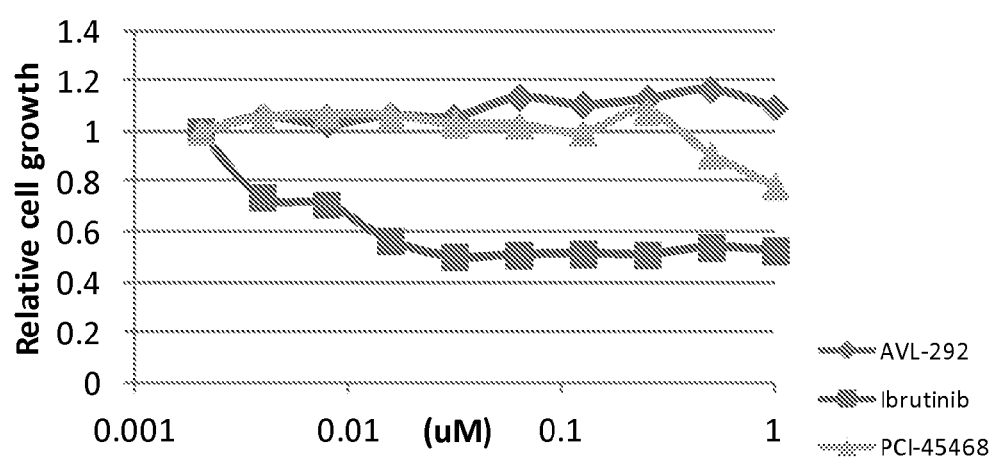
Figure 16:
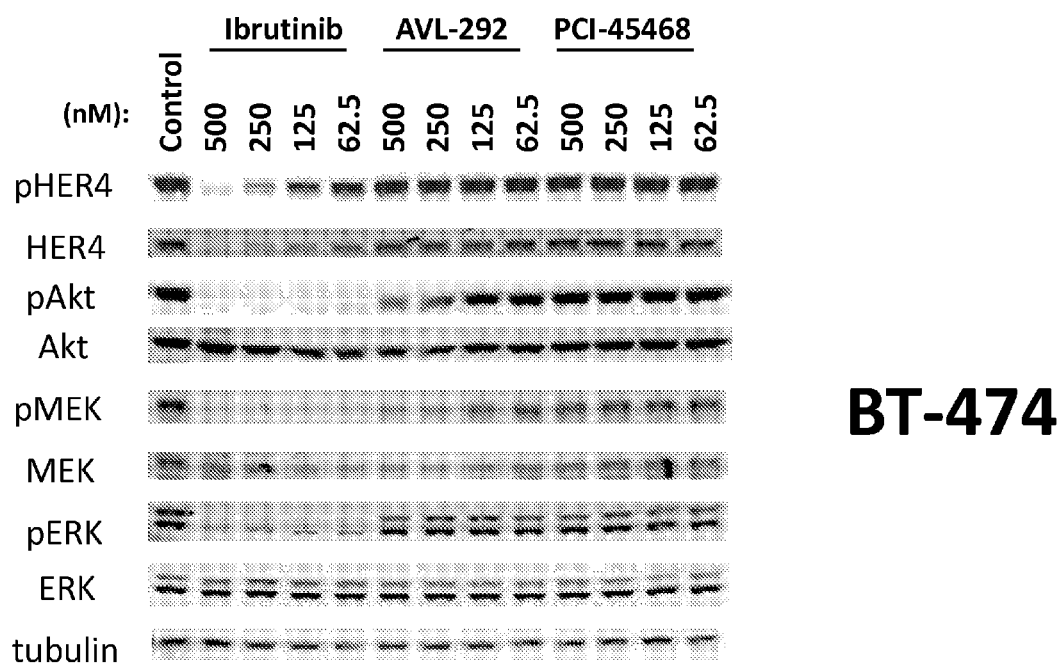
FIG. 16: exemplifies the effects of ibrutinib, AVL-292 and PCI-45468 on HER2 and HER activation and downstream pathways in BT-474 cells.

Using a fluorescence-based assay, the inhibition of the breast cancer cell line MDA-MB-453 by ibrutinib or gefitinib (Iressa) was determined. Gefitinib is a reversible inhibitor that has higher EGFR inhibitory activity but lower HER2/4 inhibitory activity compared to ibrutinib. It was observed that ibrutinib was more potent than gefitinib in inhibiting MDA-MB-453 cell growth (see e.g., FIG. 12). Ibrutinib also exhibited similar growth inhibitory activity in SK-BR3 cells and MDA-MB-453 breast cancer cells and as compared to lapatinib, neratinib and dacomitinib (see, e.g., FIGS. 13A and 13B). Separate experiments confirmed ibrutinib inhibitory activity in BT-474, SK-BR3 and MDA-MB-453 breast cancer cells as compared to kinase inhibitors gefitinib, lapatinib, neratinib and dacomitinib (see, e.g., FIGS. 14A-C). Ibrutinib was also a more potent inhibitor of cell growth compared to AVL-292 in BT-474, SK-BR3 and MDA-MB-453 breast cancer cells (see, e.g., FIGS. 15A-C). In addition, as compared to AVL-292, only ibrutinib inhibited HER2 and HER4 activation as assessed by phosphorylation of downstream targets, such as AKT (see, e.g., FIG. 16).

Example 2—HER2 Amplified Breast Cancer

Study Type: Interventional
Study Design:
Allocation: Non-Randomized
Endpoint Classification: Safety/Efficacy Study
Intervention Model: Single Group Assignment
Masking: Open Label
Primary Purpose: Treatment
Outcome Measures
To estimate the efficacy [overall response rate (ORR)= complete response (CR) and partial response (PR)](phase II)
To determine the expression level of HER2 and p95-HER2 in the metastatic tissue samples and correlate this with response to the ibrutinib in HER2-amplified tumors. [Time Frame: once at the time of biopsy] [Designated as safety issue: No]
Eligibility
Ages Eligible for Study: 18 Years and older
Genders Eligible for Study: Both
Accepts Healthy Volunteers: No
Inclusion Criteria:
Phase I HER2-Amplified Cohort
HER2 overexpression and/or amplification as determined by immunohistochemistry (3+) or FISH (≥2.0)
Previously received trastuzumab as part of a regimen in the adjuvant or metastatic setting with evidence of progression. Washout period for trastuzumab of 14 days.
May have previously received lapatinib as part of a regimen in the adjuvant or metastatic setting with evidence of progression of disease. Washout period for lapatinib of 14 days.
Radiographic progression of disease while on treatment with trastuzumab or lapatinib as defined by RECIST 1.1 criteria.
No restriction on prior chemotherapy regimens for advanced stage disease. No restriction for prior hormonal therapy. No concurrent use of endocrine therapy is permitted.
Phase II HER2-Amplified Cohort
HER2 overexpression and/or amplification as determined by immunohistochemistry (3+) or FISH (≥2.0).
Previously received trastuzumab as part of a regimen in the adjuvant or metastatic setting with evidence of progression. Washout period for trastuzumab of 14 days.
May have previously received lapatinib as part of a regimen in the adjuvant or metastatic setting with evidence of progression of disease. Washout period for lapatinib of 14 days.
Radiographic progression of disease while on treatment with trastuzumab as defined by RECIST 1.1 criteria.
Prior Therapy Inclusion:
No more than four prior chemotherapy regimens allowed for advanced stage disease. No restriction for prior hormonal therapy. No concurrent use of endocrine therapy is permitted.
Inclusion Criteria for all Subjects
Patients with a diagnosis of invasive adenocarcinoma of the breast confirmed by histology or cytology at MSKCC.
Metastatic disease that is or has been pathologically documented.
At least one measurable metastatic lesion according to RECIST 1.1 criteria. Ascites, pleural effusions, and bone metastases are not considered measurable. Minimum indicator lesion size ≥10 mm by helical CT or ≥20 mm by conventional techniques.
Pathological nodes must be ≥15 mm by the short axis to be considered measurable.
Age ≥18, as no dosing or adverse event data are currently available on the use of neratinib or temsirolimus in patients <18 years of age, children are excluded from this study.

Able and willing to consent for biopsy of metastatic breast cancer prior to treatment. Consent to preservation of frozen and fixed samples of tumor cores for evaluation.

Consent to evaluation of primary tumor biopsy specimen.

Patients must be willing to discontinue sex hormonal therapy, e.g., birth control pills, hormonal replacement therapy, prior to enrollment. Women of childbearing potential must consent to effective contraception while on treatment and for a period thereafter.

Negative serum HCG pregnancy test for premenopausal women of reproductive capacity and for women less than 12 months after menopause.

Asymptomatic, central nervous system metastases are permitted if patients remain clinically stable after discontinuation of steroids and anticonvulsants for 3 months.

Eastern Cooperative Oncology Group (ECOG) performance status score of ≤2.

Patients must have normal organ and marrow function: AST/ALT ≤2.5× institutional upper limit of normal except for patients with liver metastases. For patients with liver metastases, AST/ALT/Alkaline phosphatase ≤5.0× institutional upper limit of normal. Total bilirubin within institutional limits except for patients with liver metastases. For patients with liver metastases, total bilirubin ≤1.5× institutional upper limit of normal. Creatinine clearance within normal limits or ≥60 mL/min, PT and PTT ≤1.5× institutional upper limit of normal except for patients on Coumadin or low molecular weight heparin, leukocytes ≥3,000 μl, absolute neutrophil count ≥1,000 μl, and platelets ≥75,000 μl Able to swallow and retain oral medication.

Exclusion Criteria:

Potential subjects will be excluded from enrollment into this study if they meet any of the following criteria:

Patients receiving any concurrent anticancer therapy or investigational agents with the intention of treating breast cancer.

History of allergic reactions attributed to compounds of similar chemical or biologic composition to neratinib or temsirolimus.

Unable to consent to biopsy of metastatic disease or for whom a biopsy would be medically unsafe.

Women who are pregnant or breast feeding.

Life expectancy <3 months.

Completion of previous chemotherapy regimen <3 weeks prior to the start of study treatment. Prior hormonal therapy must be discontinued prior to treatment start. Biologic therapy with bevacizumab for the treatment of metastatic disease must be discontinued ≥3 weeks from the start of protocol treatment.

Concurrent radiotherapy is not permitted for disease progression on treatment on protocol, but might be allowed for pre-existing non-target lesions with approval from the principal investigator of the trial.

Concurrent medical conditions which may increase the risk of toxicity, including ongoing or active infection, history of significant bleeding disorder unrelated to cancer (congenital bleeding disorders, acquired bleeding disorders within one year), HIV-positive or active hepatitis.

History of clinically significant or uncontrolled cardiac disease, including congestive heart failure, angina, myocardial infarction, arrhythmia, and left ventricular ejection fraction less than 50% measured by a multigated blood pool imaging of the heart (MUGA scan) or an echocardiogram (ECHO).

QTc interval >0.47 seconds.

Patients with GI tract disease resulting in an inability to take oral medication, malabsorption syndrome, a requirement for IV alimentation, prior surgical procedures affecting absorption, or uncontrolled inflammatory GI disease.

History of an invasive second primary malignancy diagnosed within the previous 3 years, except for stage I endometrial or cervical carcinoma or prostate carcinoma treated surgically, and non-melanoma skin cancer.

History of uncontrolled seizures, central nervous system disorders or psychiatric disability judged by the investigator to be clinically significant, precluding informed consent, or interfering with compliance of oral drug intake.

Unwillingness to give written informed consent, unwillingness to participate, or inability to comply with the protocol for the duration of the study. Willingness and ability to comply with scheduled visits, treatment plan, laboratory tests and other study procedures are necessary to participation in this clinical trial.

Example 3—HER2 Amplified Gastric Cancer

Study Type: Interventional
Study Design:
Allocation: Non-Randomized
Endpoint Classification: Safety/Efficacy Study
Intervention Model: Single Group Assignment
Masking: Open Label
Primary Purpose: Treatment
Outcome Measures The percentage of patients demonstrating clear evidence of inhibition of receptor auto-phosphorylation in HER-2 amplified patients on Day 30.

Objective Response Rate
Eligibility
Ages Eligible for Study: 21 Years and older
Genders Eligible for Study: Both
Accepts Healthy Volunteers: No
Inclusion Criteria:

Male or female patients 21 years of age or older at the time written informed consent is obtained.

Patients with histologically confirmed adenocarcinoma of the stomach, gastro-oesophageal junction or distal oesophagus with inoperable locally-advanced metastatic disease.

Patients with tumours with gene-amplification of HER-2 by standard FISH.

Patient has received 1 or more prior chemotherapy for the treatment of adenocarcinoma of the stomach, gastro-oesophageal junction or distal oesophagus with metastatic disease.

Patients with prior partial gastrectomy if they can take oral medications, and can undergo gastroendoscopic biopsies and meet all other inclusion/exclusion criteria.

Patients with measurable and non-measurable disease per modified RECIST guidelines. All scans and x-rays used to document measurable or non-measurable disease must be done within a 28-day period prior to enrollment.

Patient with Eastern Cooperative Oncology Group (ECOG) performance status of 0 or 1 (within 14 days prior to enrolment).

Patient with adequate organ and hematological function as evidenced by the following laboratory studies within 14 days prior to enrollment:

Hematological function, as follows: Absolute neutrophil count (ANC) ≥1.5×109/L; Platelet count ≥75×109/L; Hemoglobin ≥9 g/dL;

Coagulation functions, as follows: Partial thromboplastin time (PTT) or activated partial thromboplastin time (aPTT)

≤1.5× upper limits of normal (ULN) per institutional laboratory normal range; International normalized ratio (INR) ≤1.5

Renal functions, as follows: Serum creatinine ≤1.5×ULN; Urea ≤1.5×ULN

Hepatic function, as follows: Total bilirubin ≤1.5×ULN; Serum glutamic oxaloacetic transaminase (SGOT)/aspartate transaminase (AST) and serum glutamic pyruvic transaminase (SGPT)/alanine transaminase (ALT) ≤2.5×ULN (≤5× ULN if liver metastases are present)

Exclusion Criteria:

Patients unable to swallow oral medications

Patients with persistent gastric outlet obstruction, complete dysphagia or feeding jejunostomy.

Patients who underwent radiotherapy to the gastric remnant ≤14 days prior to enrolment. Patients must have recovered from all radiotherapy-related toxicities.

Patients with total gastrectomy.

Patients who have uncontrolled, clinically significant symptomatic cardiovascular diseases within 6 months prior to enrolment, including myocardial infarction, unstable angina, grade 2 or greater peripheral vascular disease, cerebrovascular accident, transient ischemic attack, congestive heart failure or arrhythmias not controlled by outpatient medication.

Pregnant (i.e., positive beta-human chorionic gonadotropin test) or is breast-feeding women.

Example 4—HER2 Amplified Lung Cancer

Study Type: Interventional
Study Design:
Allocation: Non-Randomized
Endpoint Classification: Safety/Efficacy Study
Intervention Model: Single Group Assignment
Masking: Open Label
Primary Purpose: Treatment
Outcome Measures
Progression-Free Survival (PFS); Progression Free Survival rate (PFS) at 4 months [Cohort A] PFS is defined as the interval from enrollment to date of objective progression or death due to any cause.
Duration of Response (DR) per cohort
Overall Survival (OS) per cohort
Patient Reported Outcomes of health related quality of life and disease/treatment-related symptoms as measured by the European Organization for Research and Treatment of Cancer Quality of Life Questionnaire (EORTC QLQ-C30), and Lung Cancer module (LC13)
Eligibility
Ages Eligible for Study: 21 Years and older
Genders Eligible for Study: Both
Accepts Healthy Volunteers: No
Inclusion Criteria:
Advanced adenocarcinoma of lung, measurable disease
Patients with tumours with gene-amplification of HER-2 by standard FISH regardless of smoking status
ECOG (Eastern Cooperative Oncology Group) 0-1.
Cohort A: No prior systemic therapy
Cohort B: patients with HER2 amplified NSCLC; may have had prior therapy
Exclusion Criteria:
Active brain metastases
Prior systemic therapy for advanced disease in Cohort A only. Cohort B can have had any number of prior lines of systemic therapy.

Example 5

Cell lines BT-474, Mino, and DoHH2 were obtained from ATCC and cultured as indicated from the source.

Kinase Activity Assay:

Kinase activity assay was performed using the LabChip platform by Nanosyn, Inc. using 5 nM of recombinant enzymes (EGFR, HER2, and HER4) and various concentrations of the inhibitors (e.g. ibrutinib, afatinib, neratinib, dacomitinib, lapatinib, and gefitinib).

For DoHH2 cells, the following protocol was used. DoHH2 cells (1 million/mL) were treated with inhibitors for 1 h, followed with 30 min treatment of PCI-33380 (2 uM). Cells were then pelleted and resuspended in 24 uL PBS with protease inhibitors. Next, the cells were freeze-thaw 4 times. 24 uL supernatant of the cell lysate was mixed with 8 uL 4× Invitrogen sample buffer. About 15 uL of the cell lysate mixture was loaded onto each well of an electrophoresis gel.

Figure 19A:
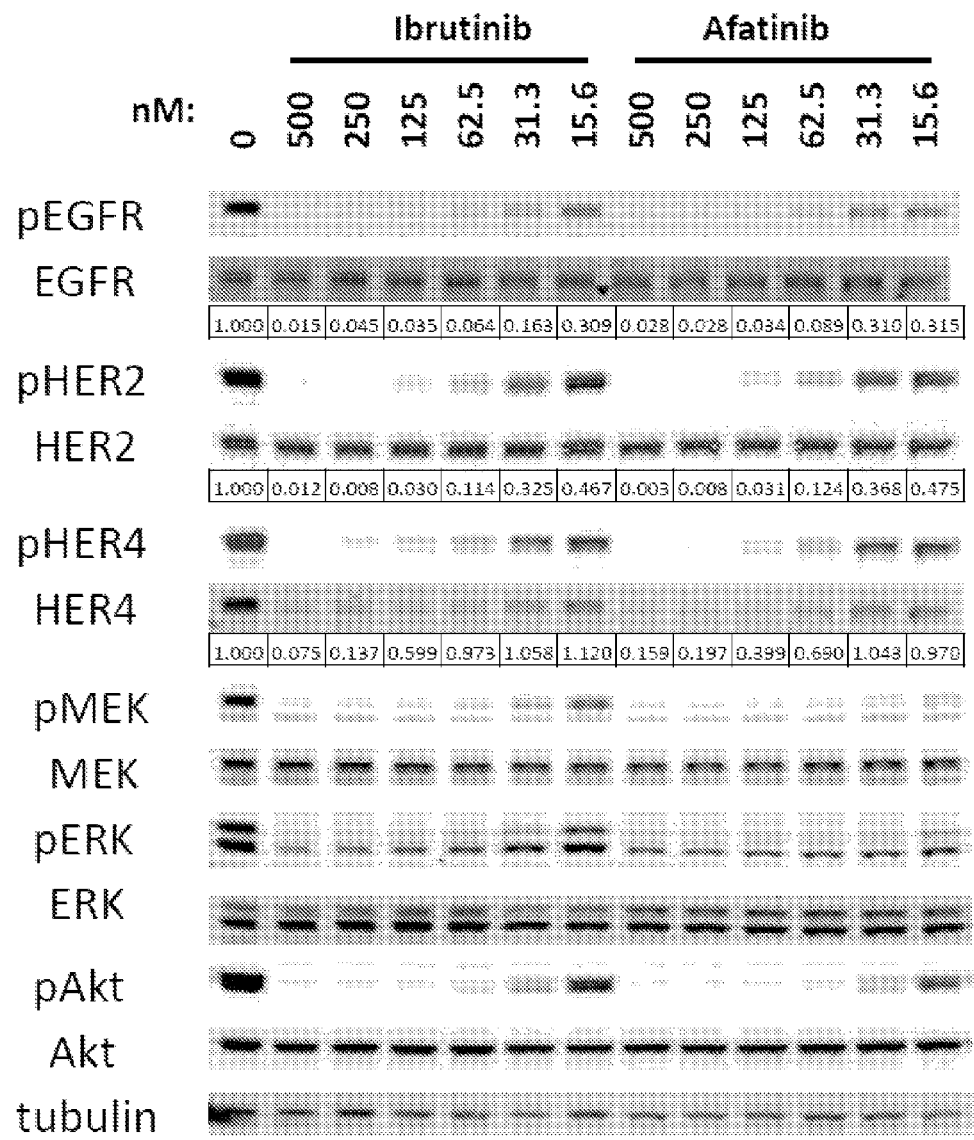
Figure 20:
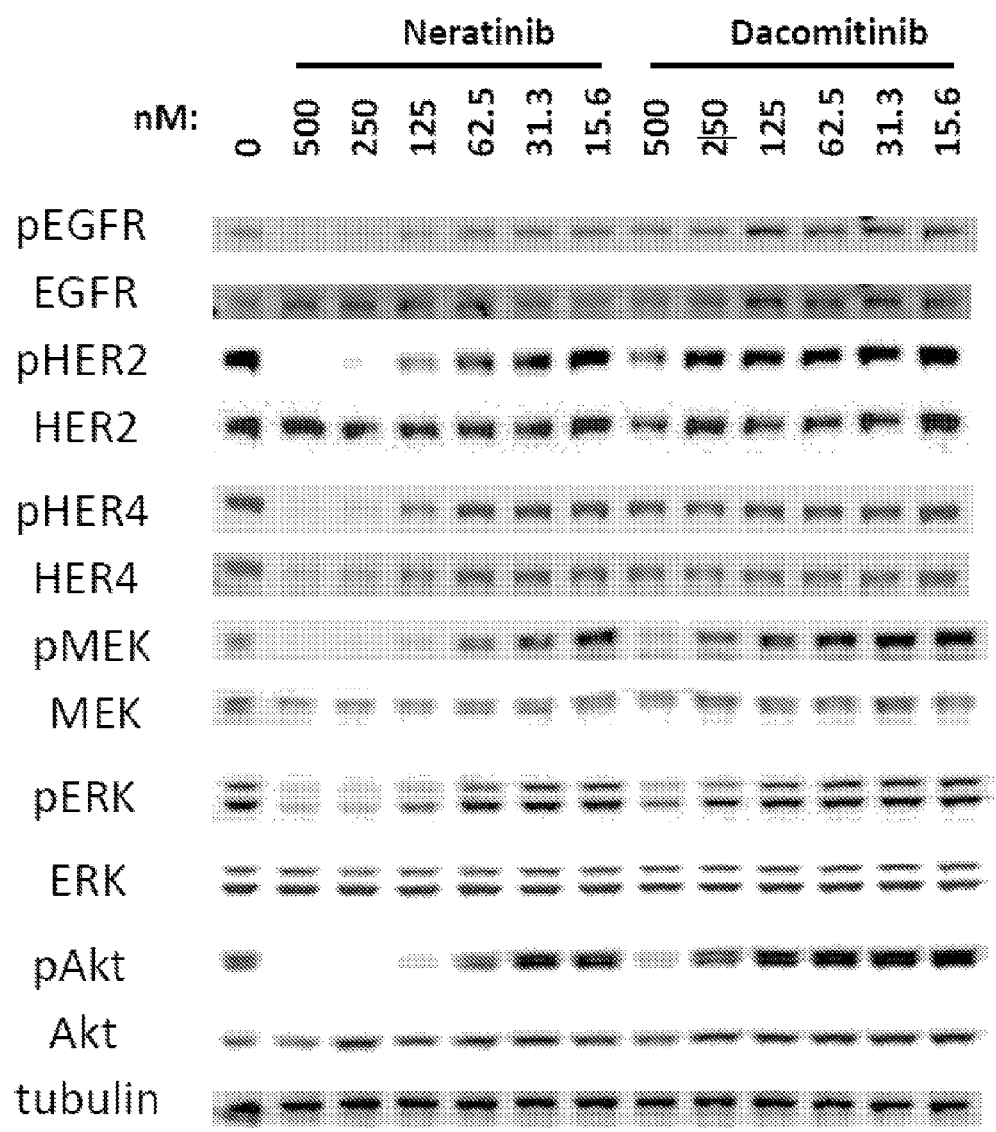
FIG. 20: exemplifies the signaling pathway inhibition of neratinib and dacomitinib. Dacomitinib is less effective at inhibiting the signaling pathways.
Figure 21:
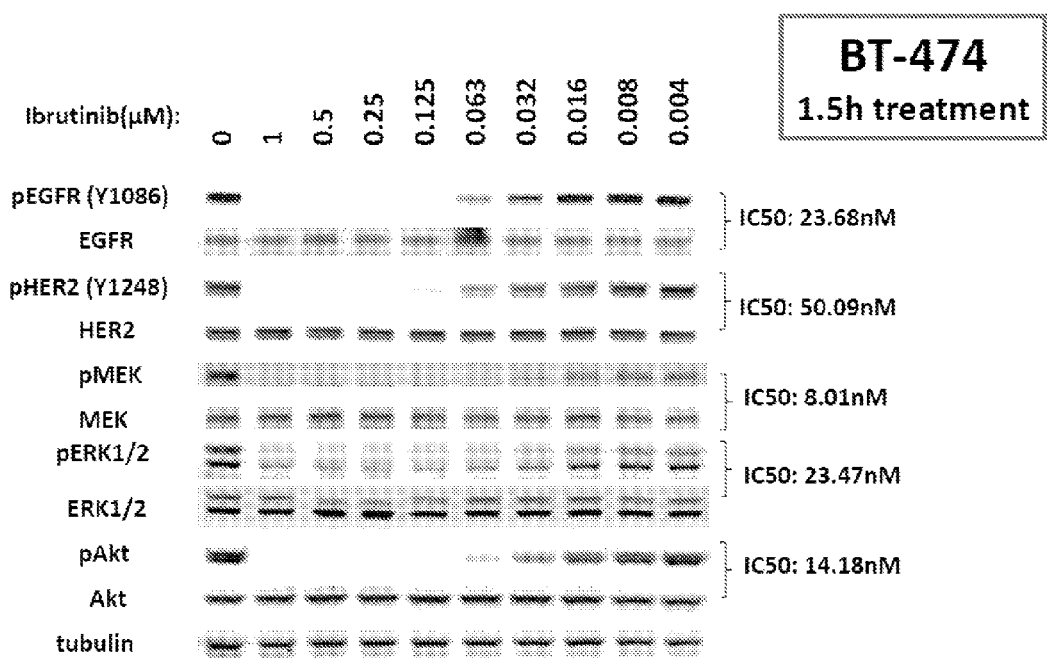
FIG. 21: exemplifies ibrutinib as a more potent inhibitor of MEK and Akt pathways than the EGFR and HER2 pathways.
Figure 22A:
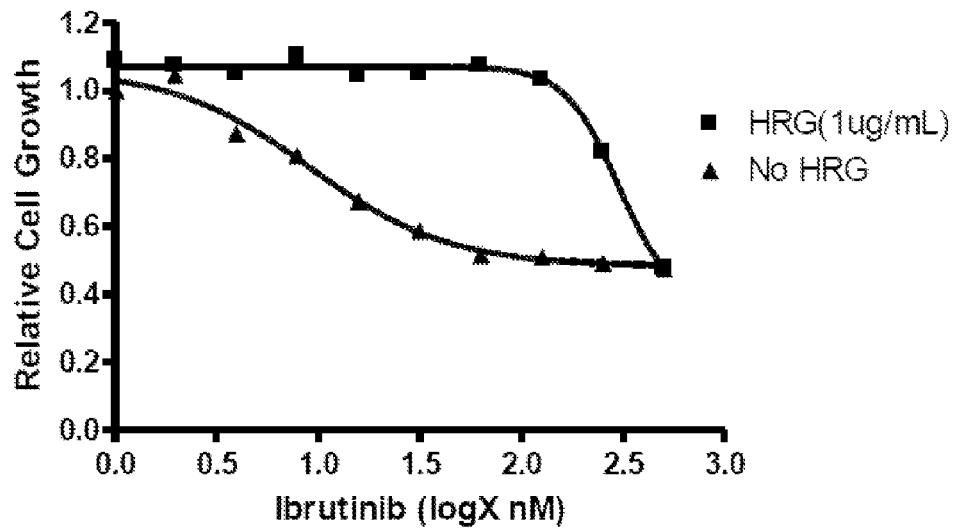
FIG. 22A-FIG. 22C: exemplify the concentrations of ibrutinib to overcome resistance induced by heregulin in BT-474 cells (A) and MDA-MB-453 cells (B). C illustrates ibrutinib inhibition as assessed by phosphorylation of HER2 and additional downstream targets in the presence or absence of heregulin.
Figure 22B:
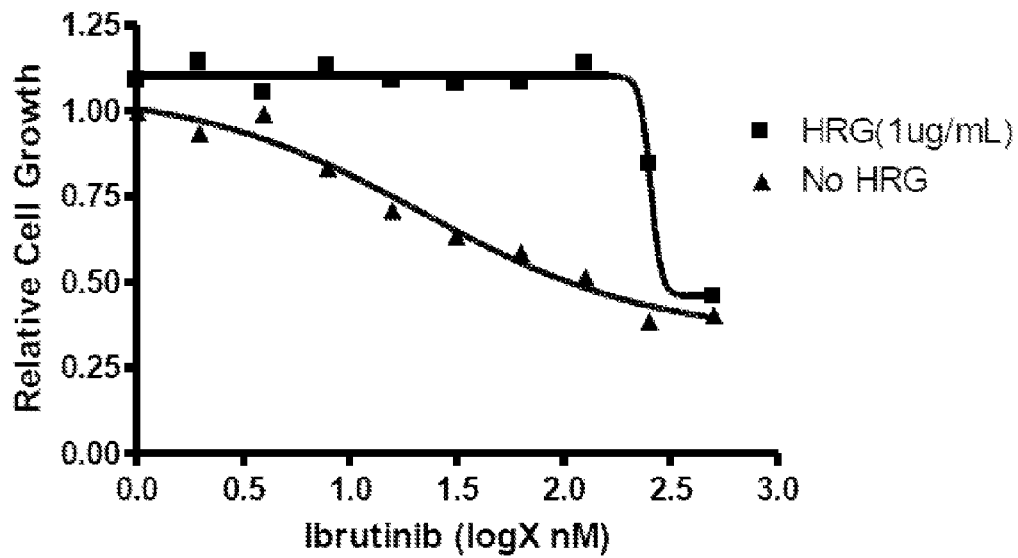
Figure 22C:
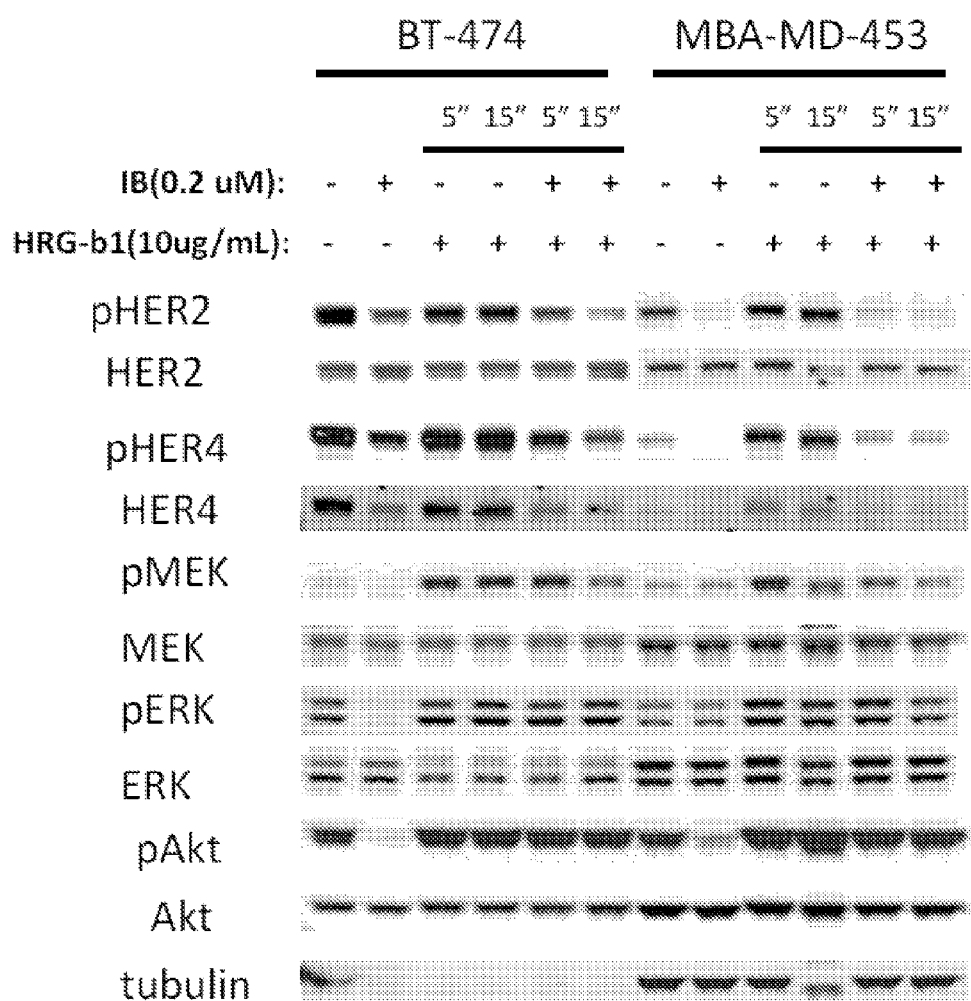
Figure 23:
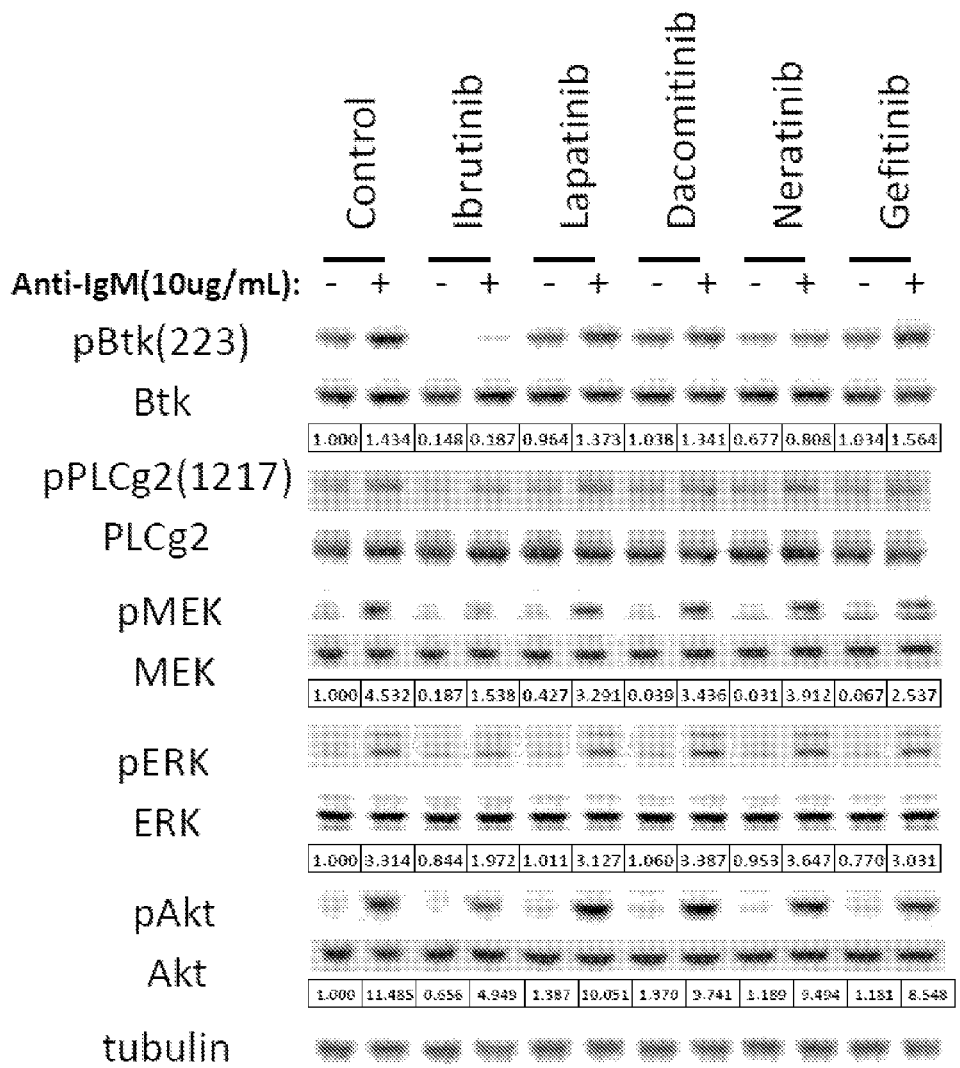
FIG. 23: exemplifies ibrutinib inhibition on several signaling pathways in B cells. Ibrutinib selectively inhibits the Btk signaling pathway in Mino cells.
Figure 24:
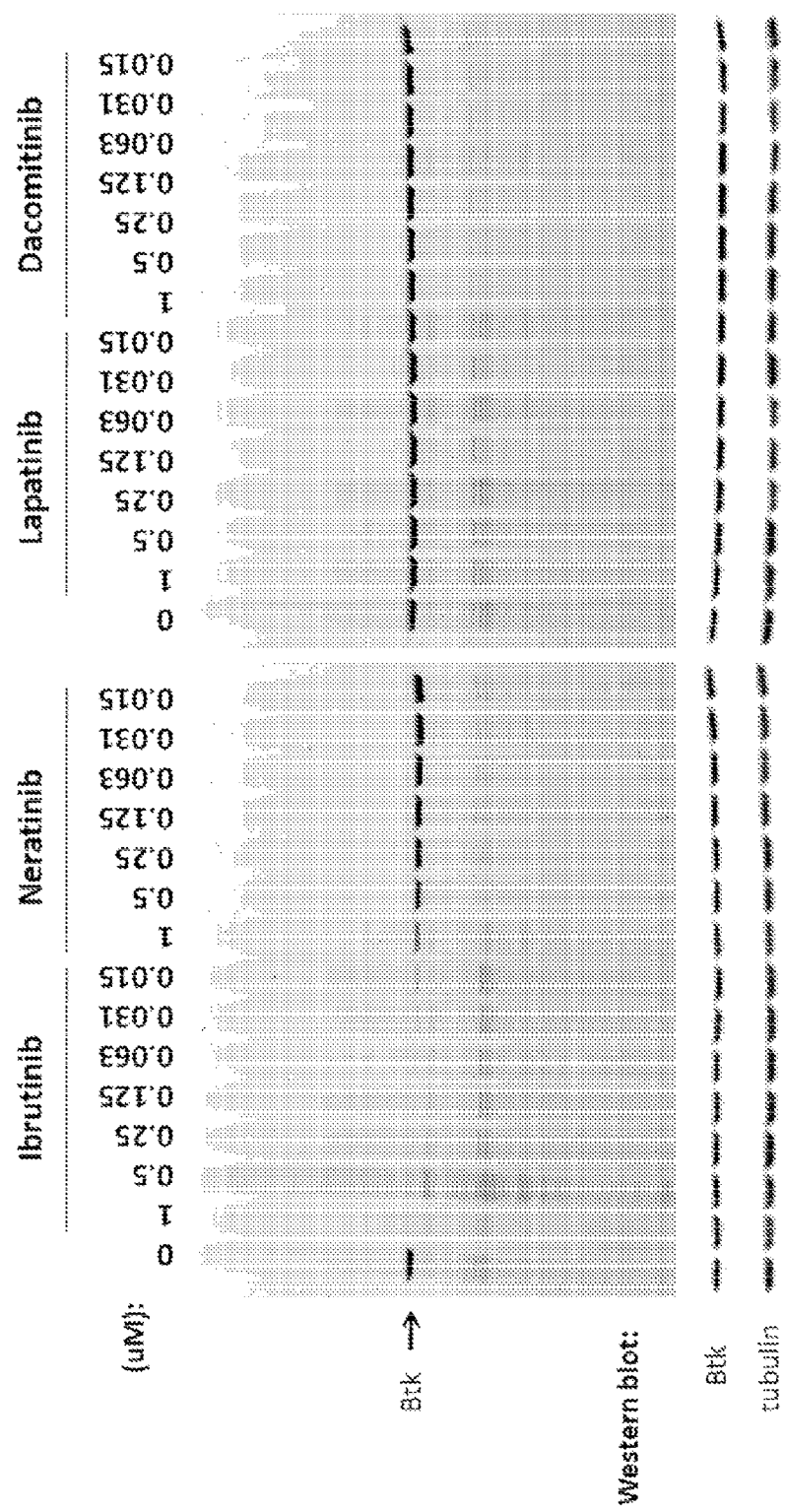
FIG. 24: exemplifies ibrutinib as covalently binds to Btk.

The inhibition of the signaling pathway by ibrutinib was compared with afatinib (see, e.g. FIG. 19). Both ibrutinib and afatinib showed greater inhibitor, i.e. higher IC50, toward EGFR than for HER2 and HER4 (see, e.g. FIG. 19B). Dacomitinib, a pan-ErbB inhibitor, was less effective in inhibiting the EGFR and downstream targets (see, e.g. FIG. 20). Ibrutinib was a potent inhibitor of the MEK and Akt signaling pathway than of the EGFR and HER2 signaling pathway (see, e.g. FIG. 21). Furthermore, a higher concentration of ibrutinib was able to overcome resistance induced by heregulin (see, e.g. FIG. 22). In comparison with additional inhibitors described herein, only ibrutinib showed selective inhibitory effect on Btk signaling pathways in B cells (e.g. Mino cells) (see, e.g. FIG. 23). Further, ibrutinib selectively bound to Btk covalently, while the remaining inhibitors, neratinib, lapatinib, and dacomitinib, did not (see, e.g. FIG. 24).

Example 6

Covalent Binding of Ibrutinib to ErbB Kinases

Cell lines BT474 and SK-BR-3 were obtained from ATCC and cultured as indicated from the source.

BTK Dialysis Assay:

100 nM and 10 nM compound was pre-incubated with 5 nM BTK enzyme for 1 h in a buffer comprising 100 mM HEPES pH7.5, 0.1% BSA, 5 mM MgCl2, 1 mM DTT, 0.01% Triton X-100 and was dialyzed at +4° C. against the same buffer for a total time of 24 h (3 changes of the dialysis buffer, nominal cumulative dialysis factor: 8,000,000). Control samples included DMSO+5 nM BTK dialyzed in the identical manner. Un-dialyzed samples with compound were assembled and pre-incubated for 1 hr. Following dialysis, the BTK activity was measured in real-time format in the presence of 250 uM ATP and 1 uM substrate peptide. Initial velocity was determined in the samples.

LCK Dialysis Assay:

100 nM and 10 nM compound was pre-incubated with 5 nM LCK enzyme for 1 h in a buffer comprising 100 mM HEPES pH7.5, 0.1% BSA, 5 mM MgCl2, 1 mM DTT, 0.01% Triton X-100 and was dialyzed at +4° C. against the same buffer for a total time of 24 h (3 changes of the dialysis buffer, nominal cumulative dialysis factor: 8,000,000). Control samples included: DMSO+5 nM LCK dialyzed in the identical manner. Un-dialyzed samples with compound were assembled and pre-incubated for 1 hr. Following dialysis, the LCK activity was measured in real-time format in the presence of 50 uM ATP and 1 uM substrate peptide. Initial velocity was determined in the samples.

EGFR Dialysis Assay:

100 nM and 10 nM compound was pre-incubated with 5 nM EGFR enzyme for 1 h in a buffer comprising 100 mM HEPES pH7.5, 0.1% BSA, 5 mM MgCl2, 1 mM DTT, 0.01% Triton X-100 and dialyzed at +4° C. against the same buffer for a total time of 24 h (3 changes of the dialysis buffer, nominal cumulative dialysis factor: 8,000,000). Control samples included: DMSO+5 nM EGFR dialyzed in the identical manner. Un-dialyzed samples with compound were assembled and pre-incubated for 1 hr. Following dialysis, the EGFR activity was measured in real-time format in the presence of 250 uM ATP and 1 uM substrate peptide. Initial velocity was determined in the samples.

HER4 Dialysis Assay:

100 nM and 10 nM compound was pre-incubated with 5 nM HER4 enzyme for 1 h in a buffer comprising 100 mM HEPES pH7.5, 0.1% BSA, 5 mM MgCl2, 1 mM DTT, 0.01% Triton X-100 and dialyzed at +4° C. against the same buffer for a total time of 24 h (3 changes of the dialysis buffer, nominal cumulative dialysis factor: 8,000,000). Control samples included: DMSO+5 nM HER4 dialyzed in the identical manner. Un-dialyzed samples with compound were assembled and pre-incubated for 1 hr. Following dialysis, the HER4 activity was measured in real-time format in the presence of 250 uM ATP and 1 uM substrate peptide. Initial velocity of was determined in the samples.

Figure 25A:
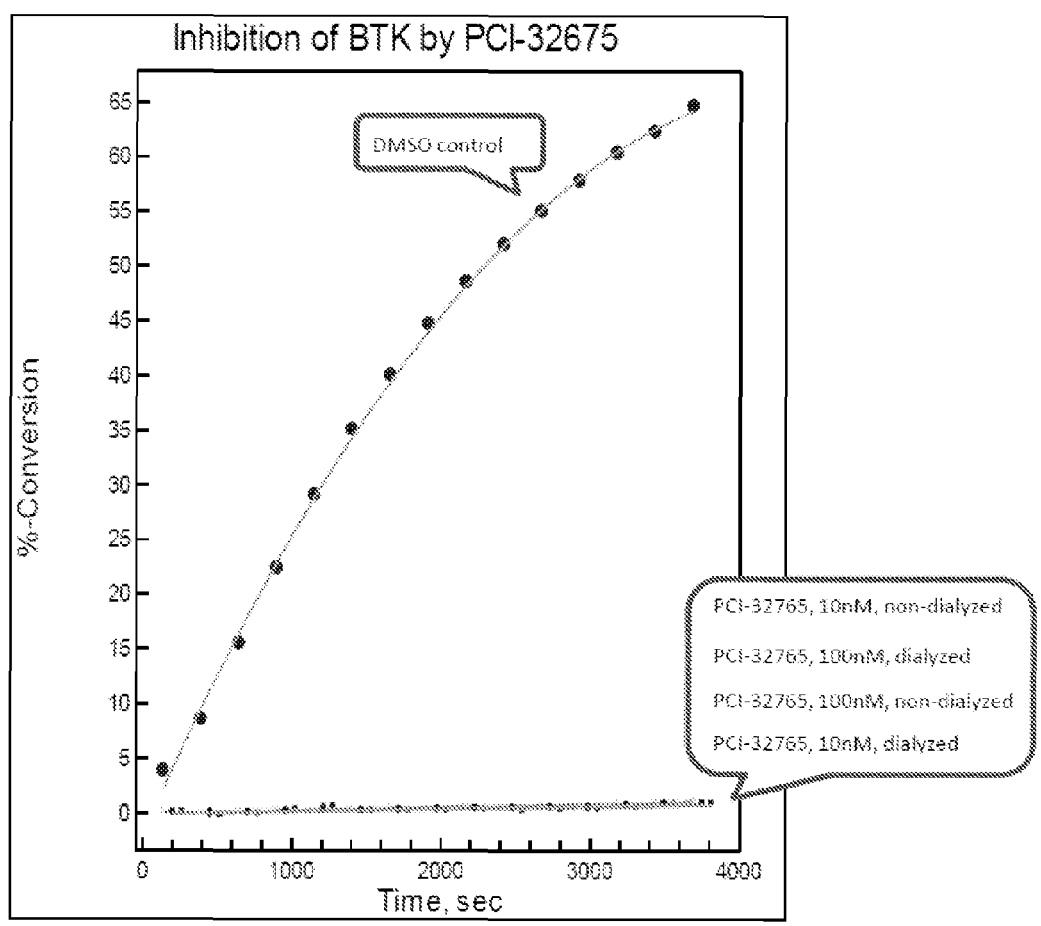
Figure 25C:
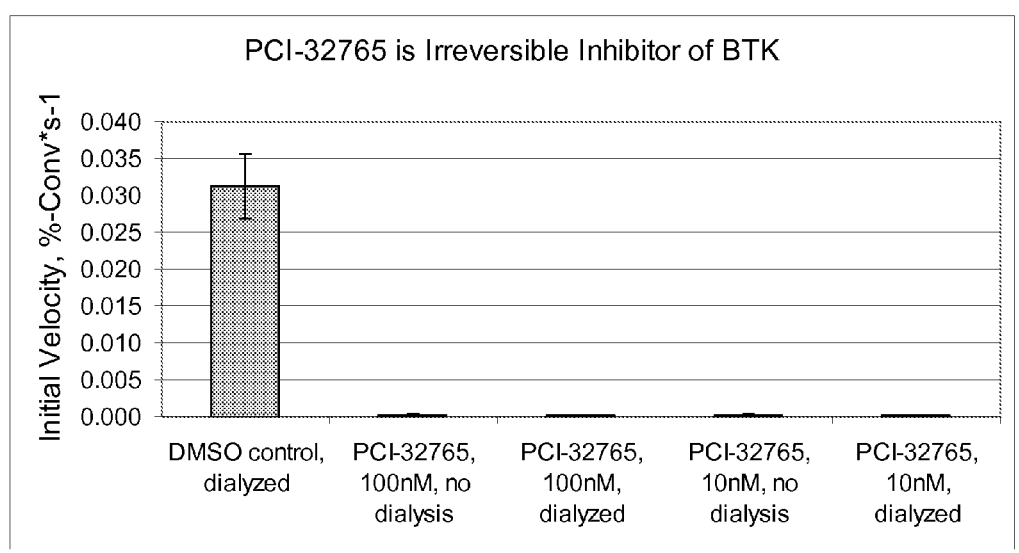
Figure 26A:
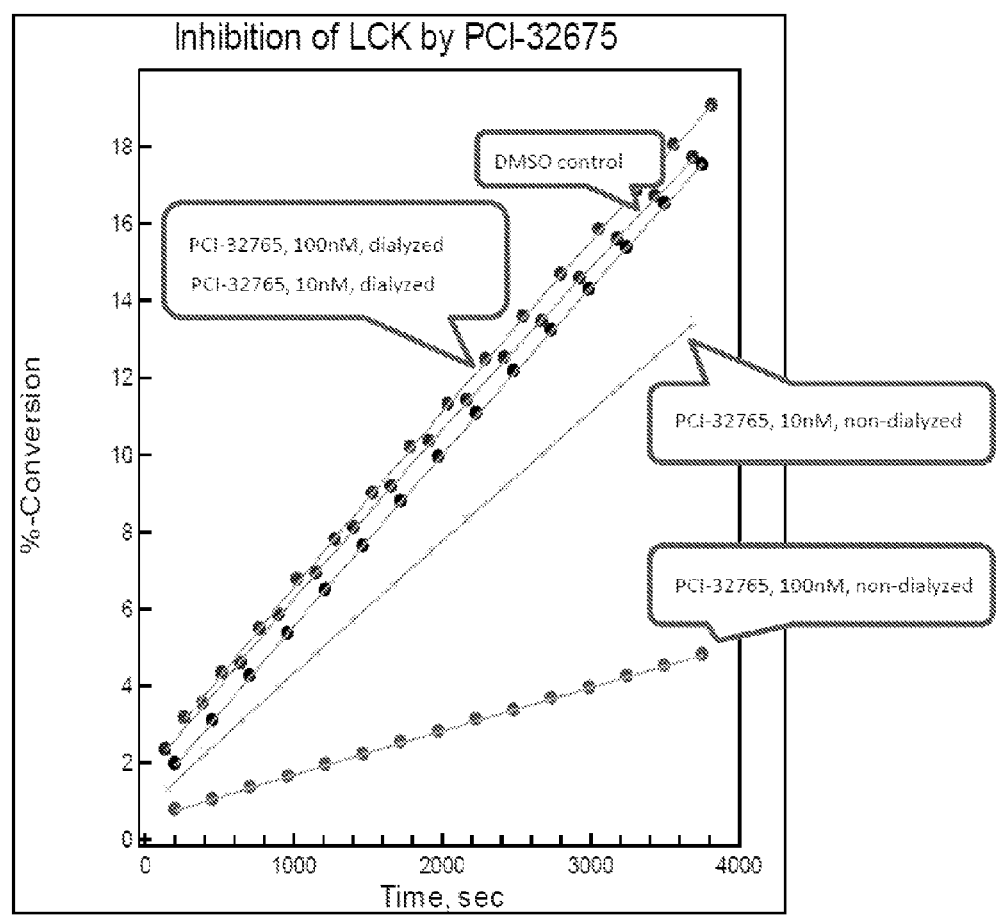
Figure 26C:
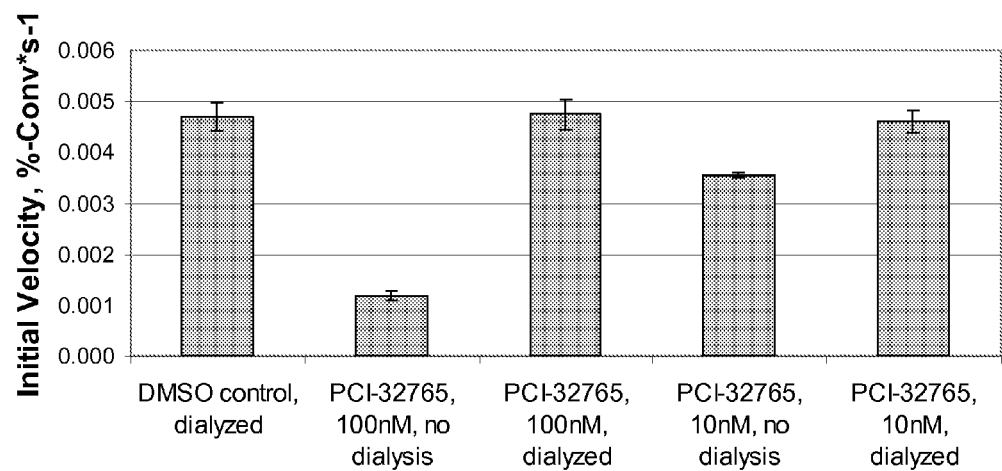
Figure 27A:
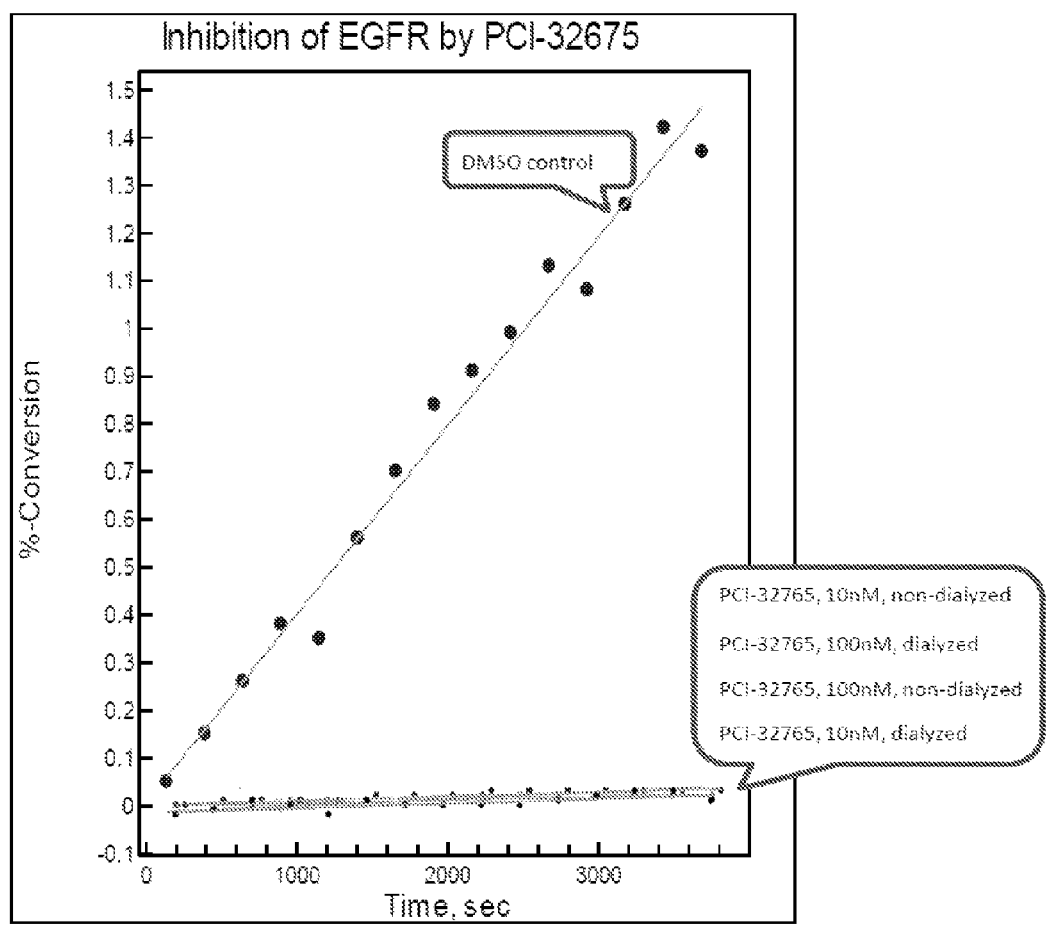
Figure 27C:
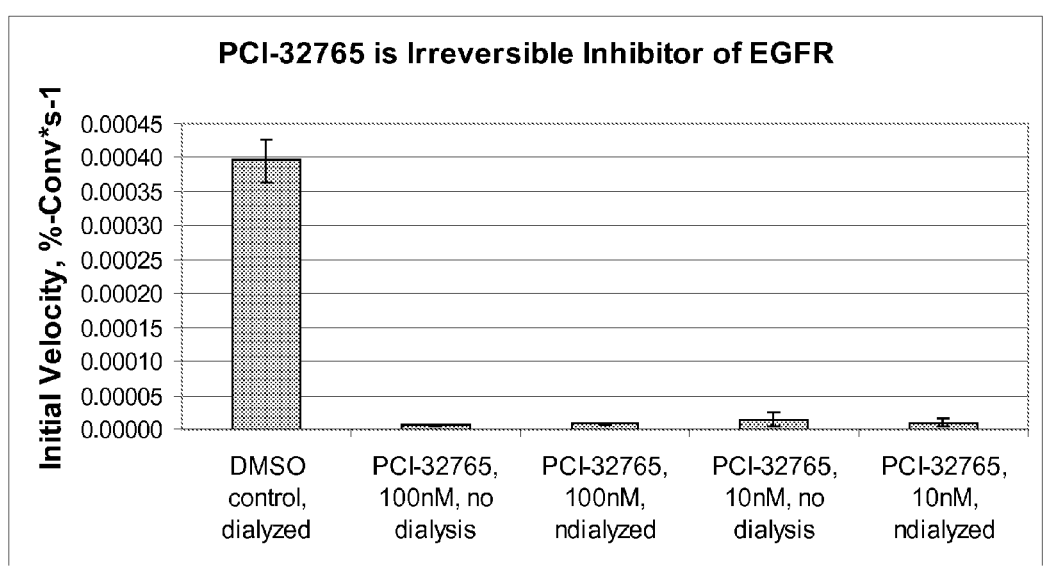
Figure 28A:
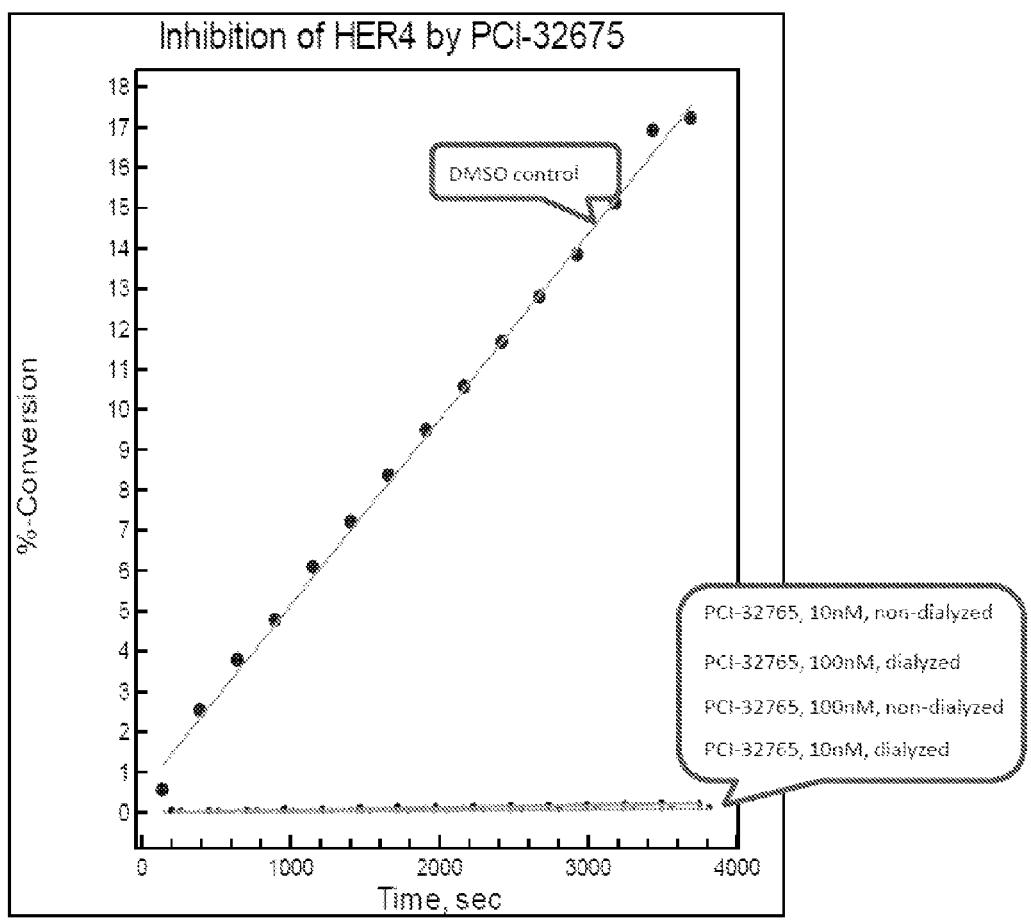
Figure 28C:
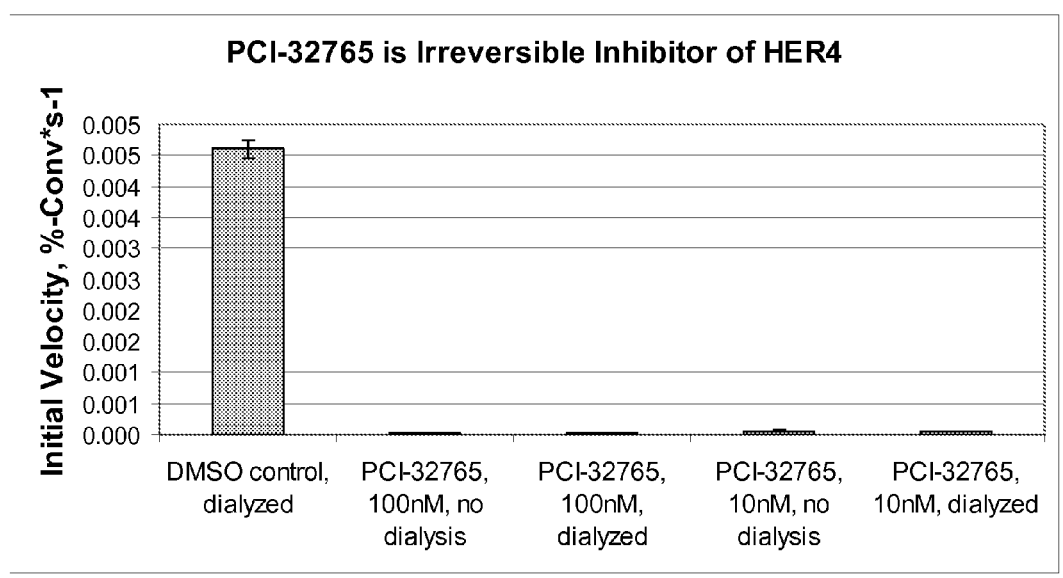

Recombinant enzymes BTK, EGFR, and HER4 were dialyzed against either 10 nM or 100 nM concentration of ibrutinib. Ibrutinib (PCI-32765) demonstrated irreversible inhibition of BTK (see, e.g. FIG. 25). In the presence of LCK, ibrutinib demonstrated reversible inhibition (see, e.g. FIG. 26). Lymphocyte-specific protein tyrosine kinase (LCK) served as a negative control. LCK lacks the conserved cysteine residue in its kinase domain, and its activity was recovered following dialysis after 1 h pre-exposure to ibrutinib. In the presence of EGFR and HER4, ibrutinib showed both irreversible inhibition to both recombinant enzymes (see, e.g. FIG. 27 for EGFR inhibition and FIG. 28 for HER4 inhibition). The enzymes in DMSO (control) were dialyzed as well.

Example 7

Time Dependent Inhibition by Ibrutinib (PCI-32765) Thru Rapid Dilution

Figures 29A, 29B:
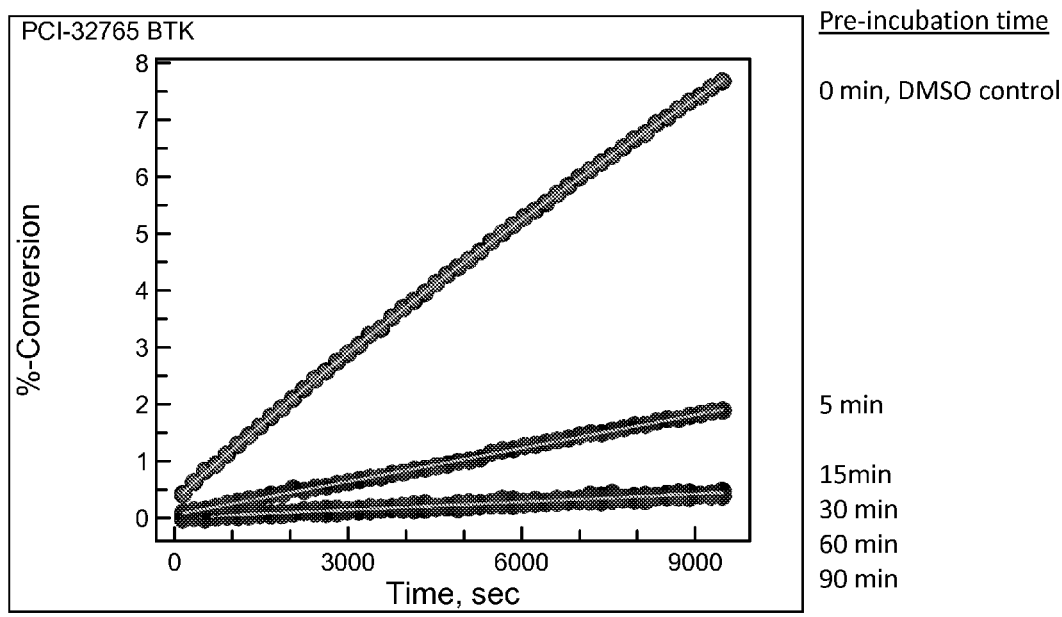
FIG. 29A-FIG. 29D: exemplify time-dependent inhibition of BTK by ibrutinib after rapid dilution.
Figures 29C, 29D:
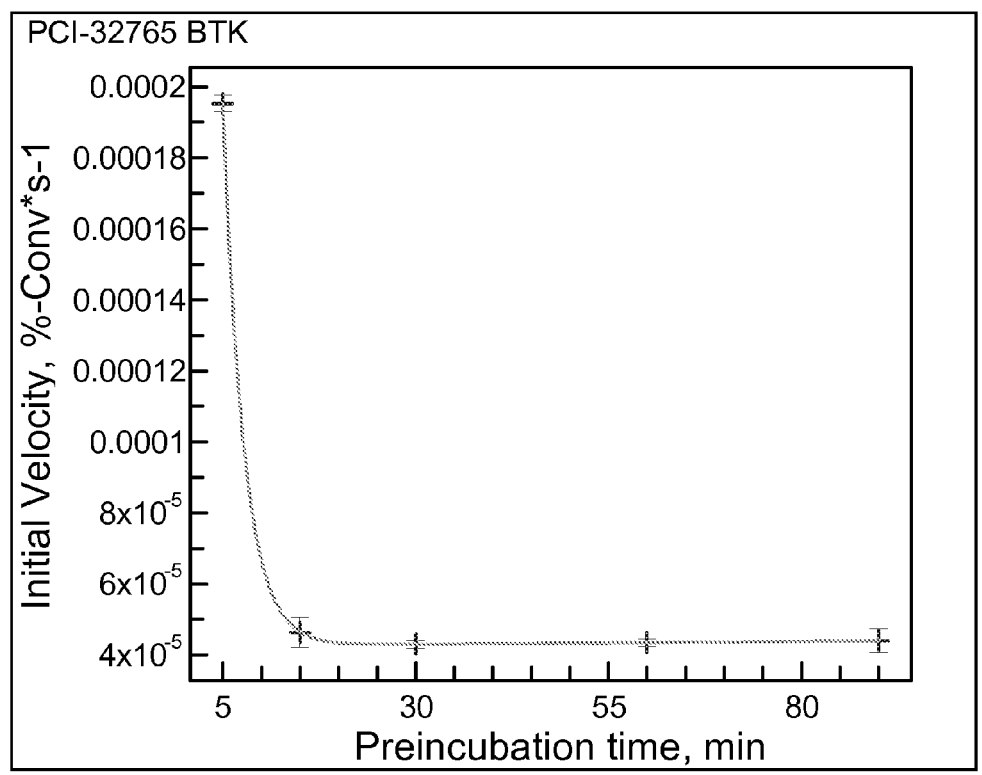
Figures 30A, 30B:
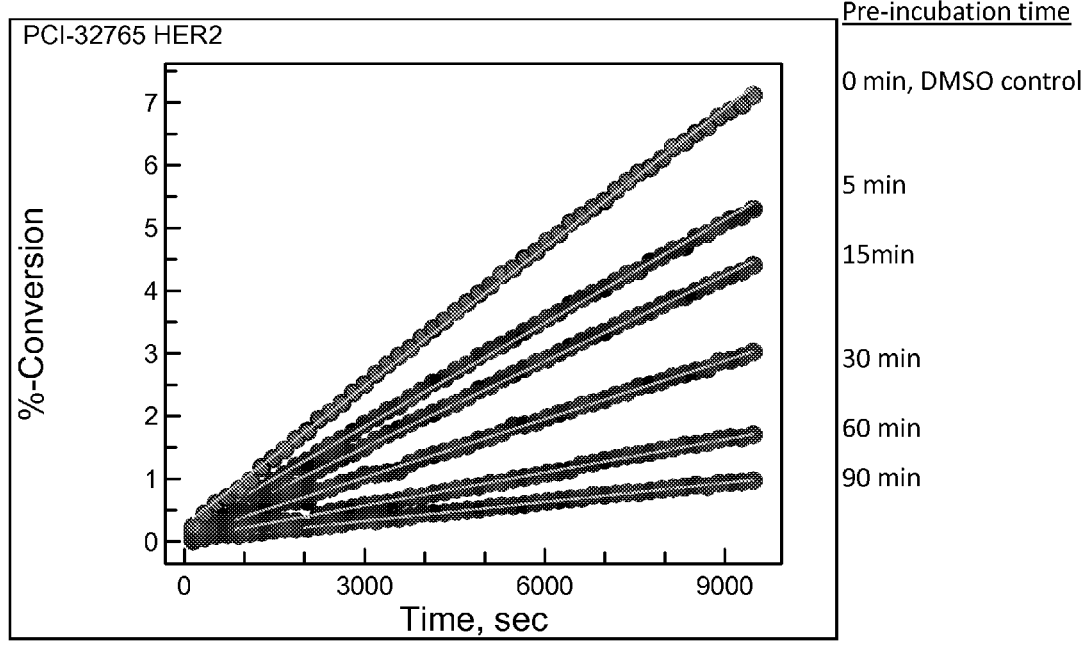
FIG. 30A-FIG. 30D: exemplify time-dependent inhibition of HER2 by ibrutinib after rapid dilution.
Figures 30C, 30D:
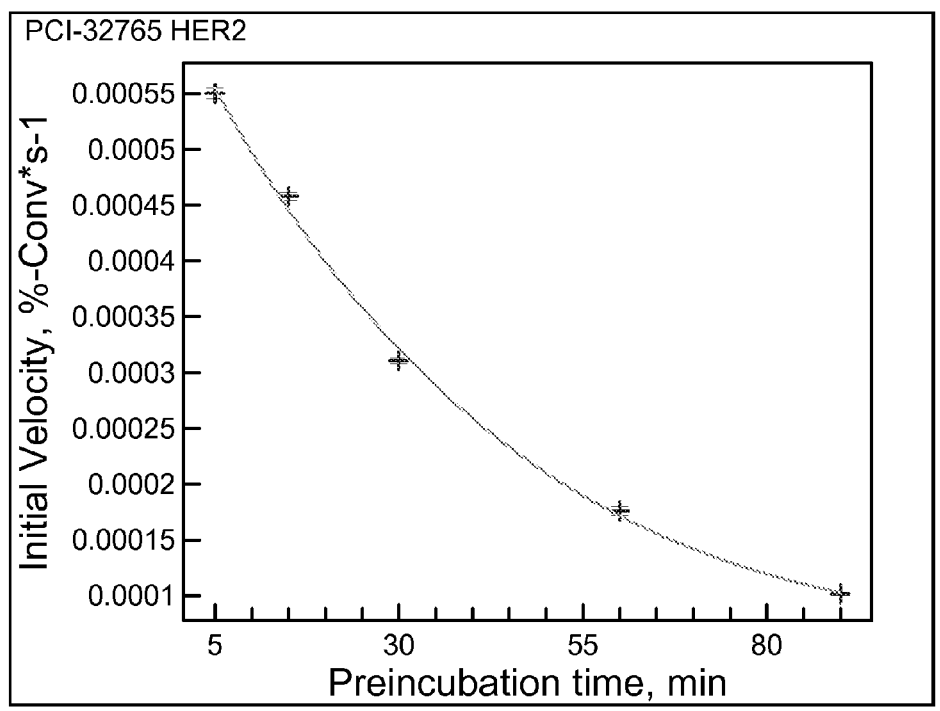

Ibrutinib (PCI-32765) was tested against two recombinant kinases, Btk and HER2. Ibrutinib was tested at 0.1 µM concentration. Ibrutinib or DMSO (control) was pre-incubated with either Btk or HER2 for 5 min, 15 min, 30 min, 60 min and 90 min (the pre-incubation samples were assembled in reverse order: 90 min, 60 min, 30 min, 15 min, and 5 min). The Ibrutinib/kinase complexes were rapidly diluted (dilution factor 500×) into assay buffer with 500 uM ATP and 2 uM substrate peptide. Real time enzyme activity assay was performed in the diluted samples. The time-dependent irreversibility of the inhibitor was determined by the difference between the treated enzymes diluted in the presence of compound and without compound. The initial velocity of the reaction was plotted against pre-incubation time to determine the apparent Kobs of inhibition. FIG. 29 illustrates the time-dependent inhibition of BTK by ibrutinib after rapid dilution. FIG. 30 illustrates the time-dependent inhibition of HER2 by ibrutinib after rapid dilution.

Determining Kinetics of Inhibition by Ibrutinib (PCI-32765)

Ibrutinib (PCI-32765) was tested in BTK and HER2 assays. Compound was serially pre-diluted in DMSO. The serial dilutions were transferred into 35 mL of 1× assay buffer supplemented with 4 mM substrate peptide. The reactions were initiated by addition of 35 uL of 2× enzyme (0.5 nM BTK or 1.0 nM HER2 in 1× assay buffer supplemented with ATP.

The final BTK assay composition comprised 100 mM HEPES pH7.5, 0.1% BSA, 0.01% Triton X-100, 1 mM DTT, 5 mM $MgCl_2$, 1000 µM ATP, 0.25 nM BTK (Millipore), and 2 µM peptide. The temperature was at 25° C. DMSO concentration was at 0.05%. The peptide sequence was FAM-GEEPLYWSFPAKKK-$NH_2$ (SEQ ID NO: 2).

The final HER2 assay composition comprised 100 mM HEPES pH7.5, 0.1% BSA, 0.01% Triton X-100, 1 mM DTT, 5 mM $MnCl_2$, 1000 µM ATP, 0.5 nM HER2 (BPS), and 2 µM peptide. The temperature was at 25° C. DMSO concentration was at 0.05%. The peptide sequence was FAM-GEEPLYWSFPAKKK-$NH_2$ (SEQ ID NO: 2).

The reaction progress curves were obtained for a total time of ~4 hrs using climate controlled Caliper LabChip® instrument. The obtained curves were fitted using XLfit4 software using best fitting equation. For example: for time dependent inhibition, the equation: $[P]=V_s*t+((V_o-V_s)/K_{obs})*(1-\exp(-K_{obs}*t))$ was used. In the equation: Vi is the initial velocity of the reaction and the Vs is the steady state velocity in the presence of inhibitor.

For time dependent inhibitors: the obtained Kobs values were plotted against compound concentration using either hyperbolic fit. From the plots, the K2 (or Kinact), K-2, Ki and Kinact/Ki values were determined.

Figures 31C, 31D:
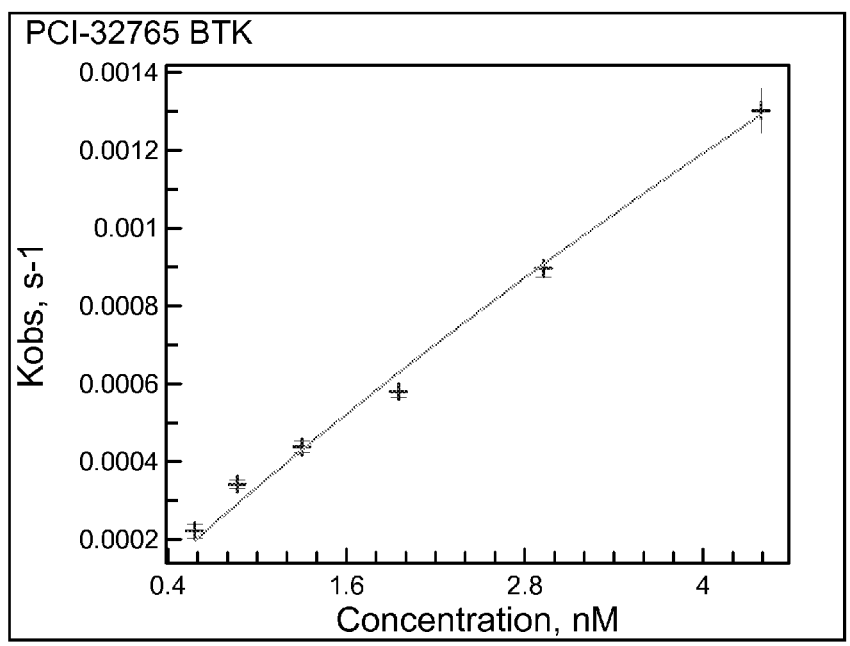
Figures 32A, 32B:
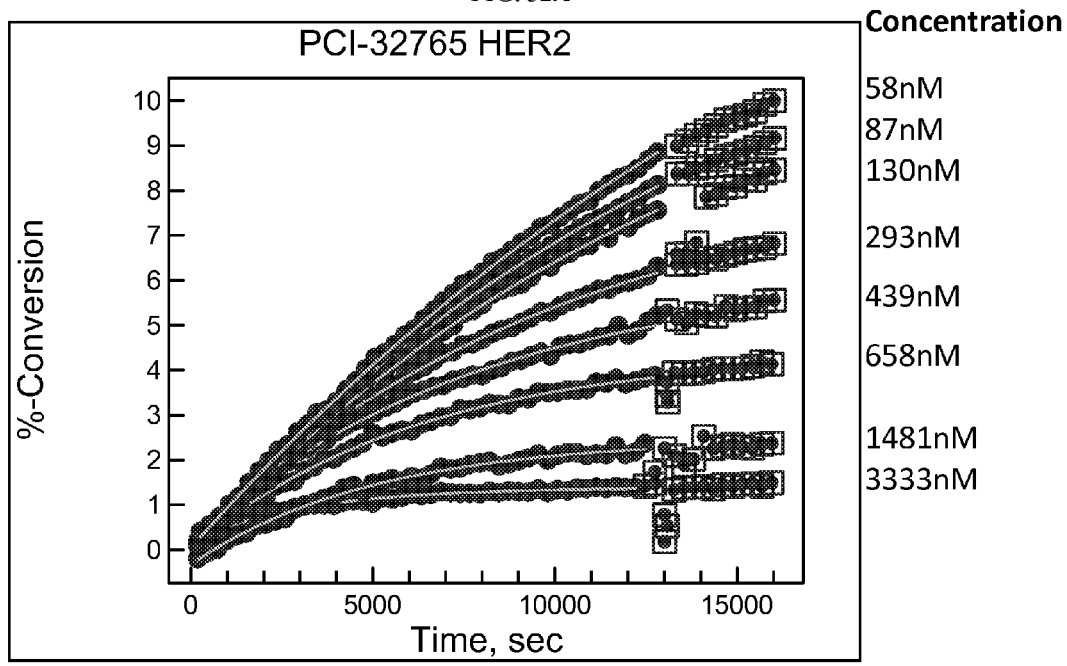
FIG. 32A-FIG. 32D: exemplify the kinetics of HER2 inhibition by ibrutinib.
Figures 32C, 32D:
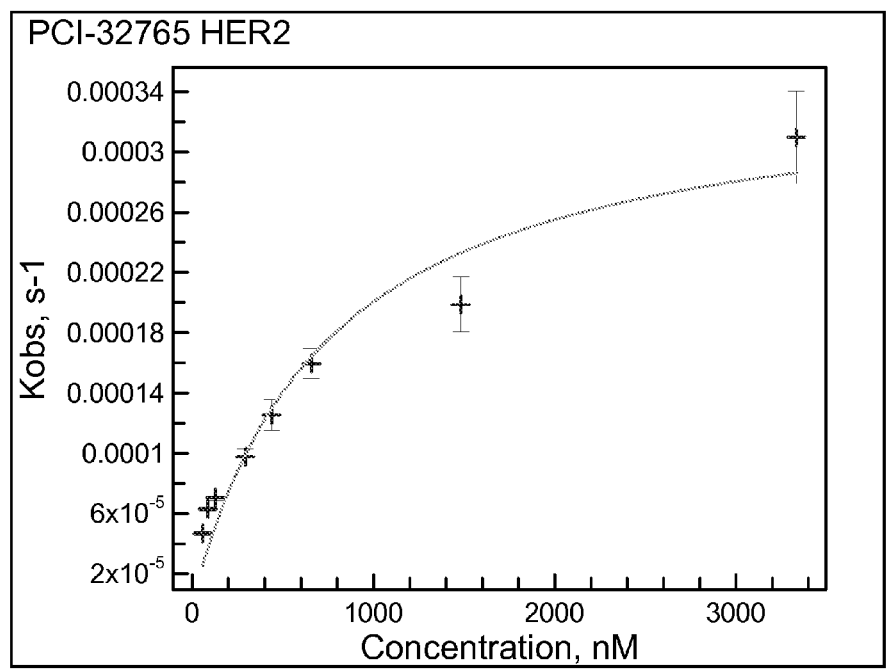

FIG. 31 illustrates the kinetics of BTK inhibition by ibrutinib (PCI-32765). FIG. 32 illustrates the kinetics of HER2 inhibition by ibrutinib (PCI-32765).

The examples and embodiments described herein are for illustrative purposes only and various modifications or changes suggested to persons skilled in the art are to be included within the spirit and purview of this application and scope of the appended claims.

What is claimed is:

1. A method for treating HER2 amplified cancer in an individual in need thereof, wherein the cancer is selected from the group consisting of colon, lung, and pancreatic cancers, and the method comprises administering to the individual in need thereof a composition comprising 1-(R)-(3-(4-amino-3-(4-phenoxyphenyl)-1H-pyrazolo[3,4-d]pyrimidin-1-yl)piperidin-1-yl)prop-2-en-1-one

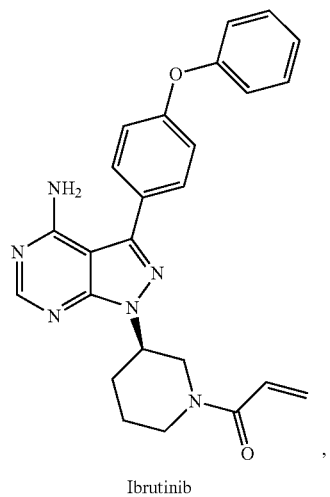 [SMILES: C=CC(=O)N1CCC[C@@H](n2nc(-c3ccc(Oc4ccccc4)cc3)c3c(N)ncnc32)C1]

Ibrutinib or a pharmaceutically acceptable salt thereof.

2. The method of claim 1, wherein the HER2-amplified cancer is metastatic.

3. The method of claim 1, wherein the HER2-amplified cancer has a HER2:CEP17 ratio of 2.2-4.0 or >4.0.

4. The method of claim 1, wherein the HER2-amplified cancer is refractory to treatment.

5. The method of claim 1, further comprising co-administering an additional therapeutic agent.

6. The method of claim 5, wherein the additional therapeutic agent is an anti-HER2 therapeutic agent, a pan-ErbB inhibitor, or an anti-VEGF therapeutic agent.

7. The method of claim 6, wherein the anti-HER2 therapeutic agent is selected from the group consisting of trastuzumab, trastuzumab emtansine, pertuzumab, lapatinib, and MM-111.

8. The method of claim 6, wherein the pan-ErbB inhibitor is selected from the group consisting of afatinib, neratinib, and dacomitinib.

9. The method of claim 6, wherein the anti-VEGF therapeutic agent is selected from the group consisting of bevacizumab, ranibizumab, lapatinib, sunitinib, sorafenib, axitinib, and pazopanib.

10. The method of claim 5, wherein the additional therapeutic agent is selected from the group consisting of: temsirolimus; paclitaxel; ASLAN001; vorinostat; doxorubicin; cyclophosphamide; cisplatin; docetaxel; dasatinib; trastuzumab and docetaxel; pertuzumab and docetaxel; doxorubicin, cyclophosphamide and paclitaxal; and doxorubicin, cyclophosphamide and fluorouracil.

11. The method of claim 1, wherein the HER2-amplified cancer is colon cancer.

12. The method of claim 1, wherein the HER2-amplified cancer is lung cancer.

13. The method of claim 1, wherein the HER2-amplified cancer is pancreatic cancer.

14. The method of claim 1, wherein the composition comprises ibrutinib.

* * * * *

UNITED STATES PATENT AND TRADEMARK OFFICE
CERTIFICATE OF CORRECTION

PATENT NO. : 10,016,434 B2
APPLICATION NO. : 15/652470
DATED : July 10, 2018
INVENTOR(S) : Jun Chen et al.

Page 1 of 1

It is certified that error appears in the above-identified patent and that said Letters Patent is hereby corrected as shown below:

On page 2, left column, the text "8,476,264" should appear as follows:
--8,776,284--

On page 2, left column, the text "8,703,760" should appear as follows:
--8,703,780--

On page 2, right column, the text "2013/0016060" should appear as follows:
--2013/0018060--

On page 3, left column, the text "2014/0126414" should appear as follows:
--2014/0128414--

On page 3, left column, the text "2014/0212465" should appear as follows:
--2014/0212485--

Signed and Sealed this
Ninth Day of April, 2019

Andrei Iancu
*Director of the United States Patent and Trademark Office*

SEQUENCE LISTING

```
<160> NUMBER OF SEQ ID NOS: 12

<210> SEQ ID NO 1
<211> LENGTH: 15
<212> TYPE: PRT
<213> ORGANISM: Unknown
<220> FEATURE:
<223> OTHER INFORMATION: Description of Unknown:
      Substrate of Bruton's tyrosine kinase

<400> SEQUENCE: 1
```

```
Ala Val Leu Glu Ser Glu Glu Leu Tyr Ser Ser Ala Arg Gln
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Glu Glu Pro Leu Tyr Trp Ser Phe Pro Ala Lys Lys Lys
1               5                   10

<210> SEQ ID NO 3
<211> LENGTH: 25
<212> TYPE: PRT
<213> ORGANISM: Homo sapiens

<400> SEQUENCE: 3

Arg Pro Ile Phe Ile Ile Thr Glu Tyr Met Ala Asn Gly Cys Leu Leu
1               5                   10                  15

Asn Tyr Leu Arg Glu Met Arg His Arg
            20                  25

<210> SEQ ID NO 4
<211> LENGTH: 25
<212> TYPE: PRT
<213> ORGANISM: Homo sapiens

<400> SEQUENCE: 4

Tyr Pro Leu Tyr Leu Val Thr Glu Tyr Leu Ser Asn Gly Cys Leu Leu
1               5                   10                  15

Asn Tyr Ile Arg Ser His Gly Lys Gly
            20                  25

<210> SEQ ID NO 5
<211> LENGTH: 25
<212> TYPE: PRT
<213> ORGANISM: Homo sapiens

<400> SEQUENCE: 5

Lys Pro Ile Tyr Ile Val Thr Glu Phe Met Glu Arg Gly Cys Leu Leu
1               5                   10                  15

Asn Phe Leu Arg Gln Arg Gln Gly His
            20                  25

<210> SEQ ID NO 6
<211> LENGTH: 25
<212> TYPE: PRT
<213> ORGANISM: Homo sapiens

<400> SEQUENCE: 6

Lys Pro Leu Tyr Ile Val Thr Glu Phe Met Glu Asn Gly Cys Leu Leu
1               5                   10                  15

Asn Tyr Leu Arg Glu Asn Lys Gly Lys
            20                  25

<210> SEQ ID NO 7
<211> LENGTH: 25
<212> TYPE: PRT
<213> ORGANISM: Homo sapiens
```

```
<400> SEQUENCE: 7

Ala Pro Ile Cys Leu Val Phe Glu Phe Met Glu His Gly Cys Leu Ser
1               5                   10                  15

Asp Tyr Leu Arg Thr Gly Arg Gly Leu
            20                  25

<210> SEQ ID NO 8
<211> LENGTH: 25
<212> TYPE: PRT
<213> ORGANISM: Homo sapiens

<400> SEQUENCE: 8

Ser Thr Val Gln Leu Ile Thr Gln Leu Met Pro Phe Gly Cys Leu Leu
1               5                   10                  15

Asp Tyr Val Arg Glu His Lys Asp Asn
            20                  25

<210> SEQ ID NO 9
<211> LENGTH: 25
<212> TYPE: PRT
<213> ORGANISM: Homo sapiens

<400> SEQUENCE: 9

Ser Thr Val Gln Leu Val Thr Gln Leu Met Pro Tyr Gly Cys Leu Leu
1               5                   10                  15

Asp His Val Arg Glu Asn Arg Gly Arg
            20                  25

<210> SEQ ID NO 10
<211> LENGTH: 25
<212> TYPE: PRT
<213> ORGANISM: Homo sapiens

<400> SEQUENCE: 10

Pro Thr Ile Gln Leu Val Thr Gln Leu Met Pro His Gly Cys Leu Leu
1               5                   10                  15

Glu Tyr Val His Glu His Lys Asp Asn
            20                  25

<210> SEQ ID NO 11
<211> LENGTH: 25
<212> TYPE: PRT
<213> ORGANISM: Homo sapiens

<400> SEQUENCE: 11

Pro Glu Leu Arg Leu Val Met Glu Tyr Leu Pro Ser Gly Cys Leu Arg
1               5                   10                  15

Asp Phe Leu Gln Arg His Arg Ala Arg
            20                  25

<210> SEQ ID NO 12
<211> LENGTH: 25
<212> TYPE: PRT
<213> ORGANISM: Homo sapiens

<400> SEQUENCE: 12

Glu Pro Ile Tyr Ile Val Thr Glu Tyr Met Ala Arg Gly Cys Leu Leu
1               5                   10                  15

Asp Phe Leu Lys Thr Asp Glu Gly Ser
            20                  25
```